United States Patent
Li et al.

(10) Patent No.: US 10,174,354 B2
(45) Date of Patent: Jan. 8, 2019

(54) RECOMBINANT PHE-FREE PROTEINS FOR USE IN THE TREATMENT OF PHENYLKETONURIA

(71) Applicant: NEXTTOBE AB, Uppsala (SE)

(72) Inventors: Qingshan Li, Gainesville, FL (US); Olof Kämpe, Uppsala (SE)

(73) Assignee: NEXTTOBE AB, Uppsala (SE)

( * ) Notice: Subject to any disclaimer, the term of this patent is extended or adjusted under 35 U.S.C. 154(b) by 0 days.

(21) Appl. No.: 15/512,974

(22) PCT Filed: Sep. 22, 2015

(86) PCT No.: PCT/EP2015/071788
§ 371 (c)(1),
(2) Date: Mar. 21, 2017

(87) PCT Pub. No.: WO2016/046234
PCT Pub. Date: Mar. 31, 2016

(65) Prior Publication Data
US 2018/0016613 A1    Jan. 18, 2018

Related U.S. Application Data

(60) Provisional application No. 62/053,433, filed on Sep. 22, 2014.

(51) Int. Cl.
| | | |
|---|---|---|
| C12P 21/02 | (2006.01) |
| A61K 38/00 | (2006.01) |
| A23L 33/17 | (2016.01) |
| C07K 14/76 | (2006.01) |
| C07K 14/435 | (2006.01) |
| C12N 9/20 | (2006.01) |
| C12N 9/26 | (2006.01) |
| C12N 9/50 | (2006.01) |
| C12N 9/64 | (2006.01) |
| C12N 9/54 | (2006.01) |

(52) U.S. Cl.
CPC .............. *C12P 21/02* (2013.01); *A23L 33/17* (2016.08); *A61K 38/00* (2013.01); *C07K 14/43595* (2013.01); *C07K 14/76* (2013.01); *C12N 9/20* (2013.01); *C12N 9/2414* (2013.01); *C12N 9/50* (2013.01); *C12N 9/54* (2013.01); *C12N 9/6424* (2013.01); *C12N 9/6472* (2013.01); *C12Y 304/21062* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2011/0171718 A1* | 7/2011 | Pisarchik | ................. | C12N 9/54 435/221 |
| 2015/0307562 A1* | 10/2015 | Basu | ..................... | A61K 38/16 530/350 |

FOREIGN PATENT DOCUMENTS

| | | |
|---|---|---|
| WO | WO 94/28126 A2 | 12/1994 |
| WO | WO 95/02692 A1 | 1/1995 |
| WO | WO 95/23614 A1 | 9/1995 |
| WO | WO 96/17064 A1 | 6/1996 |
| WO | WO 2013/148332 A1 | 10/2013 |

OTHER PUBLICATIONS

Sequence Alignment of Instant SEQ ID No. 12 with SEQ ID No. 109, Searched conducted on Mar. 29, 2018, 2 pages.*
Database Geneseq [Online], "Subtilisin-A," retrieved from EBI accession No. GSP:AAR84523, Database accession No. AAR84523, Mar. 9, 1996.
Lim et al., "Acceptable low-phenylalanine food and beverages can be made with glycomacropeptide from cheese whey for individuals with PKU," Molecular Genetics and Metablolism, vol. 92, No. 1-2, pp. 176-178, Sep. 1, 2007.
Baranyi et al., "Isolation and some effects of functional, low-phenylalanine kappa-casein expressed in the milk of transgenic rabbits," Journal of Biotechnology, vol. 128, No. 2, pp. 383-392, Jan. 13, 2007.
International Search Report dated Jun. 24, 2016 in application No. PCT/EP2015/071788.

* cited by examiner

*Primary Examiner* — Channing S Mahatan
(74) *Attorney, Agent, or Firm* — Foley & Lardner LLP

(57) ABSTRACT

The present invention relates to a method for preparing a recombinant Phe-free or Phe-low protein, the method comprising using *B. subtilis* or *B. licheniformis* as an expression system and/or a recombinant host cell into which a nucleotide encoding a recombinant Phe-free or Phe-low protein has been inserted into the genome.

19 Claims, 21 Drawing Sheets

Figure 1:
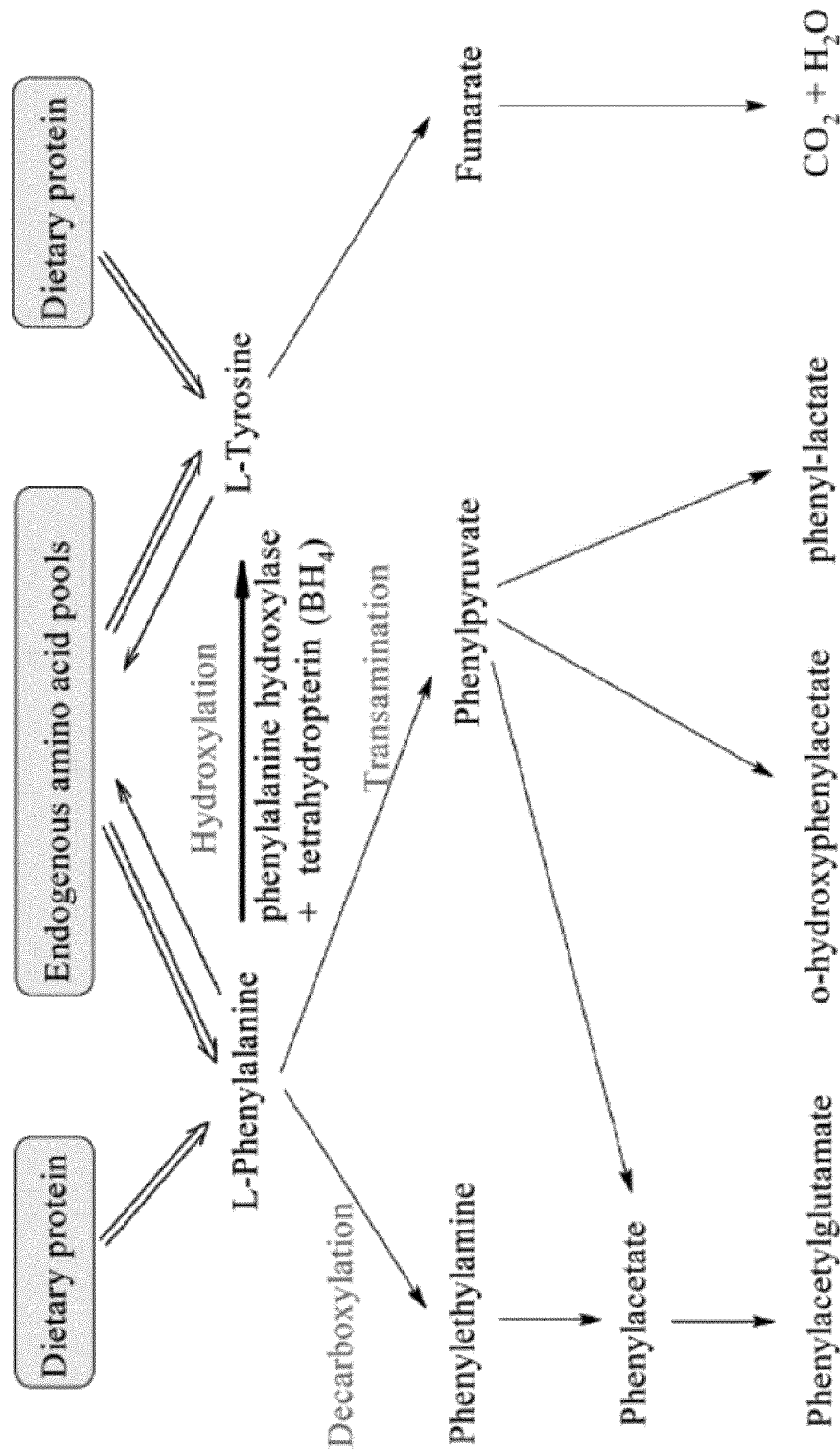

Specification includes a Sequence Listing.

ically in ASCII format and is
RECOMBINANT PHE-FREE PROTEINS FOR USE IN THE TREATMENT OF PHENYLKETONURIA

SEQUENCE LISTING

The instant application contains a Sequence Listing which has been submitted electronically in ASCII format and is hereby incorporated by reference in its entirety. Said ASCII copy, created on Aug. 16, 2017, is named 109036-0104_SL.txt and is 139,060 bytes in size.

FIELD OF THE INVENTION

The present invention relates to the field of treating the condition generally referred to as phenylketonuria (PKU) or Följing's disease that is an inherited metabolic disorder in human and animals resulting in an accumulation of L-phenylalanine and its metabolites. In particular the invention relates to phenylalanine-free proteins (Phe-free proteins) for use in patients suffering from phenylketonuria, to methods for preparing the Phe-free proteins, to compositions comprising the Phe-free proteins, and to medicated food products comprising the Phe-free proteins.

BACKGROUND OF THE INVENTION

In 1934, a doctor in Norway named Asbjorn Följing noticed that several mentally retarded patients had a strange odor. He figured out that it was from something called "phenylacetic acid". The patients' urine also had a very high level of a chemical called "phenylketone", which is reflected in the name of the disease, phenylketon-uria. Följing also thought the disease was most likely inherited, and was the first to suggest using diet to manage it. Since then, giant steps have been made in understanding and treating PKU.

Phenylketonuria (PKU), one of the most common inborn error of amino acid metabolism, results from an impaired ability to metabolize the essential amino acid phenylalanine (Phe)[1] and convert it to its hydroxylated derivative tyrosine (Tyr). Classical PKU is a rare metabolic disorder and classified as an orphan disease both according to US and European definitions. PKU usually results from a deficiency of a liver enzyme known as phenylalanine hydroxylase (PAH) but can also result from deficiencies in enzymes needed to produce pyridoxalphosphate, an obligate co-factor to PAH. The enzyme deficiency leads to accumulation of Phe in the blood and other tissues. Phenylalanine is found in breast milk, many types of baby formula, and most foods, especially those containing a high concentration of protein, such as meat, eggs, and dairy products. If PKU is not treated, phenylalanine will build up in the blood and eventually lead to irreversible intellectual disability and problems within the central nervous system (brain and spinal cord). The untreated state is characterized by mental retardation, microcephaly, delayed speech, seizures, eczema, behavioral abnormalities, and other symptoms. The good news is that early treatment can prevent all or most problems. Babies born with PKU need to start treatment with special formula soon after birth. The mainstream treatment for classic PKU patients is a strict Phe-restricted diet supplemented by a medical formula containing free amino acids except Phe and other nutrients covering the demands of the organism of essential amino acids. In the United States, the current recommendation is that the PKU diet should be maintained for life. Patients who are diagnosed early and maintain a strict diet can have a normal life span with normal mental development.

Compliance to a strict Phe-restricted diet supplemented with a medical formula will, however, decrease as the subject gets older and this decrease in compliance may cause later development of cognitive dysfunction. Inadequate compliance may be due to the unpleasant taste and smell of the amino acids formulations as well as a desire to live like normal subjects, who do not suffer from PKU.

The present invention provides recombinant Phe-free proteins for use in the treatment of PKU. Such proteins may be used as such or they may be incorporated into foods. The recombinant Phe-free proteins according to the invention have advantages over the known medical food proteins used in the treatment of PKU as they have improved properties with respect to i) taste, ii) smell, iii) palatability, and iv) texture and, which enhances the acceptability and compliance of the proteins of the present invention and the compositions/medical food containing them.

In the following is given an overview of the disease and treatment options.

Incidence and Newborn Screening

The incidence of PKU is approximately one in every 15,000 births (1/15,000). It affects around 700,000 people around the globe[5]. The overall birth prevalence of PKU in European, Chinese and Korean populations is ~1/10,000. The mean incidence of PKU varies widely in different human populations (Table 1). United States Caucasians are affected at a rate of 1 in 10,000. Turkey has the highest documented rate in the world, with 1 in 2,600 births, while countries such as Finland and Japan have extremely low rates with fewer than one case of PKU in 100,000 births. A 1987 study from Slovakia reports a Roma population with an extremely high incidence of PKU (one case in 40 births) due toa frequency of cousin marriages.

PKU is commonly included in the newborn screening panel of most countries, with varied detection techniques. Most babies in developed countries are screened for PKU soon after birth. Screening for PKU is done with bacterial inhibition assay (Guthrie test), immunoassays using fluorometric or photometric detection, or amino acid measurement using tandem mass spectrometry (MS/MS). Measurements done using MS/MS determine the concentration of Phe and the ratio of Phe to Tyr.

If a child is not screened during the routine newborn screening test (typically performed 2-7 days after birth, using samples drawn by neonatal heel prick), the disease may present clinically with seizures, albinism (excessively fair hair and skin), and a "musty odor" to the baby's sweat and urine. In most cases, a repeat test should be done at approximately two weeks of age to verify the initial test and uncover any phenylketonuria that was initially missed. The affected children who are detected and treated are less likely to develop neurological problems or have seizures and mental retardation, though such clinical disorders are still possible.

Phe Metabolic Pathways

Phe exists as D and L enantiomers, and L-Phe is an essential amino acid required for protein synthesis in human [6]. There are many processes (FIG. 1), which contribute to the flux of L-Phe in human. The main pathway is the enzyme PAH normally converts the amino acid phenylalanine into the amino acid tyrosine. However, other pathway reactions also occur in normal liver tissue but are of minor significance. As with many other metabolites, Phe concentrations are regulated to a steady state level with dynamic input and run-out flux. Persistent disturbance to the flux will eventually result in alteration of the steady state concentrations and accumulation of Phe[7]. Excessive Phe can be metabolized into phenylketones through the minor route, a transaminase pathway with glutamate. Metabolites include phenylacetate, phenylpyruvate and phenethylamine. Elevated levels of phenylalanine in the blood and detection of phenylketones in the urine are ways to diagnose PKU, however most patients are diagnosed via newborn screening.

Figure 2:
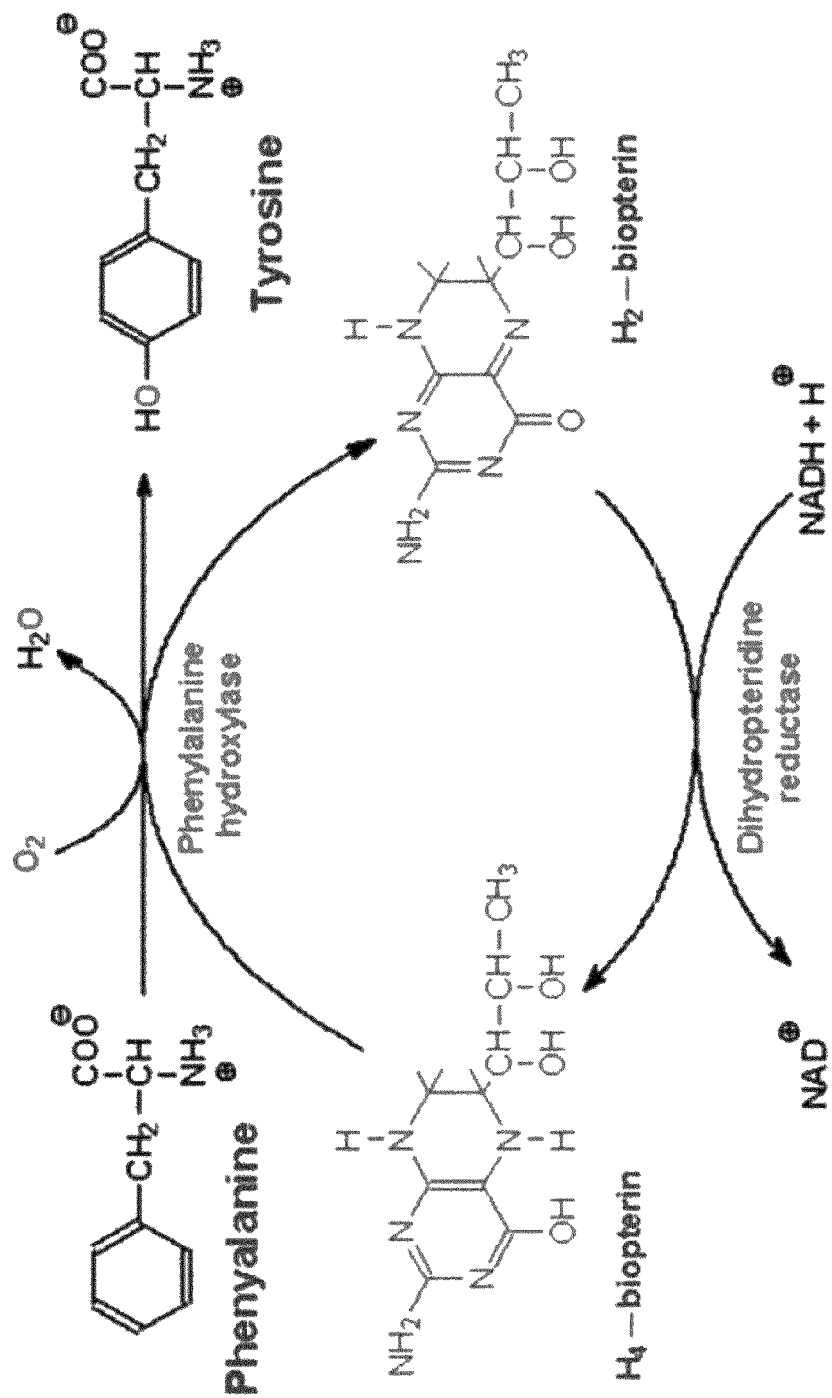

PAH enzyme requires tetrahydrobiopterin (BH4) as an essential co-factor, which is formed in three steps. During the hydroxylation reaction BH4 is converted to the inactive pterin, BH2, dihydrobiopterin (quinone). The enzyme dihydropteridine reductase (DHPR) regenerate BH4 (FIG. 2). BH4 is also an obligate co-factor for tyrosine hydroxylase, tryptophan hydroxylase, and for nitric oxide synthase and is thus necessary for the production of dopamine, catecholamines, melanin, serotonin, and for nitric oxide. Defects in either PAH or the production or recycling of BH4 may result in hyperphenylalaninaemia.

Phenylalanine is a large neutral amino acid (LNAA). LNAAs compete for transport across the blood-brain barrier (BBB) via the large neutral amino acid transporter (LNAAT). If phenylalanine is in excess in the blood, it will saturate the transporter. Excessive levels of phenylalanine tend to decrease the intratechal levels of other LNAAs (Tyr, Trp, Thr, Ile, Leu, Val, Met and His) in the brain. As these amino acids, especially Tyr and Trp, are necessary for protein and neurotransmitter synthesis, Phe buildup hinders the development of the brain, causing mental retardation.

Phenylalanine levels are monitored typically twice a week in neonates, weekly in infants, biweekly or every 3 weeks in toddlers, and monthly thereafter, even during adult life. Attention should be given to variability in blood phenylalanine levels and to maintenance within the recommended range. During pregnancy, weekly phenylalanine sampling is recommended.

Types of PKU

Classical PKU is caused by a mutated gene for the enzyme PAH, which converts the Phe to other essential compounds in the body. Other non-PAH mutations can also cause PKU. The PAH gene is located on chromosome 12 in the bands 12q22-q24.1. More than 400 disease-causing mutations have been found in the PAH gene. PAH deficiency causes a spectrum of disorders, including classic PKU and hyperphenylalaninemia (a less severe accumulation of phenylalanine).

PKU is known to be an autosomal recessive genetic disorder. This means both parents must have at least one mutated allele of the PAH gene. The child must inherit both mutated alleles, one from each parent. Therefore, it is possible for a parent with the disease to have a child without it if the other parent possesses one functional allele of the gene for PAH. Yet, a child from two parents with PKU will inherit two mutated alleles every time and therefore the disease.

PKU can exist in mice, which have been extensively used in experiments into finding an effective treatment for it. The availability of a mutant mouse that closely mimics the human disease, called PAH$^{enu2}$ provides an ideal model for investigating gene transfer in vivo and invaluable information on the pathology and biology of PKU. Numerous genetic and biochemistry studies have confirmed the reliability of this mouse model to closely resemble the metabolic and neurobiological phenotype of human PKU. The macaque monkey's genome was recently sequenced, and the gene encoding phenylalanine hydroxylase was found to have the same sequence that, in human, would be considered as a PKU mutation.

Tetrahydrobiopterin-deficient hyperphenylalaninemia is a rare, explaining about 1-5% of all PKU cases. These patients have normal PAH, but lack the ability in the biosynthesis or recycling of the cofactor tetrahydrobiopterin (BH4). BH4 is necessary for proper activity of the enzyme. Tetrahydrobiopterin deficiency can be caused by defects in four different genes. These types are known as HPABH4A, HPABH4B, HPABH4C, and HPABH4D.

Treatment of PKU

The foundation of PKU treatment is a low Phe diet which prevents the development of the neurological and psychological changes. Since neurological changes have been demonstrated within one month of birth, it is recommended that dietary restriction should be started early and be continued through childhood when neural development is maximal. Clinical neurological abnormalities, affected neuropsychological performance and brain imaging in adults with PKU has led to a consensus opinion that the PKU diet should be followed for life. An even more stringent regime of Phe restriction is required for women with PKU contemplating starting a family, particularly during pregnancy, as elevated blood Phe concentrations are teratogenic towards the developing foetus. A preconception diet is required with a S-Phe target interval of between 100 and 360 µmol/L in affected mothers.

Figure 3:
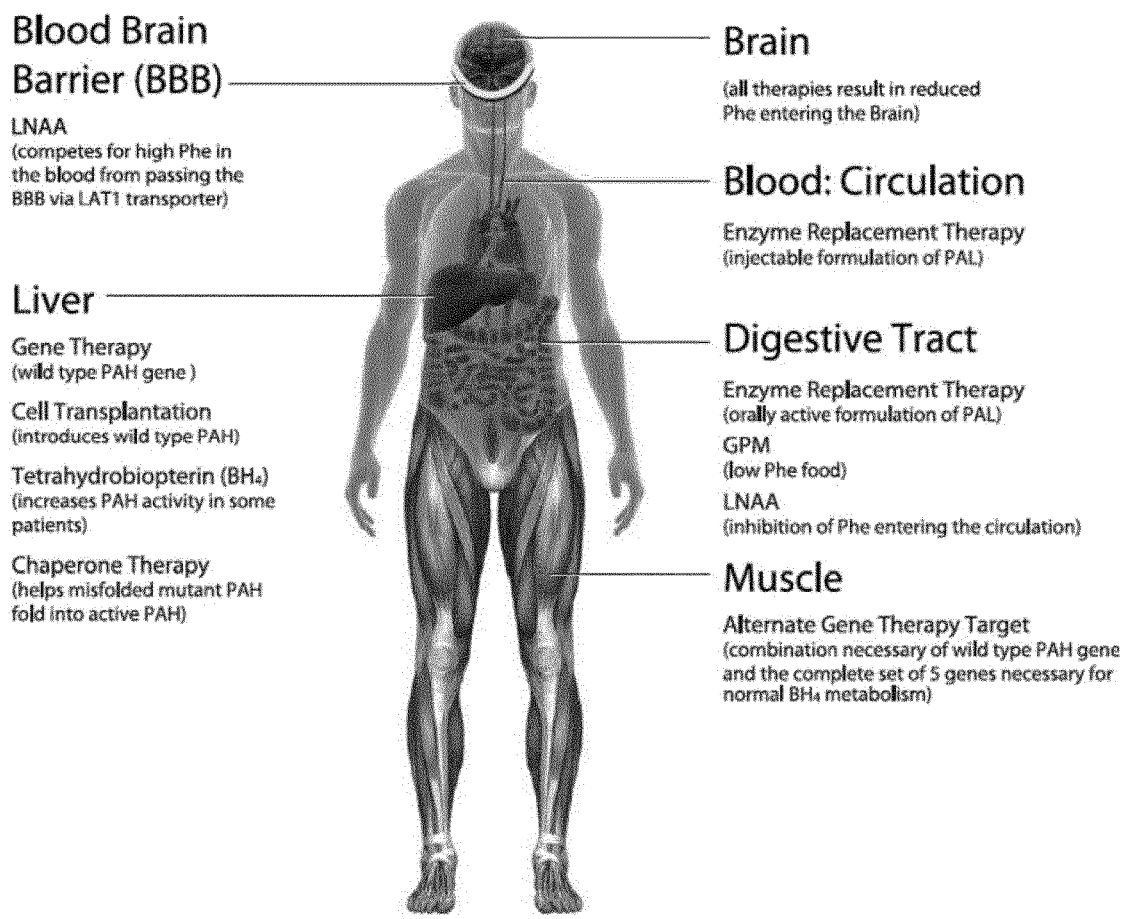

A Phe-restriction diet can lower plasma Phe levels and may prevent the mental impairments of PKU patients. However, compliance with dietary treatment erodes, as patients get older. Because some patients are not able to adhere rigorously to the phenylalanine-restricted diet during life, alternative treatment regimens have been developed. Moreover, Pregnant PKU/HPA women have a particular need for keeping the Phe levels low, since high level of Phe affects the embryo and fetus (maternal PKU). The UK MRC Study Group on PKU has concluded that there is a need for an alternative to the low-Phe diet. The NIH Consensus Panel also encouraged research on therapeutics for PKU, including enzyme therapy and gene therapy. FIG. 3 shows several kinds of treatment options available in practice or in theory for PKU therapy[8].

Dietary Modifications

If PKU is diagnosed early enough, an affected newborn can grow up with normal brain development, but only by managing and controlling Phe levels through diet, or a combination of diet and medication. An optimal health range of Phe in plasma is between 120 and 360 µmol/L, and a people with PKU should control their Phe for life, as determined by experts convened by the National Institutes of Health (NIH). Most natural foods contain protein containing 2.4-9% Phe by weight[9]. All PKU patients must adhere to a special diet low in Phe for optimal brain development (below 500 mg/day). The diet requires severely restricting or eliminating foods high in Phe, such as meat, chicken, fish, eggs, nuts, cheese, legumes, milk and other dairy products. Starchy foods, such as potatoes, bread, pasta, and corn, must be monitored. Infants may still be breastfed to provide all of the benefits of breast milk, but the quantity must also be monitored and supplementation for missing nutrients will be required. The sweetener aspartame (L-aspartyl-L-Phe methyl ester), present in many diet foods and soft drinks, must also be avoided, as the metabolism of the dipeptide aspartame will release Phe, L-aspartic acid and methanol.

Low-Phe diet often includes: Low-Phe natural foods (some fruits and vegetables), Low-protein specialty foods (low-protein pasta, bread, etc.), Phe-free formula and Phe-free protein replacement bars, tablets, capsules, etc. Supplementary infant formulas are used in these patients to provide the amino acids and other necessary nutrients that would otherwise be lacking in a low-phenylalanine diet. As the child grows up these can be replaced with pills, formulas, and specially formulated foods. Since Phe is necessary for the synthesis of many proteins, it is required for appropriate growth, but levels must be strictly controlled in PKU patients. In addition, tyrosine, which is normally derived from phenylalanine, must be supplemented.

Supplementation with amino acid (AA) modified medical food (PKU formula) and low protein food is necessary on a daily basis for successful PKU management. But as mentioned above, the taste and smell of the AA formulas are offensive, so changing the form of AAs into proteins without Phe would enhance taste, palatability and acceptability of the PKU medical food and ultimately lead to improved dietary compliance.

Glycomacropeptide (GMP), a 64-amino acid glycophosphopeptide cleaved from κ-casein during cheese making, is found in bovine whey[9, 10]. GMP protein is naturally low in Phe, and can be purified further to contain just 2.5-5.0 mg Phe per g of GMP powder[9]. A variety of foods and beverages can be made with GMP to improve the taste, variety and convenience of the PKU diet. It provides a palatable alternative source of protein that may improve dietary compliance and metabolic control of PKU[11, 12]. However, GMP alone does not possess a suitable amino acid profile for PKU treatment and supplement with amino acids including histidine, leucine, tryptophan and tyrosine is therefore required[13]. Therefore, developing a series of recombinant proteins that have suitable amino acid profile as AA formulas and contain low or no Phe will make up for the deficiency of GMP for PKU treatment.

Enzyme Therapy for PKU

There is an increasing interest in enzyme replacement therapy for metabolic diseases. Two enzyme systems are being developed for treatment of PKU: the PAH enzyme and the Phe-degrading enzyme from plants, phenylalanine ammonia-lyase (PAL)[1].

Enzyme Replacement Therapy Using PAH

Enzyme replacement therapy is a viable option to supply active PAH[14]. However, for this to work, there will be a need to administer the PAH cofactor BH4[15], either orally or by addition of the (BH2 to BH4) recycling enzyme dihydropteridine reductase. Although the cofactor requirement is a disadvantage in the use of PAH for enzyme replacement therapy, there are several advantages, which include that the protein is well expressed in bacteria, particularly the doubly truncated form; the expressed protein in the human form of the disease; the protein is easily PEGylated and retain its enzymatic activity, unlike many other enzymes that have been attempted; and the PEGylated protein is very stable after PEGylation. Another advantage of PAH replacement therapy is that additional Tyr supplementation may be unnecessary in PKU therapy. However, the inherent protease sensitivity and potential immunogenicity of PAH have precluded adoption of this approach. Exploring pegylated-PAH as a long-term injectable molecule for PKU is ongoing, but given the drawbacks of the enzyme, its viability as a therapeutic remains debatable[7]. Moreover, using this therapy method high-dose BH4 supplementation is required, which is currently too expensive to afford for most of PKU patients. Therefore, enzyme replacement therapy using PAH will not be a good choice.

Enzyme Replacement Therapy Using PAL

An alternative enzyme therapy for PKU involves the use of PAL, an enzyme capable of substituting for PAH. As a non-mammalian enzyme, PAL is widely distributed in plants, fungi and bacteria. PEgylated PAL derived from algae is currently under investigation for the potential treatment of patients with PKU who do not respond to BH4. PALs can catalyze the conversion of L-phenylalanine to harmless metabolites of trans-cinnamic acid and ammonia without a cofactor requirement. In comparison to PAH, PAL therapy for PKU has some advantages. PAL requires no cofactors for degrading Phe, and trans-cinnamate acid has a very low toxicity and no embryotoxic effects in experimental animals. The PAL product trans-cinnamic acid is converted in the liver to benzoic acid, which is then excreted via the urine mainly as hippurate. PAL is very stable under a wide temperature range.

PAL was investigated to treat PKU as early as 1980 and enzyme replacement therapy studies in human PKU patients began with the oral administration of PAL in entericcoated gelatin capsules. However, when oral administration of the free PALs, enzymes were inactivated rapidly in the gastrointestinal tract due to intestinal proteolysis. Therefore, pretreatment was necessary to protect the PAL enzyme against gastric acidity and pancreatic proteases. Although pharmacological and physiological proofs of principal were attained using PKU mouse model studies, the extreme sensitivity of PAL to low pH and intestinal proteolytic degradation has hindered successful progression of this therapy to clinical trials[14]. However, if an acid stable PAL is found, encapsulated formulation may help reduce plasma Phe. For examples, immobilized PAL within artificial cells was more effective than a phenylalanine-free diet in PKU rats to lower Phe in the plasma, intestinal and cerebrospinal fluids. Oral administration of enteric-coated capsules (ENC) PAL can lower the plasma phenylalanine levels as well. However, oral administration of PAL may need to combine with Phe restrict diet together to get better control of plasma Phe level[19].

Although oral administration of PAL will be more comfortable for the patient, a parenteral modality for PAL therapy needs to be considered. The highly immunogenic property of PAL is a serious problem for parenteral PAL therapy, since it may lead to a short half-life of the enzyme in the blood and unwanted immunologic responses. To overcome these problems, multi-tubular enzyme-reactors with immobilized PAL (from R. glutinis) were investigated and resulted in a rapid, 77% removal of Phe in blood samples of PKU patients[1]. A sustained reduction of Phe was exhibited in less than 1 h, in vitro. Repeated use of PAL reactors in animals did not produce unwanted immunological reactions. However, extracorporeal hollow fibers containing PAL cannot be easily administered to young children, although it may be recommended for PKU management in pregnant women.

Another way to reduce the degree of immunoreactions is PEGylation[1] [16]. The halflives of native PAL and linear PEGylated PAL were 6 and 20 h after the 1st injection, respectively. PEGylated PAL[17] [18] (PEG-PAL, Biomarin Pharmaceuticals) has been shown to suppress immunogenicity and is currently being investigated in Phase 3 clinical trials in the USA. PAL activity is low due to it catalyzes the reversal reaction as well, therefore, a large dose may be required.

Many patents, eg U.S. Pat. No. 5,753,487, EP0260919A1, EP0260919B1, U.S. Pat. No. 4,757,015, EP0703788B1, EP0703788A1, U.S. Pat. No. 4,562,151, U.S. Pat. No.

4,636,466, U.S. Pat. No. 4,681,850, U.S. Pat. No. 4,248,704, U.S. Pat. No. 4,598,047, EP0140707A2, EP0140714A2, U.S. Pat. No. 4,584,273, U.S. Pat. No. 4,584,273, EP0136996A2, JP60172282, JP61139383, JP58086082, U.S. Pat. No. 7,531,341, US 20070048855, U.S. Pat. No. 4,574,117, etc. cover PLA-producing microbial cells, PLA sequence, fermentation, stabilizing agent, variants and chemically-modified variants.

Gene Therapy

Gene therapy for the treatment of PKU has been ongoing over the last 2 decades. The focus has been on replacement of the human mutant PAH gene in somatic cells of PKU patients[20]. Gene therapy is an experimental, yet very promising approach for PKU treatment. Advances in PKU treatment by gene therapy have been accelerated by the availability of pre-clinical models of disease. Early work on gene therapy for children with PKU was considered inappropriate as the therapy involved administration of immunosuppressant agents to block the immune response to the vector so as to prolong the therapeutic effect. Gene Therapy of PKU using viral vectors has had some success in phenotypic correction of the PAH$^{enu2}$ mice in vivo. Infusion of recombinant adenoviral vectors to the liver resulted in a significant increase in PAH activity leading to complete normalization of the serum Phe levels within one week of treatment. However, the effect did not persist and repeated administrations did not generate the original results due to neutralizing antibodies against the viral vectors. Furthermore, no phenotypic changes were observed and the mice remained hypo-pigmented. In another study, delivery of a recombinant AAV to the liver by portal vein injection resulted in correction of Phe levels in male mice. Females remain unresponsive unless they were ovariectomized and treated with testosterone. The biochemical basis behind this sexual dismorphism was shown to be due to a lower level of BH4 which is controlled primarily by oestrogen and represents a rate limiting factor of PAH activity. Other trials involving the use of recombinant retroviral vectors have been abandoned following the observetion that these vectors may induce leukaemia-like disorders.

Liver-directed gene therapy using recombinant adeno-associated virus serotype 8 vectors (rAAV8) has achieved long-term correction (up to 1 year) of blood Phe concentration in Pah$^{enu2}$ mice without inducing the immune-mediated rejection seen following adenoviral therapy. However, rAAV8-mediated therapy does not lead to permanent correction of liver PAH deficiency; it is thought that gradual but continuous hepatocyte regeneration eventually leads to elimination of episomal rAAV vector genomes and loss of PAH expression. Reinjection of the same serotype vector is ineffective because of antibody-mediated destruction of the vector.

Initial investigations using non-viral vectors for PKU has thus far been unsuccessful. Injection of naked pDNA by portal vein or hydrodynamic injection with a CMV promoter-driven plasmid resulted in transient PAH expression and a marginal decrease in serum Phe levels, which was not sustained beyond 24 h. Improvements in vector design and engineering using regulatory and/or enhancer elements, as well as insulators, are currently being investigated in order to prolong PAH expression.

Apart from the reports on liver transfection, there are some innovative studies on muscle as a target for gene therapy because adult muscle lacks ongoing cell division. In order to introduce the Phe hydroxylating system into tissue other than the liver, gene delivery must include not only the PAH enzyme but also transport genes that encode the complete enzyme system necessary to synthesize and recycle BH4. Despite such a daunting technical challenge, Ding et al.[21] has shown this to be possible in mice. An advantage of this approach is the ease of access for vectors as compared with liver-directed gene therapy[8].

However, the safety and toxicity and the potential for insertional mutagenesis following viral gene transfer remain an issue. Improvements are necessary to completely eliminate any potential for immune responses. Moreover, after the unfortunate death of a patient with another inborn error of metabolism (ornithine transcarbamylase deficiency)[22], it became clear that there were important issues to be addressed before a gene therapy strategy could be used widely in PKU patients.

BH4 Therapy

The (6R)-L-erythro-5,6,7,8-tetrahydrobiopterin (BH4) is a cofactor in the hydroxylation of Phe to Tyr by PAH[5]. BH4 deficiency accounts for approximately 2% of the high Phe concentrations detected during newborn screening. BH4 is synthesized de novo from GTP by a three enzyme pathway involving GTP cyclohydrolase I (GTPCH I), 6-pyruvoyltetrahydrobiopterin synthase (PTPS) and sepiapterin reductase (SPR) (FIG. 4), and is abundant in the liver. For several decades, BH4 has been used clinically to treat BH4 deficiency, a condition that also can result in elevated blood Phe levels. Several recent studies indicate that approximately 30-50% of PKU patients are responsive to pharmacological doses of BH4, showing a drop in blood Phe levels following a dose of it. However, even some patients with a mutation in the gene encoding PAH, resulting in a clear lack of enzyme activity, might show some response. Experience shows that most of the patients responsive to BH4 still need restriction of natural protein and continued use of low-Phe medical foods. A tablet formulation of BH4 (dihydrochloride) has been available for three decades. Although this formulation has been used extensively in experimental studies, it has not been evaluated in formal clinical trials and was not registered. In addition, BH4 shows limited efficacy in some PKU genotypes and its chemical synthesis is very costly[23].

Many pharmacological chaperones, which are small molecules improving protein stability by rectifying protein folding, have been tried in vitro studies considering PKU as a protein mis-folding disorder[25]. Several researchers have shown that mis-folded PAH protein can be stabilized by BH4 therepy[26, 27]. BH4 prevented the degradation of protein folding variants, proving its effect as a chemical chaperone. A high throughput screening has been performed with more than 1,000 pharmacological compounds and found four compounds which enhanced the thermal stability of wild type PAH and other mutants[28].

A newer formulation of BH4 [sapropterin dihydrochloride (Trade name: Kuvan®), Biomarin Pharmaceuticals] that is more stable at room temperature is now available for the treatment of PKU in the USA and Europe. The synthetic cofactor to PAH, Kuvan® (FIG. 5), acting as a chaperone on the mis-folded PAH protein caused by certain missense PAH mutations, has brought about partial or complete correction of HPA in some patients. Kuvan® is the first drug in the management of PKU approved as an orphan drug by the US Food and Drug Administration (FDA). Sapropterin therapy may also offer relaxation in the strict dietary regimen in patients with mild PKU[29]. Combination of sapropterin with a low-Phe diet increases the stability of blood Phe concentrations and may improve tolerance to dietary Phe[30, 31].

The cost of daily BH4 therapy is very high, for an example, at the highest dose of 20 mg/kg/day, it is US $100,000 to $150,000 for the average adult patient versus the cost of the Phe-restricted diet, including the use of medical foods, which is typically US $15,000 to $20,000 per year. The short half-life (3.3-5.1 h) of BH4 therapy requires frequent dosing, which further accrues treatment cost[5]. Going forward, development of affordable forms of BH4 substitutes or sustained release dosage forms may result in the reduction in the cost of therapy. BH4 supplements may be supplied with classical dietary therapy to achieve better results.

In order to decrease the cost of BH4, some patents have provided the methods for chemical synthesis BH4[33], stable solid formulations BH4[34] and efficiently producing biopterins (BP) by biotransformant[35-38]. The recombinant *Escherichia coli* show significantly higher productivity, up to 4.0 g of biopterin/L of culture broth[38], which suggests the possibility of commercial BH4 production by biotransformation. There are some patents (WO/2002/018587A1, US20040014167, US20060008869, US20090104668, WO/2006/085535A1, EP1314782A1, EP1314782A4 and CN1449442A) covering the methods for producing BP compounds using BH4 biosynthesis enzymes. Although BP can be bio-transformed by the salvage pathway using BH4 biosynthesis enzyme SPR and DHPR as well, sepiapteriu as the precursor of BH4 biotransformation is also expensive.

Large Neutral Amino Acid Therapy

Large Neutral Amino Acid (LNAA) therapy is an emerging alternative treatment for older individuals with PKU. The concept behind LNAA treatment is that Phe and other LNAA (Arginine, Histidine, Isoleucine, Leucine, Lysine, Methionine, Phenylalanine, Threonine, Tryptophan, Tyrosine And Valine) share the same transport system, creating competitive inhibition of the transport of LNAA with each other[39, 40]. Therefore, supplementation with LNAA blocks the uptake of Phe by actively controlling cell receptor sites, effectively reducing Phe concentration in the brain. However, the effect of LNAA supplementation on blood Phe concentration might be a result of other factors, including stimulating anabolism or potentially improving the competitive effect of LNAA resulting from decreased natural protein intake, rather than directly influencing transport mechanisms. This is in line with the finding that the blood Phe concentration decreases when amino acid supplements are given more frequently in conjunction with non-LNAA[8].

Supplementation with commercial preparations of LNAA has been noted to reduce brain and circulating levels of Phe in PKU mice and to reduce brain Phe levels in PKU adults off diet as measured by magnetic resonance spectroscopy. LNAAs may be ideal for young adults, for poorly compliant patients, and for late-diagnosed patients in whom compliance is low and in whom drinking formula can be a burden for the patient and caretakers. Adults and older teenagers refusing dietary restrictions can be prescribed a preparation of high-dose LNAAs. The long-term outlook merits further study. Young women of childbearing age need to realize this drug does not protect their fetus from the teratogenic effects of Phe.

Figure 6:
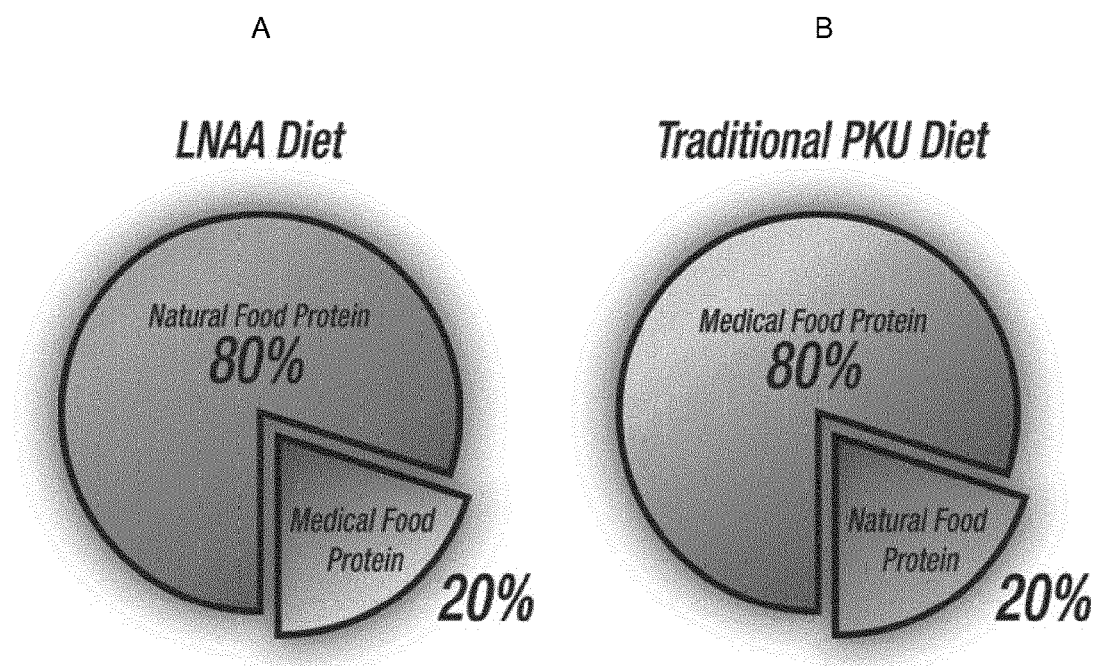

Although LNAA treatment does not completely replace the PHA diet, it does help ease the dietary restriction for treated individuals by allowing for a larger amount of natural food protein (FIGS. 6A and B). While diet treatment is always very individual, the LNAA diet may allow the inclusion of regular bread, rice, pasta, and other grains eliminating the need to purchase costly low protein foods. Treatment with LNAA can be especially useful for those struggling with dietary compliance. The 'relaxed diet' associated with LNAA therapy, not only improves the dietary options for those living in long-term care environments, but also quality of life. Significant improvements in concentration and decreased self-injurious behavior have been reported in previously untreated adults on a normal diet and LNAA supplementation.

PreKUlab Company has developed some LNAA tablets (PreKUnil and Avonil series, NeoPhe) prekulab.com/products2/neophe-tablets.html). The tablets must be combined with a certain amount of natural protein in order for the diet to contain sufficient protein. After numerous years of experiments and trials with PreKUnil tablets, a group of experts in biochemical and molecular genetics came up with a new formula for PKU treatment—NeoPhe tablets, which has been effective in reducing blood Phe concentrations. However, long-term study of NeoPhe and placebo needs to be conducted in order to establish the efficacy and tolerance of NeoPhe in long term treatment of PKU. Moreover, the taste and smell will also be a problem for people to accept those LNAA tablets. So protein substitute with high in LNAA, but low or no Phe, would control plasma Phe in suitable level, meanwhile enhance taste, palatability and acceptability of the PKU medical food.

As it appears from the description of the various treatment options for PKU, none of the known options provide an optimal solution for the subjects suffering from PKU:

Phe-Restricted Diet with Medical Supplement

The medical food protein that is supplemented to a restricted Phe diet contains amino acids that have an unpleasant taste and smell and it may therefore be difficult to comply with the treatment regime.

Glycomacropeptide (GMP) is not free of Phe and alone it does not possess a suitable amino acid profile for PKU treatment. Thus, the treatment must be supplemented with amino acids like eg histidine, leucine, tryptophanand tyrosine, and, accordingly, the problems relating to taste and smell are not avoided.

The supplement with LNAA e.g. in the form of LNAA tablets as described above also suffers with bad taste and smell and, moreover, the dose is 1 tablet per 1 kg of body weight, which means that e.g. a 60 kg person must intake 60 tablets per day, i.e. 15 tablets 4 times daily or 20 tablets 3 times daily together with a meal. This will most likely also lead to compliance problems.

Enzyme Replacement Therapy

As described herein will enzyme replacement therapy with
i) PAH requires high-dose of BH-4, which is very expensive, and
ii) PAL requires a large dose as its activity is low.

BH4 Therapy

Studies have shown that most of the patients responsive to BH4 still need at least some restriction of natural protein and continued use of low-Phe medical food. Thus, the taste and smell problems are not totally overcome. Moreover, the costs are very high.

As seen from the above, the current treatment options for PKU all have some disadvantages. Accordingly, there is still a need to develop a treatment option of PKU that is without the need for supplement of bad-tasting and bad-smelling amino acids and that is much cheaper than the options relating to enzyme replacement therapy.

DESCRIPTION OF THE INVENTION

Proteins with no or low content of Phe have been suggested previously, e.g. in WO 2013/148332. Generally, the starting points have been to find suitable peptides or proteins, but these peptides or proteins may be hard to produce at a reasonable price for a PKU patient. The concept of providing proteins or peptides with no or low Phe for PKU patients was proposed a decade ago, but it is hard to make such product at a reasonable price. A PKU patient averagely needs 70 gram of proteins per day, and perhaps for dozens of years. The cheapest protein drug on market is about 1000 USD per gram. Based on the present invention, it should be possible to obtain a marked reduction in price due to the selection of i) expression system, ii) vector, and iii) starting proteins and possible mutations thereof. Thus, the aim is to enable production of a protein for a PKU patient at a reasonable cost and to avoid or reduce bad smell and bad taste.

The present invention involves i) selection of an expression system that enables an easy and cheap purification step, ii) selection of a suitable starting protein that has a relatively low content of Phe, iii) modifying the selected proteins to eliminate, alternatively reduce, the content of Phe and/or exchange amino acids to obtain desirable amino acid compositions including increasing amount of LNAA, iv) transferring the gene for the selected protein into a vector, and transforming the selected expression system with the vector.

When the expression system(s) is/are selected the task is to select proteins with no or low Phe (or replicable with Tyr or others), extracellular expression at high level, and digestible once heat-denatured, as the first generation of product. In addition, the protein should have all or most of essential amino acids and has better contain high content of Tyr and or Trp. The second step is then to alter these starting proteins to obtain second generation of proteins, see below.

Thus, the present invention provides recombinant proteins that do not contain any Phe or only contain a small number of Phe. As the first generation of protein it should have all or most of essential amino acids and has a high content of Tyr and or Trp. For the second generation, it should have all benefits of the first generation, but it should also contain ideal amino acid compositions, such as high content of Tyr, Leu, and other LNAA including Val, Ile, Trp, Met, etc.

Adding eg gliadin-like Gln-streches to a synthetic Phe-free protein may also lead to better structure and texture.

First, medical food benefits all PKU patients; secondly, recombinant proteins do not have bad taste and smell, and it will increase patient compliance; thirdly, if rich LNAA is incorporated into recombinant proteins, PKU patient diet may allow the inclusion of regular bread, rice, pasta, and other grains eliminating the need to purchase costly low protein foods.

An adult usually needs intake of 60-80 g protein per day. All the patients with PKU must control their Phe diet for all the life. One PKU patient usually consumes US $15,000 to $20,000 per year in medical foods. The difficulty of the PKU diet reflects its highly restrictive nature, as well as the requirement to consume a Phe-free amino acid (AA) formula every day to meet protein needs. The taste and smell of the AA formulas can be offensive; new dietary options are needed to improve the acceptability and variety of the low-Phe diet. GMP (glycomacropeptide) has functional properties suitable for making low-Phe foods and can be made into a variety of highly palatable products high in protein but low in Phe. but the drawback of this treatment is that it cannot completely replace the need for supplemental protein substitute because natural GMP (64 aa) does not include other amino acids such as tyrosine and tryptophan. In addition, the purification process of GMP is relative complicated and expensive. Therefore, looking for the substitutes including the low-Phe or Phe-free recombinant proteins with balanced amino acid composition will provide an alternative to synthetic AA-based formulas and GMP formulas. Moreover, a high-level expression system and an inexpensive purification process will effectively reduce the total cost of this medical food.

Expressions Systems for Use According to the Invention

The present invention also relates to recombinant host cells, comprising a polynucleotide encoding a protein of the present invention operably linked to one or more control sequences. A construct or vector comprising a polynucleotide is introduced into a host cell so that the construct or vector is maintained as a chromosomal integrant or as a self-replicating extra-chromosomal vector. The term "host cell" encompasses any progeny of a parent cell that is not identical to the parent cell due to mutations that occur during replication. The choice of host cell will to a large extent depend upon the gene encoding the protein and its source.

The host cell may be any cell useful in the recombinant production of a Phe-free protein or a protein with low content of Phe, e.g. a prokaryote or a eukaryote.

The prokaryotic host cell may be a bacterium such as *Bacillus subtilis, Bacillus licheniformis* or *E. coli* or other high expression prokaryotic systems. Presently *Bacillus subtilis* or *Bacillus licheniformis* is preferred.

The eukaryotic host cell may be a mammalian, insect, plant or fungal cell. The fungal cell may be a yeast cell. Suitable examples are *Pichia pastoris* X-33, GS115, *Yarrowia lipolytica, Lactuca sativa* L., *Pisum sativum*, and *Nicotiana benthamiana*.

The exogenous antibiotic genes from the genome of the host cell may be identified and deleted before use of the host cell. Moreover, the genes for formation of spores may also be knockout before use.

Selection of Expression System

It is important to use an expression system that can produce a recombinant protein at a high level and the system should be GRAS (generally regarded as safe).

We first considered a GRAS organism as an expression system to reduce the cost for purification step. Among all GRAS microorganisms, *Bacillus subtilis* and *Bacillus licheniformis* are two cheapest ones to grow due to their fast growth rate and cheap culture medium. As seen from the examples herein, these systems are suitable expressions systems to provide proteins with low or no content of Phe.

A great number of natural and recombinant proteins could be produced at a high level by various expression systems [41], including *E. coli, Bacillus*, other bacteria, Yeasts (*Saccharomyces cerevisiae* and *Pichia pastoris*), filamentous fungi, insect and mammalian cells. As table 1 shows, several recombinant proteins expressed in yeast, *Aspergillus niger* and *Trichoderma reesei* can reach up to 10 g/L. Mycoprotein derived from the fungus *Fusarium venenatum* has been used in foods for many years[42]. Mycoprotein produced by the Quorn Company offers many foods that use mycoprotein as a meat substitute. Most people can tolerate mycoprotein.

TABLE 1

Examples of expression recombinant secretory proteins using different production systems

| Protein | System | Production level | Refs |
|---|---|---|---|
| Levan fructotransferase | *E. coli* | 5.5 g/L | Mergulhao[43] |
| Human epidermal growth factor | *Bacillus brevis* | 3 g/L | Ebisu[44] |

TABLE 1-continued

Examples of expression recombinant secretory
proteins using different production systems

| Protein | System | Production level | Refs |
|---|---|---|---|
| TNF-alpha | *Pseudomonas fluorescens* | 4 g/L | Squires[45] |
| glucose oxidase | *S. cerevisiae* | 9 g/L | Park[46] |
| Human serum albumin | *S. cerevisiae* | 3 g/L | Schmidt[47] |
| Human serum albumin | *Pichia pastoris* | 10 g/L | Kobayashi[48] |
| phytase | *Pichia pastoris* | 13 g/L | Xiong[49] |
| gelatins | *Pichia pastoris* | 14.8 g/L | Werten[50] |
| phytase | *Hansenula polymorpha.* | 13.5 g/L | Mayer[51] |
| glucoamylase | *Aspergillus niger* | 25 g/L | Ward[52] |
| cellulase | *Trichoderma reesei* | 35 g/L | Durand[53] |

*Bacillus subtilis* and *Bacillus licheniformis* are Selected as Expression Hosts Although many protein expression systems are alternatives, microbial expression systems are the commonly used recombinant protein expression system. The recombinant Phe-free protein of the present invention will be used as medical food, so selection of a Generally Recognized As Safe (GRAS) microbial expression system to expression recombinant proteins is preferred. *Saccharomyces cerevisiae*, *Bacillus* and *Aspergillus niger* are the commonly used GRAS microbial expression system. However, secretory expression protein in *Saccharomyces cerevisiae* and *Aspergillus niger* has some disadvantages, such as long culture time (4-8 days), low protein productivity, genetic operation is more complex than prokaryotic organism and high production cost.

The Gram-positive *Bacillus* strains, particularly *B. subtilis*, *B. megaterium* and *B. licheniformis* designated as GRAS organisms, are free of any endotoxin and have short culture time compared with *E. coli*. Moreover, *B. subtilis*, *B. megaterium* and *B. licheniformis* offer high biosynthetic capacity and an efficient secretion apparatus that guides the expressed proteins directly into the culture supernatant.

Thus, in the present context the focus is on developing the two *B. subtilis* and *B. licheniformis* protein expression system. Relative more information concerning transcription, translation, protein folding and secretion mechanisms, genetic manipulation and large-scale fermentation of *B. subtilis* is available. The excellent protein secretion capacities of *B. licheniformis* have made it an attractive host for the large-scale production of commercially employed enzymes as well.

As demonstrated in the examples herein suitable expression systems are *B. subtilis*, notably *B. subtilis* strain WB800N, which is an eight-extracellular-protease deficient strain) and *B. licheniformis*. Other preferred strains are *B. subtilis* CICC10073 and *C. licheniformis* CIC1026 as it also appears from the examples herein.

Screening and Finding a Good Strain

Similar to human, different individual has significant different ability to handle a certain thing, different strains of *B. subtilis* and *B. licheniformis* have different ability to produce a target protein of the present invention. Therefore, screening and finding a good strain is an important step to lower the manufacturing cost of this product.

A good strain should meet the following three requirements:
  (1) Easy to grow in cheap and simple medium;
  (2) High level of protein expression and secretion;
  (3) Easy for gene operation and having high transformation efficiency.

The requirements (1) and (2) related to manufacturing cost are obvious key factors. Requirement (3) is important as the provision of the recombinant Phe-free proteins according to the invention involves genetic operation to incorporate target protein gene into the selected strain and to improve the strain protein expression and secretion properties. However, the improvement of *B. subtilis* and *B. licheniformis* strains has been hampered like many other *Bacillus* strains by the lack of or low transformation efficiencies (≤$10^3$ transformants/μg DNA). The genetic transformation of *B. licheniformis* is more difficult than *B. subtilis*. The transformation efficiency of the natural *B. licheniformis* cells is poor and it routinely needs long period of time with difficulty to finally obtain a desired transformant. This is mainly due to the existence of two types I restriction modification systems (RMS) in *B. licheniformis*. Since many genetic operation steps are involved in order to achieve a desired recombinant Phe-free protein, a strain with relatively high transformation efficiency is the key to shorten research and development time. The inventors will screen stains from natural sources and storage centers to find strains with nature high transformation efficiencies. Meanwhile, we will use genetic modification methods to improve transformation efficiencies of the *B. subtilis* and *B. licheniformis* strains with clear genetic background.

As mentioned above, *Bacillus subtilis* WB800N is a potential strain, but other strains are also suitable such as *B. subtilis* CICC10073 and *C. licheniformis* CIC1026 as demonstrated in the examples herein. For examples, some *Bacillus subtilis* and *Bacillus licheniformis* strains can produce alkali protease or alpha-amylase at very high levels. These genes can be replaced with the Phe-free or Phe-low genes to produce the proteins of the present invention, most likely at high production level.

Screening and Finding a Good Starting Protein

The recombinant Phe-free protein or protein with low content of Phe produced will be used as medical food for PKU patients, so integration of target gene into the genome of *B. subtilis* and *B. licheniformis* to get rid of free plasmids will be used for food safety consideration.

The recombinant Phe-free protein for PKU should
  i) contain no or low Phe,
  ii) have balanced content of other essential 19 amino acids,
  iii) preferably be rich in content of LNAA,
  iv) be manufactured non-expensively (high expression with simple purification process).

The general approaches are:
  (1) Select one or several proteins from highly expressed proteins expressed in GRAS microorganisms and a GRAS strain;
  (2) Modify the selected proteins to eliminate Phe and exchange amino acids to obtain desirable amino acid compositions including increasing the amount of LNAA;
  (3) Simplify purification process: incorporation of purification tags such as elastin-like polypeptide, which solubility is dramatically affected by temperature. Thus, isolation of the protein product can be simply done by heating the culture to 35-60° C., and/or deleting main extracellular proteins to reduce impurities;
  (4) Remove antibiotic genes and spore formation genes if necessary to make a very safe production strain.

Details appear from the examples herein.

In order to identify proteins with low Phe, high expression level and secreted into the culture, hundreds of proteins from

*B. subtilis*, *B. licheniformis* and *B. megaterium* genome databases are analyzed, particularly the proteins with high secretion levels naturally in *Bacillus* strains, such as α-amylase, protease including alkaline protease, serine alkaline protease, cellulase and xylanase, lipase. In particular serine alkaline protease and alkaline protease seem to be suitable for use, cf the examples herein.

The key issue is to identify naturally occurring proteins as starting point for making Phe-free proteins. The naturally occurring proteins must be non-toxic. Moreover, it should be relatively easy to produce the proteins in a microorganism and the microorganism should enable production with a relatively high yield. To this end the present inventors have found that especially *B. subtilis* and *B. licheniformis* have genes encoding proteins that have a suitable low content of Phe to be starting points for recombinant Phe-free proteins of the present invention.

In table 2 herein is given an overview of the proteins used as starting points SEQ ID NOs 1-14); their corresponding nucleic acids have SEQ ID NOs 59-73.

TABLE 2

Proteins selected for recombinant expression in *B. subtilis* and *B. licheniformis*.

| Abbreviation | Full name | Number of amino acids | Number of Phe | Sequence ID NO* |
|---|---|---|---|---|
| ΔPro1 | minor extracellular protease epr region 135-358 | 224 | 3 | No. 1 |
| ΔPro2 | minor extracellular protease vpr region 180-362 | 183 | 3 | No. 2 |
| ΔamyQ | alpha-amylase region 59-239 | 181 | 6 | No. 3 |
| ΔyjeA | secreted deoxyriboendonuclease region 274-461 | 188 | 3 | No. 4 |
| estA | secreted alkaliphilic lipase | 181 | 4 | No. 5 |
| estB | secreted esterase/lipase | 182 | 3 | No. 6 |
| aprE | serine alkaline protease | 275 | 3 | No. 7 |
| amyE | alpha-amylase | 618 | 22 | No. 8 |
| amyL | alpha-amylase | 483 | 20 | No. 9 |
| nprE | extracellular neutral metalloprotease | 301 | 9 | No. 10 |
| ALAB | human alpha-lactalbumin | 123 | 4 | No. 11 |
| Blapr | alkaline protease | 274 | 3 | No. 12 |
| lip | lipase | 174 | 3 | No. 13 |
| EGFP | Enhanced Green Fluorescent Portein | 239 | 13 | No. 14 |
| 10266apr | Alkaline protease | 274 | 4 | No. 74 |

The Phe group(s) of SEQ ID NOs 1-14 may be deleted or replaced with (an)other essential amino acid(s), notably with a LNAA such as Tyr, Trp, Thr, Ile, Leu, Val, Met and His, notably as demonstrated in the experiments reported herein Tyr, Lys, Cys, Met, Val.

One or more of the other amino acids in the proteins may also be deleted or replaced with another amino acid in order to obtain a recombinant protein with a composition of amino acid that is optimized for nutritive purpose.

Thus, one or more of small amino acids (Ala, Gly, and Ser) in the proteins may also be deleted or replaced with LNAA (Tyr, Trp, and Met).

Examples of recombinant Phe-free or Phe-low proteins are those of SEQ ID NOs 1-14, where the Phe groups have been replaced with other LNAAs such as Tyr, Trp, Thr, Ile, Leu, Val, Met and His, notably as demonstrated in the experiments reported herein Tyr, Lys, Cys, Met, Val. Other examples are Phe-free proteins 10266apr-W4 (SEQ ID NO 76) and 10073aprE-W7 (SEQ ID NO 80).

The best constitution of amino acids of Phe-free proteins have all essential amino acids and the content of LNAAs are as high as possible, particularly, Tyr content is as high as possible. For an example, the content of LNAAs is up to 80% and Tyr is up to 40%. As seen from the examples herein and SEQ ID 76 and SEQ ID NO 80 the content of LNAAs may be 30% or more such as in a range of from 30%-40% (based on number of amino acids); the content of Tyr may be 4% or more such as from 4-10% (based on the number of amino acids).

The length of recombinant Phe-free proteins may be 40-300 amino acids, but these proteins should be well digested by pepsin, tyrosinase and other proteases in human gastrointestinal track to release all amino acids for absorption as nutrients.

A further example is the anti-microbial peptide from *Bacillus subtilis* (PDB code 2B9K) SEQ ID NO 25. This peptide contains 21% aromatic (F, Y and W), 21% aliphatic plus M (I, L, V, M), and 15% positive charged (H, K, R) amino acids, an amino acid composition closer to the composition of NeoPhe. All 3 Phe will be replaced with Tyr or Trp or Leu, and other mutations may be introduced as well to make it well digestible in human gastrointestinal track. The peptide may be expressed with other peptides, proteins or itself together to increase protein size and improve amino acid compositions.

Another example is enhanced green fluorescent protein (EGFP), SEQ ID NO 14. This protein contains 10% aromatic (F, Y and W), 31% aliphatic plus M and T (I, L, V, M, T), and 15% positive charged (H, K, R) amino acids, an amino acid composition closer to the composition of NeoPhe. All Phe will be replaced with Tyr or Trp or Leu, and other mutations may be introduced as well to make it well digestible in human gastrointestinal track and further increase the contents of Tyr and Leu. This protein can be expressed with a high level by *Bacillus subtilis*.

For more examples, see Table 4 and the examples herein.

A starting protein is suitable one of the proteins mentioned herein (see eg above and Table 2) after introduction of high content of Tyr and Trp, which still can be expressed by *Bacillus subtilis* or *Bacillus licheniformis* at high level and it can be well digested in human gastrointestinal tract.

The starting proteins are mutated to obtain a desired composition of amino acids. The desired composition of amino acids varies for different Phe-free proteins. The first generation of protein is typically obtained by mutating of Phe to LNAAs. The second generation of proteins will be created from a candidate to contain high content of Tyr, Trp, Leu and other amino acids given in Table 3, in the column of NeoPhe. However, the protein must be expressed by *Bacillus subtilis* or *Bacillus licheniformis* at high level and it must be well digested in human gastrointestinal track. Some candidate examples are given in Table 4.

TABLE 3

Comparison of the amino acid compositions of the first generation product of maprE and the second generation products with amino acid composition close to Neo-Phe (LNAA)

| Amino acids: | First generation Number | First generation Percentage(%) | Second generation Number | Second generation (%) | NeoPhe (LNAA) (%) |
|---|---|---|---|---|---|
| Tyr | 14 | 5 | 28-56 | 10-20 | 32.5 |
| Trp | 3 | 1 | 12-18 | 4-6 | 8.5 |
| Met | 4 | 1 | 6-12 | 2-4 | 5.3 |
| Ile | 16 | 6 | 16 | 6 | 5.8 |

TABLE 3-continued

Comparison of the amino acid compositions of the first generation product of maprE and the second generation products with amino acid composition close to Neo-Phe (LNAA)

| Amino acids: | First generation Number | First generation Percentage(%) | Second generation Number | Second generation (%) | NeoPhe (LNAA) (%) |
|---|---|---|---|---|---|
| Thr | 19 | 7 | 19 | 7 | 5.3 |
| Val | 25 | 9 | 25 | 9 | 5.8 |
| Lue | 16 | 6 | 16 | 6 | 21.6 |
| His | 6 | 2 | 6 | 2 | 5 |
| Lys | 8 | 3 | 8 | 3 | 5 |
| Arg | 4 | 1 | 4 | 1 | 5 |
| Ala | 35 | 13 | 10-20 | 3-7 | 0 |
| Cys | 0 | 0 | 0 | 0 | 0 |
| Asp | 9 | 3 | 9 | 3 | 0 |
| Glu | 5 | 2 | 5 | 2 | 0 |
| Phe | 0 | 0 | 0 | 0 | 0 |
| Gly | 33 | 12 | 10-20 | 3-7 | 0 |
| Asn | 16 | 6 | 16 | 6 | 0 |
| Pro | 13 | 5 | 13 | 5 | 0 |
| Gln | 10 | 4 | 10 | 4 | 0 |
| Ser | 39 | 14 | 10-20 | 3-7 | 0 |

TABLE 4

Amino acid compositions (%) of the selected candidate proteins or their truncated forms

| Protein code (PDB) | 2KCK | 2B9K | 2LYX | 2KYZ | 3C0F | 2K1W | NeoPhe |
|---|---|---|---|---|---|---|---|
| Ala | 11.8 | 6.4 | 6.6 | 1.5 | 7.2 | 4.9 | — |
| Arg | 2.9 | 2.1 | 5.3 | 3.0 | 4.8 | 3.7 | 5 |
| Asn | 5.9 | 4.3 | 1.3 | 4.5 | 6.0 | 6.1 | — |
| Asp | 6.9 | 6.4 | 3.9 | 4.5 | 3.6 | 7.3 | — |
| Cys | 1.0 | 0 | 0 | 3.0 | 3.6 | 0.0 | — |
| Gln | 2.0 | 2.1 | 6.6 | 1.5 | 2.4 | 2.4 | — |
| Glu | 17.6 | 2.1 | 10.5 | 16.4 | 12.0 | 6.1 | — |
| Gly | 3.9 | 8.5 | 2.6 | 1.5 | 6.0 | 12.2 | — |
| His | 0.0 | 0 | 1.3 | 1.5 | 1.2 | 1.2 | 5 |
| Ile | 5.9 | 6.4 | 5.3 | 4.5 | 7.2 | 8.5 | 5.8 |
| Leu | 8.8 | 4.3 | 6.6 | 9.0 | 6.0 | 2.4 | 21.6 |
| Lys | 7.8 | 12.8 | 15.8 | 10.4 | 8.4 | 4.9 | 5 |
| Met | 1.0 | 0 | 1.3 | 3.0 | 1.2 | 0.0 | 5.3 |
| Phe | 1.0 | 6.4 | 5.3 | 0.0 | 3.6 | 4.9 | — |
| Pro | 2.0 | 2.1 | 2.6 | 3.0 | 2.4 | 3.7 | — |
| Ser | 2.0 | 10.6 | 5.3 | 7.5 | 6.0 | 13.4 | — |
| Thr | 1.0 | 2.1 | 2.6 | 1.5 | 1.2 | 2.4 | 5.3 |
| Trp | 2.0 | 6.4 | 2.6 | 0.0 | 1.2 | 2.4 | 8.5 |
| Tyr | 10.8 | 8.5 | 5.3 | 7.5 | 7.2 | 7.3 | 32.5 |
| Val | 5.9 | 8.5 | 9.2 | 16.4 | 8.4 | 6.1 | 5.8 |
| Truncated number | 5-106 | 1-47 | 12-87 | 1-67 | 3-86 | 4-85 | |

In the examples herein is given examples of mutated proteins prepared based on the selected proteins identified in Table 2.

The amino acid sequences for the mutated proteins prepared are shown in the following with indication relating to mutations.

```
SEQ ID NO 26: Mutated protein of SEQ ID NO 7: aprE50Y189Y261L
AQSVPYGISQIKAPALHSQGYTGSNVKVAVIDSGIDSSHPDLNVRGGASYVP-
SETNPYQDGSSHGTHVAGTIAALNNSIGVLGVAPSASLYAVKVLDSTGSGQYSWI-
INGIEWAISNNMDVINMSLGGPTGSTALKTVVDKAVSSGIVVAAAA-
GNEGSSGSTSTVGYPAKYPSTIAVGAVNSSNQRASYSSAGSEL-
DVMAPGVSIQSTLPGGTYGAYNGTSMATPHVAGAAALILSKHPTWTNAQVRDRLES-
TATYLGNSLYYGKGLINVQAAAQ SEQ ID NO 27: Mutated protein of SEQ ID NO 7: aprE50Y189Y261LCC
AQSVPYGISQIKAPALHSQGYTGSNVKVAVIDSGIDSSHPDLNVRGGASYVP-
SETNPYQDGSSHGTHVAGTIAALNNSIGVLGVAPSASLYAVKVLDSTGSGQYSWI-
INGIEWAISNNMDVINMSLGGPTGSTALKTVVDKAVSSGIVVAAAA-
GNEGSSGSTSTVGYPAKYPSTIAVGAVNSSNQRASYSSAGSEL-
DVMAPGVSIQSTLPGGTYGAYNGTSMATPHVAGAAALILSKHPTWTNAQVRDRLES-
TATYLGNSLYYGKGLINVQAAAQCC SEQ ID NO 28: Mutated protein of SEQ ID NO 12: Blapr58Y188Y260W
AQTVPYGIPLIKADKVQAQGYKGANVKVAVLDTGIQASHPDLNVVGGASYV-
AGEAYNTDGNGHGTHVAGTVAALDNTTGVLGVAPNVSLYAVKVLNSSGSGSYS-
GIVSGIEWATTNGMDVINMSLGGPSGSTAMKQAVDNAYARGVVVVAAA-
GNSGSSGNTNTIGYPAKYDSVIAVGAVDSNSNRASYSSVGAELEVMAP-
GAGVYSTYPTSTYATLNGTSMASPHVAGAAALILSKHPNLSASQVRNRLSSTATYL-
GSSWYYGKGLINVEAAAQ
```

SEQ ID NO 29: Mutated protein of SEQ ID NO 12: Blapr58Y188Y260WCC
AQTVPYGIPLIKADKVQAQGYKGANVKVAVLDTGIQASHPDLNVVGGASYV-

AGEAYNTDGNHGTHVAGTVAALDNTTGVLGVAPNVSLYAVKVLNSSGSGSYS-

GIVSGIEWATTNGMDVINMSLGGPSGSTAMKQAVDNAYARGVVVVAAA-

GNSGSSGNTNTIGYPAKYDSVIAVGAVDSNSNRASYSSVGAELEVMAP-

GAGVYSTYPTSTYATLNGTSMASPHVAGAAALILSKHPNLSASQVRNRLSSTATYL-

GSSWYYGKGLINVEAAAQCC

SEQ ID NO 30: Mutated protein of SEQ ID NO 12: Blapr58C188Y260W
AQTVPYGIPLIKADKVQAQGYKGANVKVAVLDTGIQASHPDLNVVG-

GASCVAGEAYNTDGNHGTHVAGTVAALDNTTGVLGVAP-

NVSLYAVKVLNSSGSGSYSGIVSGIEWATTNGMDVINMSLGGPSGSTAMKQAVDNA-

YARGVVVVAAAGNSGSSGNTNTIGYPAKYDSVIAVGAVDSNSNRA-

SYSSVGAELEVMAPGAGVYSTYPTSTYATLNGTSMASPHVAGAAALILSKHPNL-

SASQVRNRLSSTATYLGSSWYYGKGLINVEAAAQ

SEQ ID NO 31: Mutated protein of SEQ ID NO 5: estA17Y19Y41C58Y
AEHNPVVMVHGIGGASYNYAGIKSYLVSQGWSRD-

KLYAVDCWDKTGTNYNNGPVLSRYVQKVLDETGAKKVDIVAHSMGGANTLYYIKNLD-

GGNKVANVVTLGGANRLTTGKALPGTDPNQKILYTSIYSSADMIVMNYLSRLD-

GARNVQIHGVGHIGLLYSSQVNSLIKEGLNGGGQNTN

SEQ ID NO 32: Mutated protein of SEQ ID NO 5: estA17W19Y41C58Y
AEHNPVVMVHGIGGASWNYAGIKSYLVSQGWSRD-

KLYAVDCWDKTGTNYNNGPVLSRYVQKVLDETGAKKVDIVAHSMGGANTLYYIKNLD-

GGNKVANVVTLGGANRLTTGKALPGTDPNQKILYTSIYSSADMIVMNYLSRLD-

GARNVQIHGVGHIGLLYSSQVNSLIKEGLNGGGQNTN

SEQ ID NO 33: Mutated protein of SEQ ID NO 6: estB20Y21M40C
ESVHNPVVLVHGISGASYNYMAIKNYLISQGWQSNKLYAIDCYDKTGNNLNNGPQLA-

SYVDRVLKETGAKKVDIVAHSMGGANTLYYIKYLGGGNKIQNVVTLG-

GANGLVSSTALPGTDPNQKILYTSIYSLNDQIVINSLSRLQGARNIQLYGIGHIGLLSNS-

QVNGYIKEGLNGGGLNTN

SEQ ID NO 34: Mutated protein of SEQ ID NO 11: ALAB-V4
KQVTKCELSQLLKDIDGYGGIALPELICTMVHTSGYDTQAIVENNESTEY-

GLVQISNKLWCKSSQVPQSRNICDISCDKVLDDDITDDIMCAKKILDIKGIDYW-

LAHKALCTEKLEQWLCEKL

SEQ ID NO 35: Mutated protein of SEQ ID NO 11: ALAB-M1V3
KQMTKCELSQLLKDIDGYGGIALPELICTMVHTSGYDTQAIVENNESTEY-

GLVQISNKLWCKSSQVPQSRNICDISCDKVLDDDITDDIMCAKKILDIKGIDYW-

LAHKALCTEKLEQWLCEKL

SEQ ID NO 36: Mutated protein of SEQ ID NO 11: ALAB-Y1V3
KQMTKCELSQLLKDIDGYGGIALPELICTMVHTSGYDTQAIVENNESTEY-

GLVQISNKLWCKSSQVPQSRNICDISCDKVLDDDITDDIMCAKKILDIKGIDYW-

LAHKALCTEKLEQWLCEKL

SEQ ID NO 37: Mutated protein of SEQ ID NO 11: ALAB-H1V3
KQHTKCELSQLLKDIDGYGGIALPELICTMVHTSGYDTQAIVENNESTEY-

GLVQISNKLWCKSSQVPQSRNICDISCDKVLDDDITDDIMCAKKILDIKGIDYW-

LAHKALCTEKLEQWLCEKL

In order to achieve a good Phe-free protein, the proteins identified as starting proteins will be modified after the following principles in order to keep the structure of target proteins undisturbed when replacing Phe with LNAAs. For examples,
(1) If a Phe in alpha helix region, the Phe could be replaced with Lys, Trp, Ile, Val, Met and Leu
(2) If a Phe in the marginal area of alpha helix, the Phe could be replaced with His, Cys, Thr, Arg and Tyr.
(3) If a Phe in a loop area, the Phe could be replaced with Tyr.
(4) Some proteins may not have the Cys residues, the Phe could be replaced with Cys when the Phe in the marginal area of alpha helix or loop area.
(5) Expression to test the Phe-free protein in *Bacillus* system. The expression level of Phe-free protein should be close to or higher than the native protein.

The invention also provides isolated nucleic acids encoding the Phe-free or Phe-low proteins of the invention. In the following the sequences are given:

```
SEQ ID NO 38. aprE50Y189Y261L gene sequence: signal peptide (marked
green and italic)+ Pro-peptide (marked red and underlined) +mature
peptide. The mutation sites are marked with in bold and yellow.
GTGAGAAGCAAAAAATTGTGGATCAGCTTGTTGTTTGCGTTAACGTTAATCTTTAC-

GATGGCGTTCAGCAACATGTCTGCGCAGGCTGCCGGAAAAAGCAGTACAGAAAAG

AAATACATTGTCGGATTTAAACAGACAATGAGTGCCATGAGTTCCGCCAA-

GAAAAAGGATGTTATTTCTGAAAAAGGCGGAAAGGTTCAAAAGCAATTTAAGTATGT

TAACGCGGCCGCAGCAACATTGGATGAAAAAGCTGTAAAAGAATTGAAAAAA-

GATCCGAGCGTTGCATATGTGGAAGAAGATCATATTGCACATGAATATGCGCAATCT

GTTCCTTATGGCATTTCTCAAATTAAAGCGCCGGCTCTTCACTCTCAAGGC-

TACACAGGCTCTAACGTAAAAGTAGCTGTTATCGACAGCGGAATTGACTCTTCTCAT

CCTGACTTAAACGTCAGAGGCGGAGCAAGCTACGTAC-

CTTCTGAAACAAACCCATACCAG-

GACGGCAGTTCTCACGGTACGCATGTAGCCGGTACGATTGCCGCTCTTAATAACTC

AATCGGTGTTCTGGGCGTAGCGCCAAGCGCATCATTATATGCAGTAAAAGTGCTT-

GAT-

TCAACAGGAAGCGGCCAATATAGCTGGATTATTAACGGCATTGAGTGGGCCATTTC

CAACAATATGGATGTTATCAACATGAGCCTTGGCGGACCTACTGGTTC-

TACAGCGCTGAAAACAGTCGTTGACAAAGCCGTTTCCAGCGGTATCGTCGTTGCT

GCCGCAGCCGGAAACGAAGGTTCATCCGGAAGCACAAGCACAGTCGGC-

TACCCTGCAAAA-

TATCCTTCTACTATTGCAGTAGGTGCGGTAAACAGCAGCAACCAAAGAGCTTCATA

CTCCAGCGCAGGTTCTGAGCTTGATGTGATGGCTCCTGGCGTGTCCATCCAAA-

GCACAC-

TTCCTGGAGGCACTTACGGCGCTTATAACGGAACGTCCATGGCGACTCCTCACGT

TGCCGGAGCAGCAGCGTTAATTCTTTCTAAGCACCCGACTTGGACAAACGCG-

CAAGTCCGTGATCGTTTAGAAAGCACTGCAACATATCTTGGAAACTCTCTCTACTAT

GGAAAAGGGTTAATCAACGTACAAGCAGCTGCACAATAA

SEQ ID NO 39. aprE50Y189Y261LCC gene sequence (signal peptide+
Pro-peptide +mature peptide)
GTGAGAAGCAAAAAATTGTGGATCAGCTTGTTGTTTGCGTTAACGTTAATCTTTAC-

GATGGCGTTCAGCAACATGTCTGCGCAGGCTGCCGGAAAAAGCAGTACAGAAAAG

AAATACATTGTCGGATTTAAACAGACAATGAGTGCCATGAGTTCCGCCAA-

GAAAAAGGATGTTATTTCTGAAAAAGGCGGAAAGGTTCAAAAGCAATTTAAGTATGT

TAACGCGGCCGCAGCAACATTGGATGAAAAAGCTGTAAAAGAATTGAAAAAA-

GATCCGAGCGTTGCATATGTGGAAGAAGATCATATTGCACATGAATATGCGCAATCT
```

GTTCCTTATGGCATTTCTCAAATTAAAGCGCCGGCTCTTCACTCTCAAGGC-

TACACAGGCTCTAACGTAAAAGTAGCTGTTATCGACAGCGGAATTGACTCTTCTCAT

CCTGACTTAAACGTCAGAGGCGGAGCAAGCTACGTAC-

CTTCTGAAACAAACCCATACCAG-

GACGGCAGTTCTCACGGTACGCATGTAGCCGGTACGATTGCCGCTCTTAATAACTC

AATCGGTGTTCTGGGCGTAGCGCCAAGCGCATCATTATATGCAGTAAAAGTGCTT-

GAT-

TCAACAGGAAGCGGCCAATATAGCTGGATTATTAACGGCATTGAGTGGGCCATTTC

CAACAATATGGATGTTATCAACATGAGCCTTGGCGGACCTACTGGTTC-

TACAGCGCTGAAAACAGTCGTTGACAAAGCCGTTTCCAGCGGTATCGTCGTTGCT

GCCGCAGCCGGAAACGAAGGTTCATCCGGAAGCACAAGCACAGTCGGC-

TACCCTGCAAAA-

TATCCTTCTACTATTGCAGTAGGTGCGGTAAACAGCAGCAACCAAAGAGCTTCATA

CTCCAGCGCAGGTTCTGAGCTTGATGTGATGGCTCCTGGCGTGTCCATCCAAA-

GCACAC-

TTCCTGGAGGCACTTACGGCGCTTATAACGGAACGTCCATGGCGACTCCTCACGT

TGCCGGAGCAGCAGCGTTAATTCTTTCTAAGCACCCGACTTGGACAAACGCG-

CAAGTCCGTGATCGTTTAGAAAGCACTGCAACATATCTTGGAAACTCTCTCTACTAT

GGAAAAGGGTTAATCAACGTACAAGCAGCTGCACAATGTTGCTAA

SEQ ID NO 40. Blapr58Y188Y260W gene sequence (signal peptide+
Pro-peptide +mature peptide)
*ATG**ATGAGGAAAAAGAGTTTTTGGCTTGGGATGCTGAC-*

*GGCCTTAATGCTCGTGTTCAC-*

*GATGGCCTTCAGCGATTCCGCGTCTGCTGCT*<u>CAGCCGGCGAAAAATGTTGAAAAG</u>

<u>GATTATATTGTCGGATTTAAGTCGGGAGTGAAAACCG-</u>

<u>CATCCGTCAAAAAGGACATCATCAAAGAGAGCGGCGGAAAAGTGGACAAGCAGTT</u>

<u>TAGAATCATCAACGCGGCAAAAGCGAAGCTAGACAAAGAAGCGCTTGAG-</u>

<u>GAAGTCAAAAATGATCCGGATGTCGCTTATGTGGAAGAGGATCACGTAGCTCATGC</u>

<u>TTTGGCGCAAACCGTTCCTTACGGCATTCCTCTCATTAAAGCGGACAAAGTG</u>-

CAGGCTCAAGGCTACAAGGGAGCGAACGTAAAAGTCGCCGTCCTGGATACAGGAA

TCCAAGCTTCTCATCCGGACTTGAACGTAGTCGGCGGAGCAAGCTAC-

GTAGCTGGCGAA-

GCTTATAACACCGACGGCAACGGACACGGCACGCATGTTGCCGGTACAGTAGCTG

CGCTTGACAATACAACGGGTGTATTAGGCGTTGCGCCGAACGTATCCTTGTAC-

GCGGTTAAAGTGCTGAATTCAAGCGGAAGCGGATCTTACAGCGGCATTGTAAGCG

GAATCGAGTGGGCGACGACAAACGGCATGGATGTTATCAACATGAGCCTTGGAG-

GAC-

CATCAGGCTCAACAGCGATGAAACAGGCGGTTGACAATGCATATGCAAGAGGGGT

TGTCGTTGTGGCGGCTGCTGGGAACAGCGGATCTTCAGGAAACAC-

GAATACAATCGGC-

TATCCTGCGAAATACGACTCTGTCATCGCAGTTGGCGCGGTAGACTCTAACAGCAA

CAGAGCTTCATATTCCAGCGTCGGAGCAGAGCTTGAAGTCATGGCTCCTGGCG-

CAGGCGTG-

TACAGCACTTACCCAACCAGCACTTATGCAACATTGAACGGAACGTCAATGGCTTC

TCCTCATGTAGCGGGAGCAGCAGCTTTGATCTTGTCAAAACATCCGAAC-

CTTTCAGCTTCACAAGTCCGCAACCGTCTCTCCAGTACGGCGACTTATTTGGGAAG

CTCCTGGTACTATGGAAAAGGTCTGATCAATGTCGAAGCTGCCGCTCAATAA

SEQ ID NO 41. Blapr58Y188Y260WCC gene sequence (signal peptide+
Pro-peptide +mature peptide)
*ATG*ATGAGGAAAAAGAGTTTTTGGCTTGGGATGCTGAC-

*GGCCTTAATGCTCGTGTTCAC-*

*GATGGCCTTCAGCGATTCCGCGTCTGCTGCT*CAGCCGGCGAAAAATGTTGAAAAG

GATTATATTGTCGGATTTAAGTCGGGAGTGAAAACCG-

CATCCGTCAAAAAGGACATCATCAAAGAGAGCGGCGGAAAAGTGGACAAGCAGTT

TAGAATCATCAACGCGGCAAAAGCGAAGCTAGACAAAGAAGCGCTTGAG-

GAAGTCAAAAATGATCCGGATGTCGCTTATGTGGAAGAGGATCACGTAGCTCATGC

TTTGGCGCAAACCGTTCCTTACGGCATTCCTCTCATTAAAGCGGACAAAGTG-

CAGGCTCAAGGCTACAAGGGAGCGAACGTAAAAGTCGCCGTCCTGGATACAGGAA

TCCAAGCTTCTCATCCGGACTTGAACGTAGTCGGCGGAGCAAGCTAC-

GTAGCTGGCGAA-

GCTTATAACACCGACGGCAACGGACACGGCACGCATGTTGCCGGTACAGTAGCTG

CGCTTGACAATACAACGGGTGTATTAGGCGTTGCGCCGAACGTATCCTTGTAC-

GCGGTTAAAGTGCTGAATTCAAGCGGAAGCGGATCTTACAGCGGCATTGTAAGCG

GAATCGAGTGGGCGACGACAAACGGCATGGATGTTATCAACATGAGCCTTGGAG-

GAC-

CATCAGGCTCAACAGCGATGAAACAGGCGGTTGACAATGCATATGCAAGAGGGGT

TGTCGTTGTGGCGGCTGCTGGGAACAGCGGATCTTCAGGAAACAC-

GAATACAATCGGC-

TATCCTGCGAAATACGACTCTGTCATCGCAGTTGGCGCGGTAGACTCTAACAGCAA

CAGAGCTTCATATTCCAGCGTCGGAGCAGAGCTTGAAGTCATGGCTCCTGGCG-

CAGGCGTG-

TACAGCACTTACCCAACCAGCACTTATGCAACATTGAACGGAACGTCAATGGCTTC

TCCTCATGTAGCGGGAGCAGCAGCTTTGATCTTGTCAAAACATCCGAAC-

CTTTCAGCTTCACAAGTCCGCAACCGTCTCTCCAGTACGGCGACTTATTTGGGAAG

CTCCTGGTACTATGGAAAAGGTCTGATCAATGTCGAAGCTGCCGCTCAATGTT-

GCTAA

SEQ ID NO 42. Blapr58C188Y260W gene sequence (signal peptide+
Pro-peptide +mature peptide)
*ATG*ATGAGGAAAAAGAGTTTTTGGCTTGGGATGCTGAC-

*GGCCTTAATGCTCGTGTTCACGATGGCCTTCAGCGAT-*

*TCCGCGTCTGCTGCT*CAGCCGGCGAAAAATGTTGAAAAGGATTATATTGTCGGAT-

TAAGTCGGGAGTGAAAACCGCATCCGTCAAAAAGGACATCATCAAAGA-

GAGCGGCGGAAAAGTGGACAAGCAGTTTAGAATCATCAACGCGGCAAAAGCGAA-

GCTAGACAAAGAAGCGCTTGAGGAAGTCAAAAATGATCCGGATGTCGCTTATGTG-

GAAGAGGATCACGTAGCTCATGCTTTGGCGCAAACCGTTCCTTACGG-

CATTCCTCTCATTAAAGCGGACAAAGTGCAGGCTCAAGGCTACAAGGGAGCGAAC-

GTAAAAGTCGCCGTCCTGGATACAGGAATCCAAGCTTCTCATCCGGACTTGAAC-

GTAGTCGGCGGAGCAAGCTGCGTAGCTGGCGAAGCTTATAACACCGACGGCAAC-

GGACACGGCACGCATGTTGCCGGTACAGTAGCTGCGCTTGACAATACAAC-

GGGTGTATTAGGCGTTGCGCCGAACGTATCCTTGTAC-

GCGGTTAAAGTGCTGAATTCAAGCGGAAGCGGATCTTACAGCGGCATTGTAAGCG-

GAATCGAGTGGGCGACGACAAACGGCATGGATGTTATCAACATGAGCCTTGGAG-

GACCATCAGGCTCAACAGCGATGAAACAGGCGGTTGACAATGCATATGCAA-

GAGGGGTTGTCGTTGTGGCGGCTGCTGGGAACAGCGGATCTTCAGGAAACAC-

GAATACAATCGGCTATCCTGCGAAATACGACTCTGTCATCGCAGTTGGCGCGG-

TAGACTCTAACAGCAACAGAGCTTCATATTCCAGCGTCGGAGCAGAGCTT-

GAAGTCATGGCTCCTGGCGCAGGCGTGTACAGCACTTACCCAACCAGCAC-

TTATGCAACATTGAACGGAACGTCAATGGCTTCTCCTCATGTAGCGGGAGCAG-

CAGCTTTGATCTTGTCAAAACATCCGAACCTTTCAGCTTCACAAGTCCGCAAC-

CGTCTCTCCAGTACGGCGACTTATTTGGGAAGCTCCTGG-

TACTATGGAAAAGGTCTGATCAATGTCGAAGCTGCCGCTCAATAA

SEQ ID NO 43. estA17Y19Y41C58Y
GCTGAACACAATCCAGTCGTTATGGTTCACGGTATTGGAGGGGCATCATA-

CAATTATGCGGGAATTAAGAGCTATCTCGTATCTCAGGGCTGGTCGCGGGACAA-

GCTGTATGCAGTTGATTGTTGGGACAAGACAGGCACAAATTATAACAATGGACCGG-

TATTATCACGATATGTGCAAAAGGTTTTAGATGAAACGGGTGCGAAAAAAGTGGA-

TATTGTCGCTCACAGCATGGGGGGCGCGAACACACTTTACTACATAAAAAATCTG-

GACGGCGGAAATAAAGTTGCAAACGTCGTGACGCTTGGCGGCGCGAACCGTTT-

GACGACAGGCAAGGCGCTTCCGGGAACAGATCCAAATCAAAAGATTTTATA-

CACATCCATTTACAGCAGTGCCGATATGATTGTCATGAATTACTTATCAA-

GATTAGATGGTGCTAGAAACGTTCAAATCCATGGCGTTGGACACATCGGCCTTCTG-

TACAGCAGCCAAGTCAACAGCCTGATTAAAGAAGGGCTGAAC-

GGCGGGGGCCAGAATACGAATTAA

SEQ ID NO 44. estA17W19Y41C58Y
GCTGAACACAATCCAGTCGTTATGGTTCACGGTATTGGAGGGG-

CATCATGGAATTATGCGGGAATTAAGAGCTATCTCGTATCTCAGGGCTGGTCGCGG-

GACAAGCTGTATGCAGTTGATTGTTGGGACAAGA-

CAGGCACAAATTATAACAATGGACCGGTATTATCACGATATGTGCAAAAGGTTTTA-

GATGAAACGGGTGCGAAAAAAGTGGATATTGTCGCTCACAG-

CATGGGGGGCGCGAACACACTTTACTACATAAAAAATCTGGACGGCGGAAA-

TAAAGTTGCAAACGTCGTGACGCTTGGCGGCGCGAACCGTTTGAC-

GACAGGCAAGGCGCTTCCGGGAACAGATCCAAATCAAAAGATTTTATA-

CACATCCATTTACAGCAGTGCCGATATGATTGTCATGAATTACTTATCAA-

GATTAGATGGTGCTAGAAACGTTCAAATCCATGGCGTTGGACACATCGGCCTTCTG-

TACAGCAGCCAAGTCAACAGCCTGATTAAAGAAGGGCTGAAC-

GGCGGGGGCCAGAATACGAATTAA

SEQ ID NO 45. estB20Y21M40C
GAGTCAGTACATAATCCTGTCGTTCTTGTTCATGGAATAAGTGGTGCATCATACAAC-

TA-

TATGGCTATTAAAAACTACTTAATTTCTCAAGGCTGGCAAAGCAACAAACTGTACGC

AATTGATTGTTATGATAAAACAGGAAACAACCTAAATAACGGCCCGCAGCTT-

GCTTCAT-

ATGTTGACCGTGTTTTAAAAGAGACTGGGGCAAAAAAAGTAGATATTGTGGCTCATA

GTATGGGAGGCGCCAATACGCTGTACTATATTAAATATTTAGGCGGGGGCAATAA-

GAT-

TCAAAATGTCGTAACGCTTGGAGGGGCTAATGGTTTAGTGTCATCAACCGCGCTGC

CGGGCACAGACCCTAATCAAAAGATCCTCTATACATCTATTTACAG-

TCTCAATGATCAAATT-

GTCATCAATAGCTTGTCTCGGTTACAAGGAGCGCGAAACATCCAGCTTTATGGCAT

CGGTCATATTGGCTTGCTTTCTAATAGCCAAGTGAACGGCTATATCAAA-

GAAGGGCTGAATGGCGGAGGCCTCAATACAAATTAA

SEQ ID NO 46. ALAB-V4
AAGCAAGTCACAAAATGTGAGCTGTCCCAGCTGCTGAAAGACATA-

GATGGTTATGGAGGCATCGCTTTGCCTGAATTGATCTGTACCATGGTTCACACCAG-

TGGTTATGACACACAAGCCATAGTTGAAAACAATGAAAGCACGGAA-

TATGGACTCGTCCAGATCAGTAATAAGCTTTGGTGCAAGAG-

CAGCCAGGTCCCTCAGTCAAGGAACATCTGTGACATCTCCTGTGACAAGGTCCTG-

GATGATGACATTACTGATGACATAATGTGTGCCAAGAAGATCCTGGA-

TATTAAAGGAATTGACTACTGGTTGGCCCATAAAGCCCTCTGCACTGAGAAGCTG-

GAACAGTGGCTTTGTGAGAAGTTGTGA

SEQ ID NO 47. ALAB-M1V3
AAGCAAATGACAAAATGTGAGCTGTCCCAGCTGCTGAAAGACATA-

GATGGTTATGGAGGCATCGCTTTGCCTGAATTGATCTGTACCATGGTTCACACCAG-

TGGTTATGACACACAAGCCATAGTTGAAAACAATGAAAGCACGGAA-

TATGGACTCGTCCAGATCAGTAATAAGCTTTGGTGCAAGAG-

CAGCCAGGTCCCTCAGTCAAGGAACATCTGTGACATCTCCTGTGACAAGGTCCTG-

GATGATGACATTACTGATGACATAATGTGTGCCAAGAAGATCCTGGA-

TATTAAAGGAATTGACTACTGGTTGGCCCATAAAGCCCTCTGCACTGAGAAGCTG-

GAACAGTGGCTTTGTGAGAAGTTGTGA

SEQ ID NO 48. ALAB-Y1V3
AAGCAATATACAAAATGTGAGCTGTCCCAGCTGCTGAAAGACATA-

GATGGTTATGGAGGCATCGCTTTGCCTGAATTGATCTGTACCATGGTTCACACCAG

TGGTTATGACACACAAGCCATAGTTGAAAACAATGAAAGCACGGAA-

TATGGACTCGTCCAGATCAGTAATAAGCTTTGGTGCAAGAGCAGCCAGGTCCCTCA

GTCAAGGAACATCTGTGACATCTCCTGTGACAAGGTCCTG-

GATGATGACATTACTGATGACATAATGTGTGCCAAGAAGATCCTGGATATTAAAGGA

ATTGACTACTGGTTGGCCCATAAAGCCCTCTGCACTGAGAAGCTGGAACAG-

TGGCTTTGTGAGAAGTTGTGA

-continued

SEQ ID NO 49. ALAB-H1V3
AAGCAACATACAAAATGTGAGCTGTCCCAGCTGCTGAAAGACATA-

GATGGTTATGGAGGCATCGCTTTGCCTGAATTGATCTGTACCATGGTTCACACCAG-

TGGTTATGACACACAAGCCATAGTTGAAAACAATGAAAGCACGGAA-

TATGGACTCGTCCAGATCAGTAATAAGCTTTGGTGCAAGAG-

CAGCCAGGTCCCTCAGTCAAGGAACATCTGTGACATCTCCTGTGACAAGGTCCTG-

GATGATGACATTACTGATGACATAATGTGTGCCAAGAAGATCCTGGA-

TATTAAAGGAATTGACTACTGGTTGGCCCATAAAGCCCTCTGCACTGAGAAGCTG-

GAACAGTGGCTTTGTGAGAAGTTGTGA

The nucleotides may be from genomic DNA, cDNA, sense RNA and anti-sense RNA.

Expression Vectors

A good *Bacillus* secretory expression vectors should include the following gene elements:
(1) strong promoter,
(2) suitable signal peptide,
(3) multiple cloning site (MCS),
(4) stable and high-copy replicon and antibiotic resistance gene.

The present invention also relates to recombinant expression vectors comprising a polynucleotide encoding a protein of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the protein at such sites. Alternatively, the polynucleotide may be expressed by inserting the polynucleotide in a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g. a plasmid or virus) that can be conveniently subjected to recombinant DNA procedures and can bring about expression of the polynucleotide. The choice of vector will typically depend on the compatibility of the vector with the host cell into which the vector is to be introduced. The vector may be a linear or closed circular plasmid.

As demonstrated in the examples herein suitable expression vectors are pHT01 and pHT43 (SEQ ID NOs 15 and 16, respectively) as well as mutants thereof, pHT100, pHT223 and pHT250 (mutants of pHT01) and pHT431, pHT432 and pHT433 (mutants of pHT43); see SEQ ID NOs 15-22.

All the above vectors use the strong promoter preceding the groESL operon of *Bacillus subtilis* fused to the lac operator allowing their induction by addition of IPTG (isopropyl beta-D-1-thiogalactopyranoside).

Figure 13:
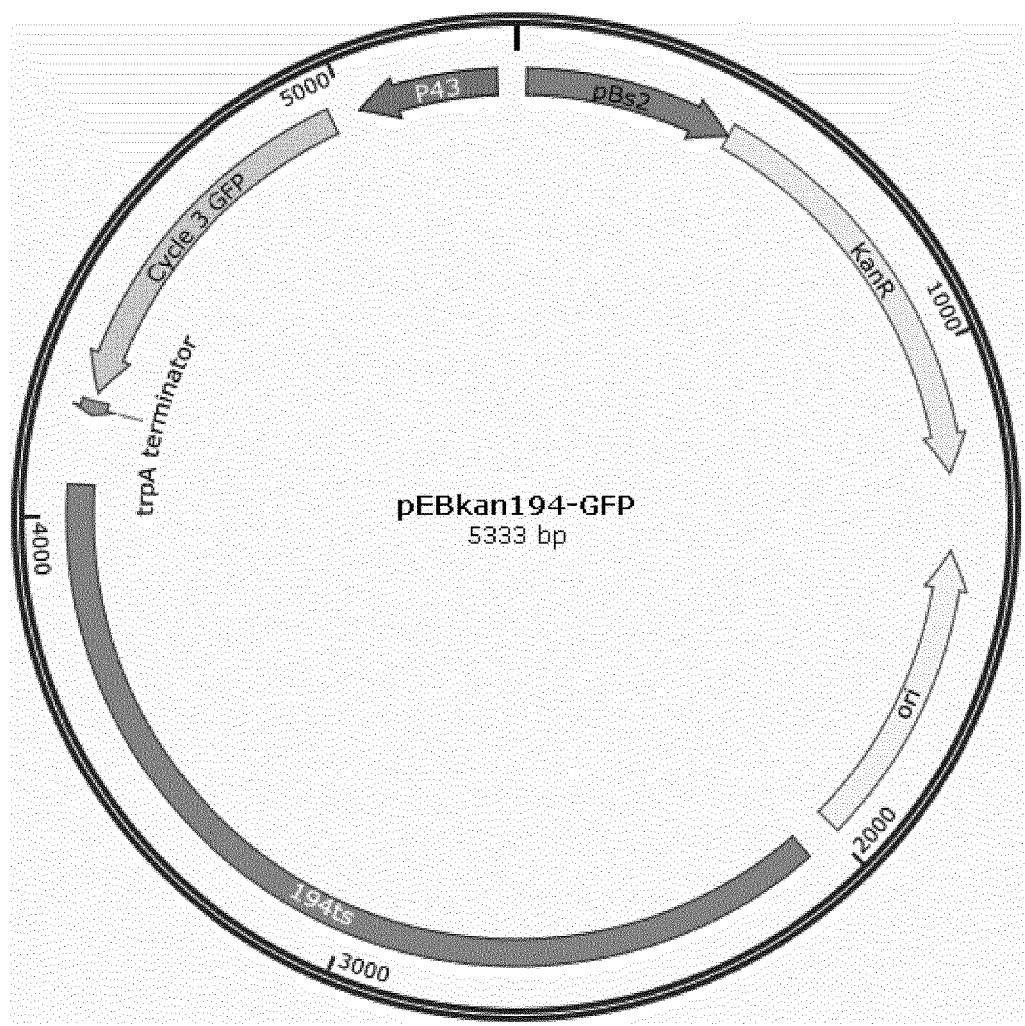

Other suitable vectors appear from the examples and figures herein including three integrative vectors containing a modified *B, licheniformis* alkaline protease gene. The plasmid pEBKan194-GFP (FIG. 13), which is naturally temperature sensitive above 42° C., is used for construction of various knockout and knockin vectors. Vectors with the up and down homologous arm of apr, xylA, gntP and ywaD gene of *B. licheniformis* CICC10266 (pEBkan194-GFP-aprFR1, pEBkan194-GFP-XylFR, and pEBkan194-GFP-gntPFR) were used to obtain pEBkan194-GFP-aprFR1-10266apr-W4, pEBkan194-GFP-Xy1FR-10266apr-W4, pEBkan194-GFP-gntpFR-10266apr-W4. The products could be transformed into *E. coli* as demonstrated in the examples herein.

Figure 14:
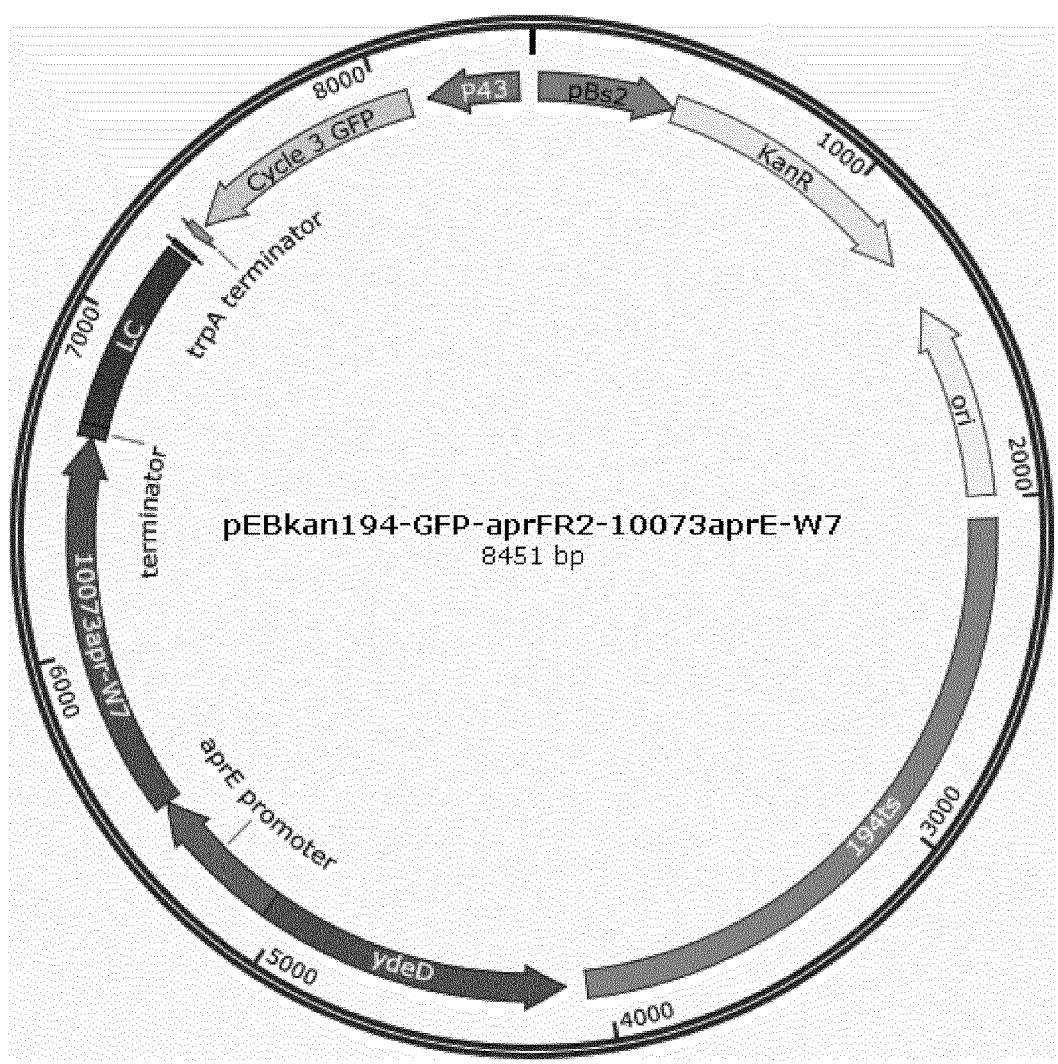
Figure 16:
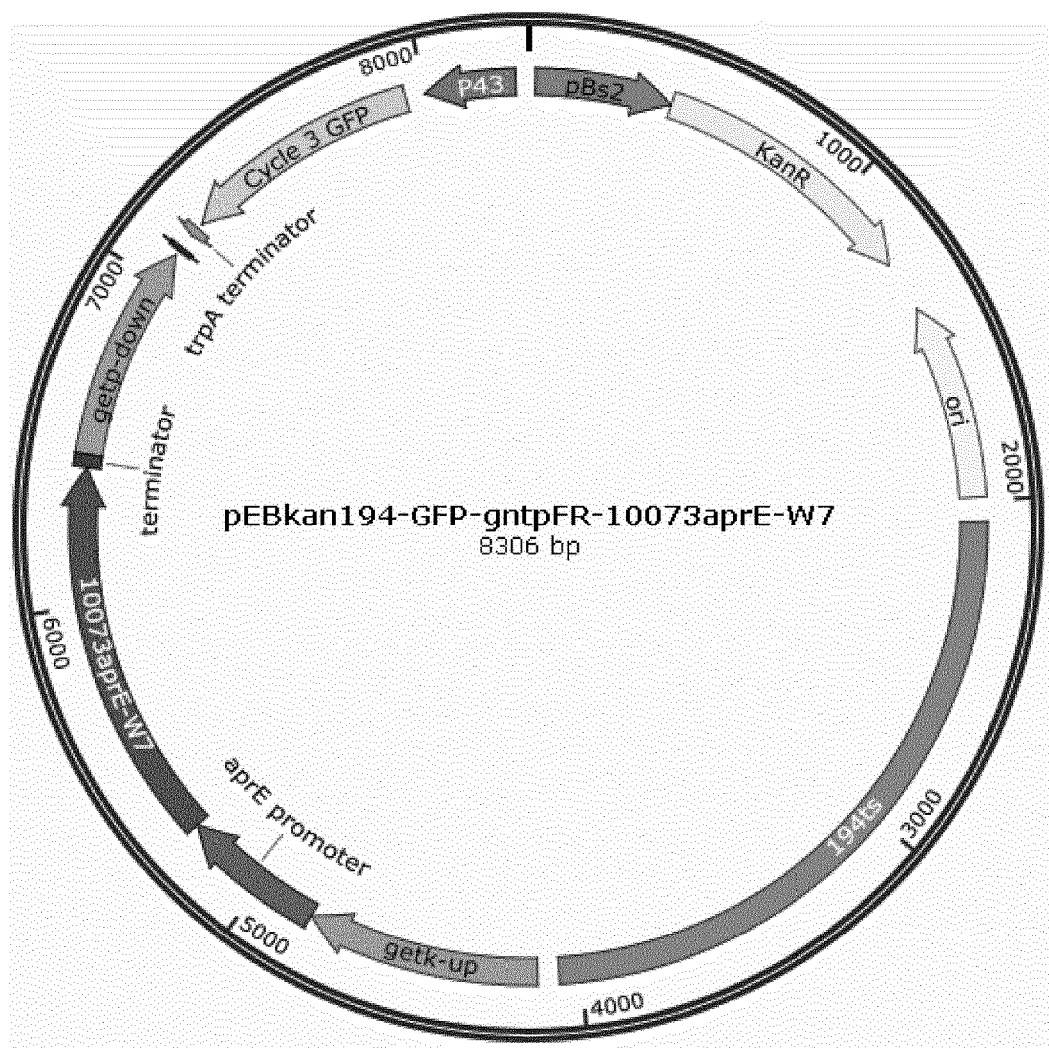
Figure 17:
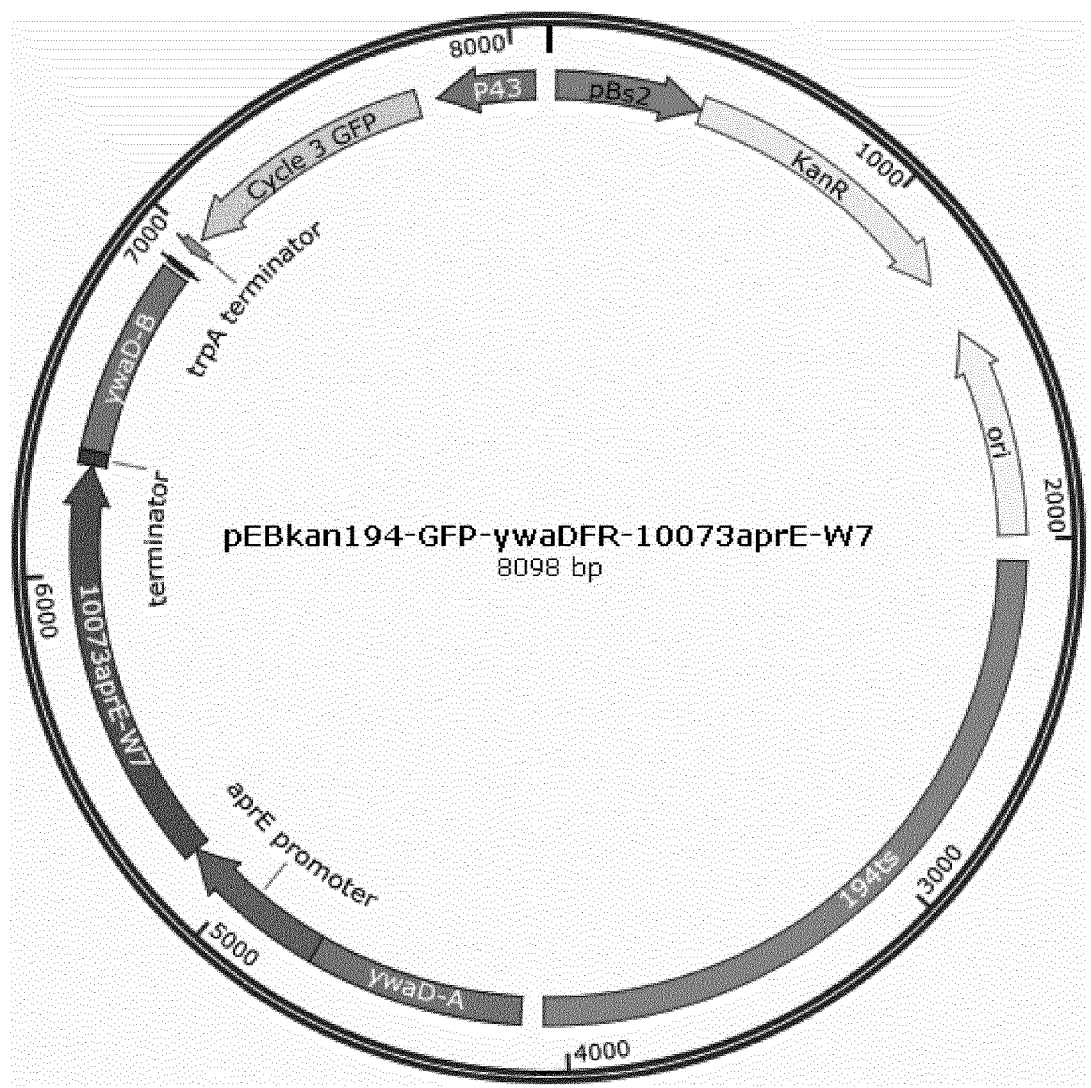

Four other knockin vectors with the up and down homologous arm gene fragments of apr, xylA, gntP and ywaD gene of *B. licheniformis* CICC10266 (pEBkan194-GFP-ydeDLC, pEBkan194-GFP-XylFR, pEBkan194-GFP-gntPFR and pEBkan194-GFP-ywaDFR) can be used e.g. to obtain pEBkan194-GFP-aprFR2-10073aprE-W7 (FIG. 14), pEBkan194-GFP-XylFR-10073aprE-W7 (FIG. 15), pEBkan194-GFP-gntpFR-10073maprEW7 (FIG. 16), pEBkan194-GFP-ywaDFR-10073aprE-W7 (FIG. 17). The positive clones are identified by colony PCR. *E. coli* clones identified with the right plasmids were preserved and used for plasmid extraction. As shown in the examples, the plasmids can be used for electro-transforming into *B. licheniformis* CICC10266 (Δapr yhfN) strain.

As shown in the examples and figures, the introduced DNA sequences may contain a segment of *B. licheniformis* chromosomal DNA found 5' upstream of the apr gene promoter, a strong apr promoter, the apr signal peptide, the modified alkaline protease, and the 3' downstream of the apr gene. The modified *B. licheniformis* apr gene sequence and the amino acid sequence of the mature Phe-free protein are shown in SEQ NO. 73-74.

The vector may also contain one or more selectable markers that permit easy selection of transformed, transfected, transduced, or the like cells. A selectable marker is a gene the product of which provides for both biocide or viral resistance, resistance to heavy metals, and the like.

Suitable markers may be ampicillin, kanamycin, chloramphenicol or neomycin.

For integration into the host cell genome, the vector may rely on the polynucleotide's sequence encoding the protein or any other element of the vector for integration into the genome by homologous or non-homologous recombination. Alternatively, the vector may contain additional polynucleotides for directing integration by homologous recombination into the genome of the host cell at a precise location(s) in the chromosome(s).

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Four different origins of replication have been used in the present context and come from the common *Bacillus* plasmids of pHT43, pWB980, pHY300PLK and pHIS1525.

The pHT43 and pHT01 vectors or the other recombinant vectors mentioned above are mainly used for expression testing of these proteins. Preferred, however, is a *Bacillus* expression system without the need of an inducer and the product gene will be integrated into chromosome DNA. The final production strain will be very similar to the non-genetically modified strain, e.g., no free plasmid introduced, no antibiotics gene introduced, the expression systems may be the same as these natural expression systems for alkali protease and alpha-amylase from *B. subtilis* and *B. licheniformis* strains. Spore formation gene may be knocked out as well, as described herein.

Nucleic Acid Constructs

The present invention relates to nucleic acid constructs comprising a polynucleotide encoding a Phe-free protein of the present invention operably linked to one or more control sequences that direct the expression of the coding sequence in a suitable host under conditions compatible with the control sequence.

The polynucleotide may be manipulated in a variety of ways to provide for expression of the Phe-free protein. Manipulation of the polynucleotide prior to its insertion into a vector may be desirable or necessary depending on the expression vector. The techniques for modifying polynucleotides utilizing recombinant DNA are well known to a person skilled in the art.

The control sequence may be a promoter, a polynucleotide recognized by a host cell for expression of a polynucleotide encoding a Phe-free protein of the present invention. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promotes for directing transcription of the nucleic acid constructs of the present invention in a bacterial cell are promoters obtained from bacteria, virus or others, such as Pgrac or Pgrac promotor mutants P100, P233 or P250 (SEQ ID NOs 17, 18 and 19, respectively).

Other promoters were also used for the expression of recombinant Phe-free proteins, such as constructive (P43, PaprE, PnprE, PamyE, PsipS, PBlapr and PamyS) and self-induction promoters (pery32a and PAPase). The sequences of these promoters are given as SEQ ID Nos 50-58, respectively.

The pGAP and pAOX1 promoters from *Pichia pastoris* may direct transcription of the nucleic acid constructs of the present invention in *P. pastoris*.

The hp4d promoters from *Yarrowia lipolytica* may direct transcription of the nucleic acid constructs of the present invention in *Y. lipolytica*.

The control sequence may also be a transcription terminator, which is recognized by a host cell to terminate transcription. The terminator is operably linked to the 3'-terminus of the polynucleotide encoding a protein. Any terminator that is functional in the host cell may be used such as TAA, TGA, TAG.

The control sequence may also be a leader a non-translated region of an mRNA that is important for the translation by the host cell. The leader is operably linked to the 5'-terminus of the polynucleotide encoding a Phe-free protein of the invention. Any leader that is functional in the host cell may be used.

In the examples, no leader has been used, but signal peptide for secretion and propeptide, which are not part of final product, are used, such as aprE and Blapr need signal peptide and pro-peptide for secreted expression in *B. subtilis* and *B. licheniformis*.

The procedures used to ligate the elements described above to construct the recombinant expression vectors of the present invention are well-known to a person skilled in the art.

Constructing, Screening a High Expression Vector Without Requiring an Inducer

In order to reduce the cost of large-scale fermentation production, expression without inducer (IPTG, xylose lactose or other compounds) is preferred. Some constructive and auto-inducible promoters will be cloned for construct expression vector.

Although a lot of *B. subtilis* expression vectors can be found in various literatures, commercial expression vectors are still rare. A lot of plasmids in *B. subtilis* are unstable and have low copies. Moreover, the expression level of recombinant protein is also relative low. The present inventors purchased two IPTG-induction expression plasmids pHT01 and pHT43 from MoBiTec and constructed a constructive expression plasmid pWB980. However, the expression level of our target protein is lower compared with other wild strains reported in literature when using the pHT01 and pHT43 plasmids. The two plasmids are unstable in *E. coli* and have low copies in *B. subtilis*. Furthermore, the pWB980 plasmid is a non-shuttle pUB110-derived plasmid and unstable during culture.

Moreover, the genetic transformation of pWB980 plasmid has been hampered by low transformation efficiencies.

In order to overcome these problems and improve the expression level of target proteins, some *E. coli-B. subtilis* shuttle and integrated vectors must be constructed and tested in *B. subtilis*. Although there is no commercial expression vector for *B. licheniformis*, but some of *E. coli-B. subtilis*, shuttle vectors may be used in *B. licheniformis*.

Removing all Antibiotic Genes from Expression Host

In order to solve the instability of recombinant plasmids in *Bacillus*, integrated vectors for integrating target gene into the genome of *B. subtilis* and *B. licheniformis* will be constructed. The genes encoding the Phe-free proteins could be inserted into the genome of *B. subtilis* at least nine locus (amylase and eight protease genes). The genes encoding the Phe-free proteins could be inserted into the genome of *B. licheniformis* at least three locus (protease, amylase and chloramphenicol acetyltransferase genes).

However, the exogenous antibiotic gene is also inevitably integrated into the genome of *B. subtilis* and *B. licheniformis*. Moreover, several exogenous of antibiotic genes have been inserted into the *B. subtilis* WB800N (eight-extracellular-protease-deficient strain) strain that commonly is used as expression host. The recombinant Phe-free protein according to the present invention will be produced at large scale, so the exogenous antibiotic genes from the genome of *B. subtilis* and *B. licheniformis* will be removed for environment protection.

Multiple Copies of the Product Genes with Multiple Secretary Pathways

More than one copy of polynucleotide of the present invention may be inserted into a host cell to increase the production of the protein. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

Multiple copies of the product genes integrated into the genome may increase the expression level. If the multiple copies of genes link with different secretion signals to be secreted through different pathways, the product yield may be increased further. The absence of an outer membrane in Bacillus simplifies protein secretion pathways allows the organism to secrete high levels of extracellular proteins. B. subtilis and B. licheniformis have three and five different protein secretion pathways, respectively. The Sec pathway constitutes the main secretion pathway in B. subtilis and B. licheniformis. Alternatively, a small number of extracellular proteins with specific functions are secreted via Tat pathway or ABC transporters in B. subtilis. The formation of inclusion bodies was found to be a limiting factor in B. subtilis when the secretion pathway overloads. So, a lot of signal peptides will be tested to increase the secretory level of target protein.

As seen from the examples herein at least 2 copies may be inserted such as 3 copies or more.

Deleting the Genes for the Main Extracellular Miscellaneous Proteins

In order to simplify the purification process and reduce the cost, the main extracellular miscellaneous protein of B. subtilis and B. licheniformis may be identified and deleted. Two genes encoding the main extracellular proteins in B. subtilis WB800N are identified as flagellin and superoxide dismutase. These two genes may be knocked out.

Knockout the Main Genes Involved Forming Spores

In order to avoid forming spores during fermentation, to extend the culture time for protein production and to reduce the risk of spore formation in the bioreactor, the main genes involved forming spores in B. subtilis and B. licheniformis will be deleted.

Methods for Producing Phe-Free Proteins

The present invention also relates to methods of producing recombinant Phe-free or Phe-low proteins of the present invention, the method comprising i) cultivating a recombinant host cell of the present invention under conditions conductive for production of the protein, and ii) recovering the protein.

The host cells are cultivated in a nutrient medium suitable for production of the Phe-free protein using method well known in the art. For example, the cells may be cultivated in multi-well plates, shake flask cultivation or small-scale or large-scale fermentation (including continuous, batch, fed-batch or solid state fermentation) in laboratory or industrial fermenters in a suitable medium and under conditions allowing the protein to be expressed and/or isolated. The cultivation takes place in a suitable nutrient medium comprising carbon and nitrogen sources and inorganic salts, using procedures known in the art. The cultivation takes place firstly in some nutrient mediums comprising carbon and nitrogen sources and inorganic salts, using procedures known in the art. Then, a suitable medium, culture conditions and high cell-density culture progress will further optimize in small-scale or large-scale fermentation.

Optimization of Fermentation and Scale Up

Recombinant protein production is usually dependent on fermentation conditions. The culture medium compositions, culture temperature, dissolved oxygen, and pH all are important factors affecting cell growth and protein expression. An expression level greater than 10 g/L is a challenge to the extreme of the ability of the bacteria. Most of these factors have to be optimized to their best conditions. These factors will be well investigated at small scales, and then will scale up to manufacturing scale.

Purification Strategies

A simple and non-expensive purification process is desired to maintain the whole manufacturing cost low. A GRAS expression system without free plasmid will allow the product containing certain level of impurities from the broth. Removing most of these extracellular proteins through deleting their genes limits protein impurities, which is important in order to maintain the product Phe content low. A certain tag, for an example, a temperature sensitive tag, will be added to the target protein genes. Therefore, the target protein may precipitate when temperature increase to a certain level.

In principle any suitable purification process may be used including common industryal methods like filtration or, alternatively, purification by use of silica (e.g. underivatized silica, stationary phase in chromatographic settings etc.)

Optimization of Recombinant Proteins

The recombinant protein amino acid composition will be optimized according to PKU nutrient requirements and disease treatment requirements such as increasing the content of LNAA.

List of Sequences

| SEQ ID NO (protein) | SEQ ID NO (gene) | Name |
|---|---|---|
| 1 | 59 | ΔPro1/ΔPro1 gene fragments |
| 2 | 60 | ΔPro2/ΔPro2 gene fragments |
| 3 | 61 | ΔamyQ/ΔamyQ gene fragments |
| 4 | 62 | ΔyjeA |
| 5 | 63 | estA/estA gene fragments without native signal peptide |
| 6 | 64 | estB/estB gene fragments without native signal peptide |
| 7 | 65 | aprE/aprE gene |
| 8 | 66 | amyE/amyE gene |
| 9 | 67 | amyL/amyL gene |
| 10 | 68 | nprE/NprE gene |
| 11 | 69 | ALAB/ALAB gene without native signal peptide |
| 12 | 70 | Blapr/Blapr gene |
| 13 | 71 | Lip/Lip gene |
| 14 | 72 | EGFP/EGFP gene |
| 15 | | pHT01 |
| 16 | | pHT43 |
| 17 | | P100 |
| 18 | | P223 |
| 19 | | P250 |
| 20 | | P431 |
| 21 | | P432 |
| 22 | | P433 |
| 23 | | Encoding the signal peptide of amyQ |
| 24 | | Encoding the native signal peptide of aprE |
| 25 | | Anti-microbial peptide from B. subtilis (PDB code 2B9K) |
| 26 | | Mutated protein of SEQ ID NO 7: aprE50Y189Y261L |
| 27 | | Mutated protein of SEQ ID NO 7: aprE50Y189Y261LCC |
| 28 | | Mutated protein of SEQ ID NO 12: Blapr58Y188Y260W |
| 29 | | Mutated protein of SEQ ID NO 12: Blapr58Y188Y260WCC |
| 30 | | Mutated protein of SEQ ID NO 12: Blapr58C188Y260W |
| 31 | | Mutated protein of SEQ ID NO 5: estA17Y19Y41C58Y |
| 32 | | Mutated protein of SEQ ID NO 5: estA17W19Y41C58Y |

| SEQ ID NO (protein) | SEQ ID NO (gene) | Name |
|---|---|---|
| 33 | | Mutated protein of SEQ ID NO 6: estB20Y21M40C |
| 34 | | Mutated protein of SEQ ID NO 11: ALAB-V4 |
| 35 | | Mutated protein of SEQ ID NO 11: ALAB-M1V3 |
| 36 | | Mutated protein of SEQ ID NO 11: ALAB-Y1V3 |
| 37 | | Mutated protein of SEQ ID NO 11: ALAB-H1V3 |
| | 38 | aprE50Y189Y261L; signal peptide + Pro-peptide + mature peptide |
| | 39 | aprE50Y189Y261LCC; signal peptide + Pro-peptide + mature peptide |
| | 40 | BIapr58Y188Y260W; signal peptide + Pro-peptide + mature peptide |
| | 41 | BIapr58Y188Y260WCC; signal peptide + Pro-peptide + mature peptide |
| | 42 | BIapr58C188Y260W; signal peptide + Pro-peptide + mature peptide |
| | 43 | estA17Y19Y41C58Y |
| | 44 | estA17W19Y41C58Y |
| | 45 | estB20Y21M40C |
| | 46 | ALAB-V4 |
| | 47 | ALAB-M1V3 |
| | 48 | ALAB-Y1V3 |
| | 49 | ALAB-H1V3 |
| | 50 | P43 promoter from genome of *B. subtilis* |
| | 51 | PaprE promoter from genome of *B. subtilis* |
| | 52 | PNprE promoter from genome of *B. subtilis* |
| | 53 | PamyE promoter from genome of *B. subtilis* |
| | 54 | PsipS promoter from genome of *B. licheniformis* |
| | 55 | PBIapr promoter from genome of *B. licheniformis* |
| | 56 | PamyS promoter from genome of *B. licheniformis* |
| | 57 | Pcry82 promoter, a synthetic promoter based on the pcry32a promoter from the *B. thuringiensis* |
| | 58 | PAPase promoter from genome of *B. licheniformis* |
| | 73 | 10266apr gene (gene sequence, from *Bacillus licheniformis* CICC10266) |
| 74 | | 10266apr (protein sequence, from *Bacillus licheniformis* CICC10266) |
| | 75 | 10266apr-W4 gene (gene sequence) |
| 76 | | 10266apr-W4 (protein sequence) |
| | 77 | 10073aprE gene (gene sequence, from *Bacillus subtilis* CICC10073) |
| 78 | | 10073aprE (protein sequence, from *Bacillus subtilis* CICC10073) |
| | 79 | 10073aprE-W7 gene (mutative gene sequence) |
| 80 | | 10073aprE-W7 (protein sequence) |

Specific Embodiments

Embodiments of the invention appear from the appended claims, which hereby are included in the present description of the invention.

In particular the invention also relates to the specific method:

A method of generating a recombinant microorganism comprising a nucleic acid sequence mutated to be Phe-free or Phe-low (without Phe content or with at the most 40% Phe content, calculated as number of aa compared with total number) comprising the steps:

i. Making phe-specific mutations in said nucleic acid sequence using site directed mutagenesis to replace single Phe codons with single LNAA codons,
ii. Restriction enzyme (DpnI) removal and purification of the mutated nucleic acid sequence followed by ligation into a temperature-sensitive vector capable of initiating rolling circle recombination at introduced homologous gene fragments from a *Bacillus* final production strain (CICC10266) at temperatures of 42° C. or greater and carrying a gene conferring kanamycin resistance and another gene encoding a green fluorescent protein (pEBKan194-GFP),
iii. Transformation of said vector carrying said mutated nucleic acid sequence into *E. coli* (DH5α or TOP10), followed by colony PCR of successful transformants,
iv. Extraction of said vector carrying the mutated nucleic acid sequence from said *E. coli* transformants, and electro-transformation into a *B. licheniformis* final production strain which has previously had the wild type gene of said nucleic acid sequence completely removed, (CICC10266 is Δapr yhfN⁻), selection for growth of kanamycin resistant and fluorescent transformants at 42-44° C.,
v. integration of the mutated nucleic acid sequence at target genes within the *B. licheniformis* or *B. subtilis* final production strain at said areas of homology introduced in to said vector is then selected on duplicate plates for loss of kanamycin resistance, with the presence of said mutated nucleic acid sequence confirmed by sequencing.

The vector of step (iii) may comprise regulatory sequences, promoters, and signal sequences associated with the wild type nucleic acid sequence.

The recombinant microorganism may be transformed with further vectors generated according to steps (i) to (iii) with different gene fragments at which recombination occurs, so that additional copies of said Phe-free or Phe-low recombinant nucleic acid sequence is integrated into the *bacillus* genome at several targeted locations.

FIGURES

FIG. 1. Phe metabolism in human. Intake of L-Phe is via the diet and it is recycled through amino acid pools. Hydroxylation by PAH with its cofactor BH4, in the presence of molecular $O_2$, produces L-Tyr. Alternative metabolism of L-Phe by decarboxylation or transamination produces various metabolites that are excreted in urine[6].

FIG. 2. The enzyme phenylalanine hydroxylase converts phenylalanine to tyrosine together with the cofactor tetrahydrobiopterin (BH4).

FIG. 3. The figure presents the different treatment options available in practice or in theory, looking at different locations in the body.

Figure 4:
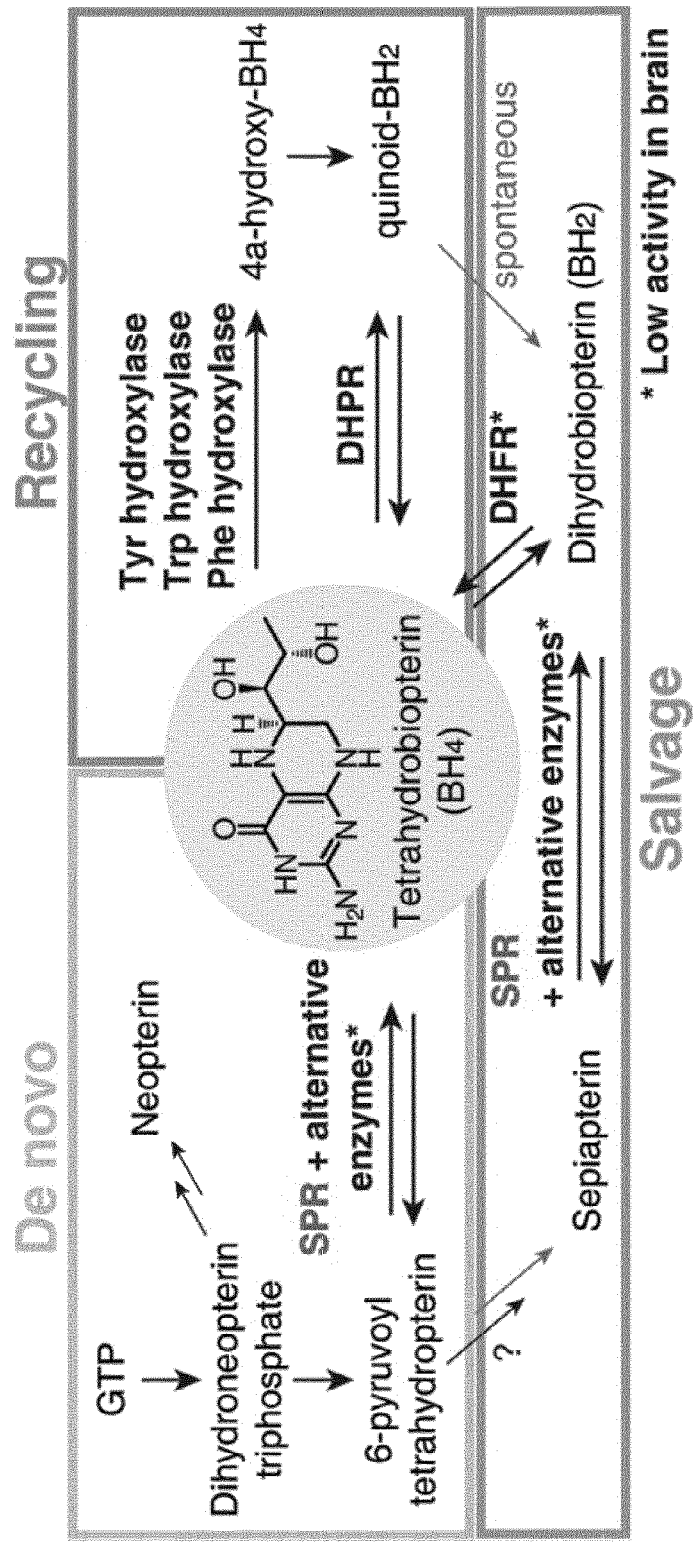

FIG. 4. BH4 biosynthetic pathways. Sepiapterin reductase (SPR) catalyzes formation of BH4 from 6-pyruvoyltetrahydropterin and of BH2 from sepiapterin in a salvage pathway [24]. DHFR, dihydrofolate reductase.

Figure 5:
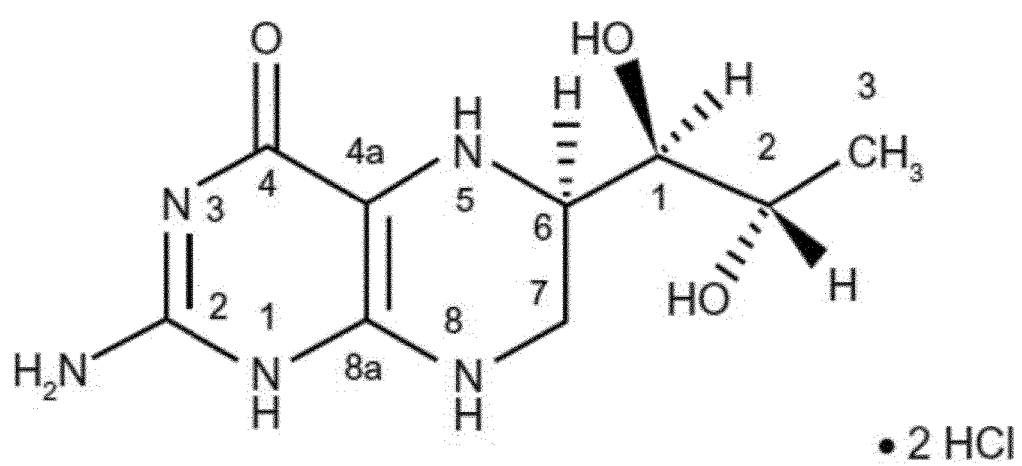

FIG. 5. The Chemical structure of sapropterin dihydrochloride (Trade name: Kuvan®)[32].

FIGS. 6A and B. Dietary Differences between LNAA Diet and the Traditional PKU Diet.

Figure 7:
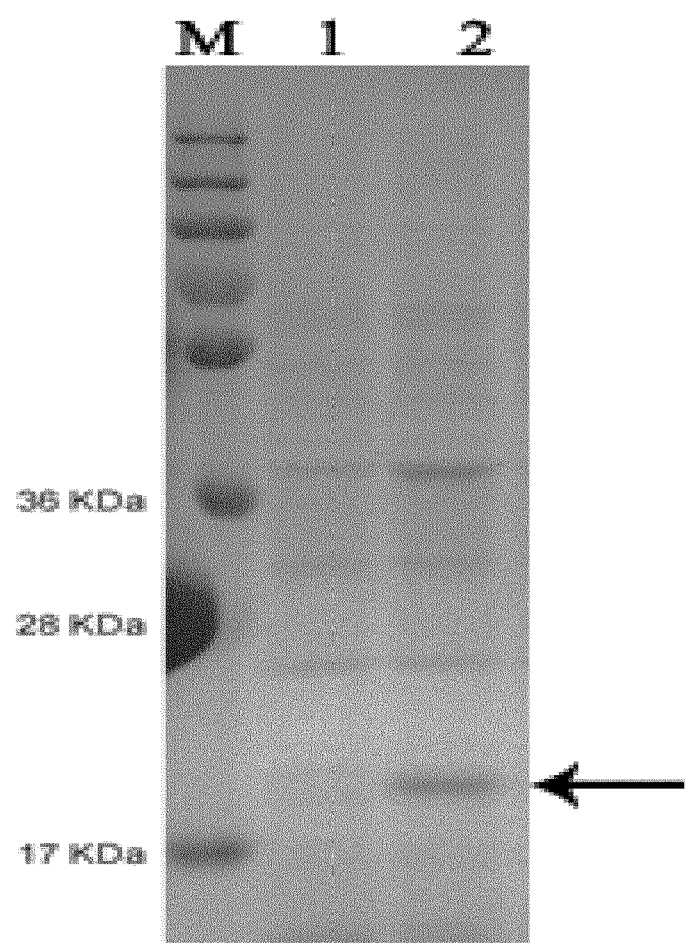
Figure 8:
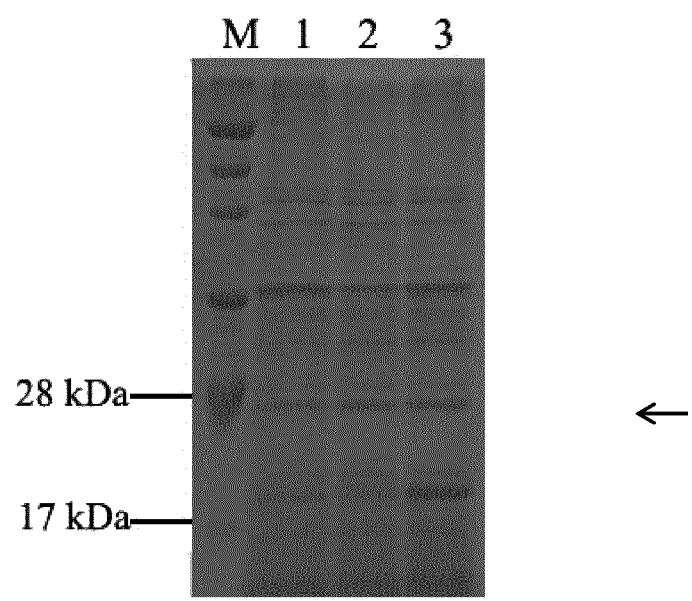
Figure 9:
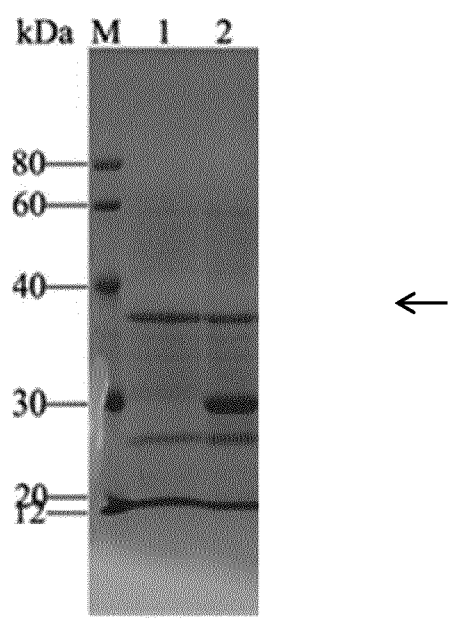
Figure 11:
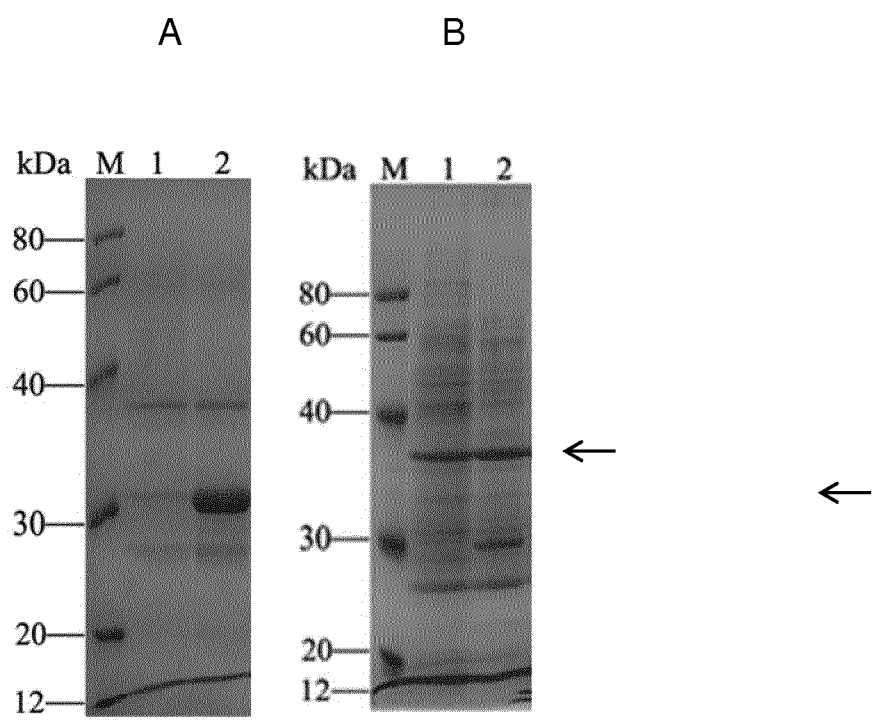
Figure 12A:
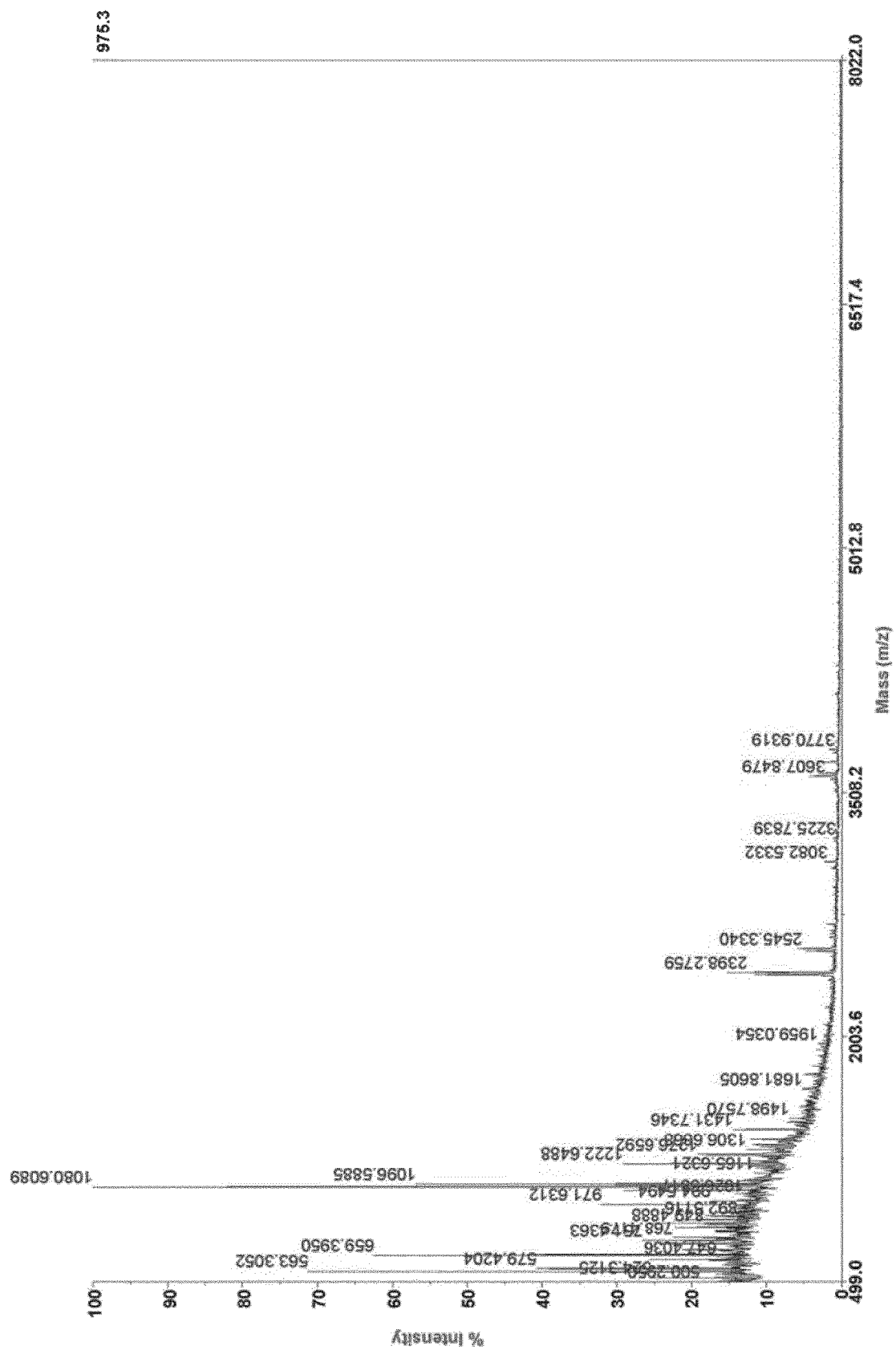
Figure 12B:
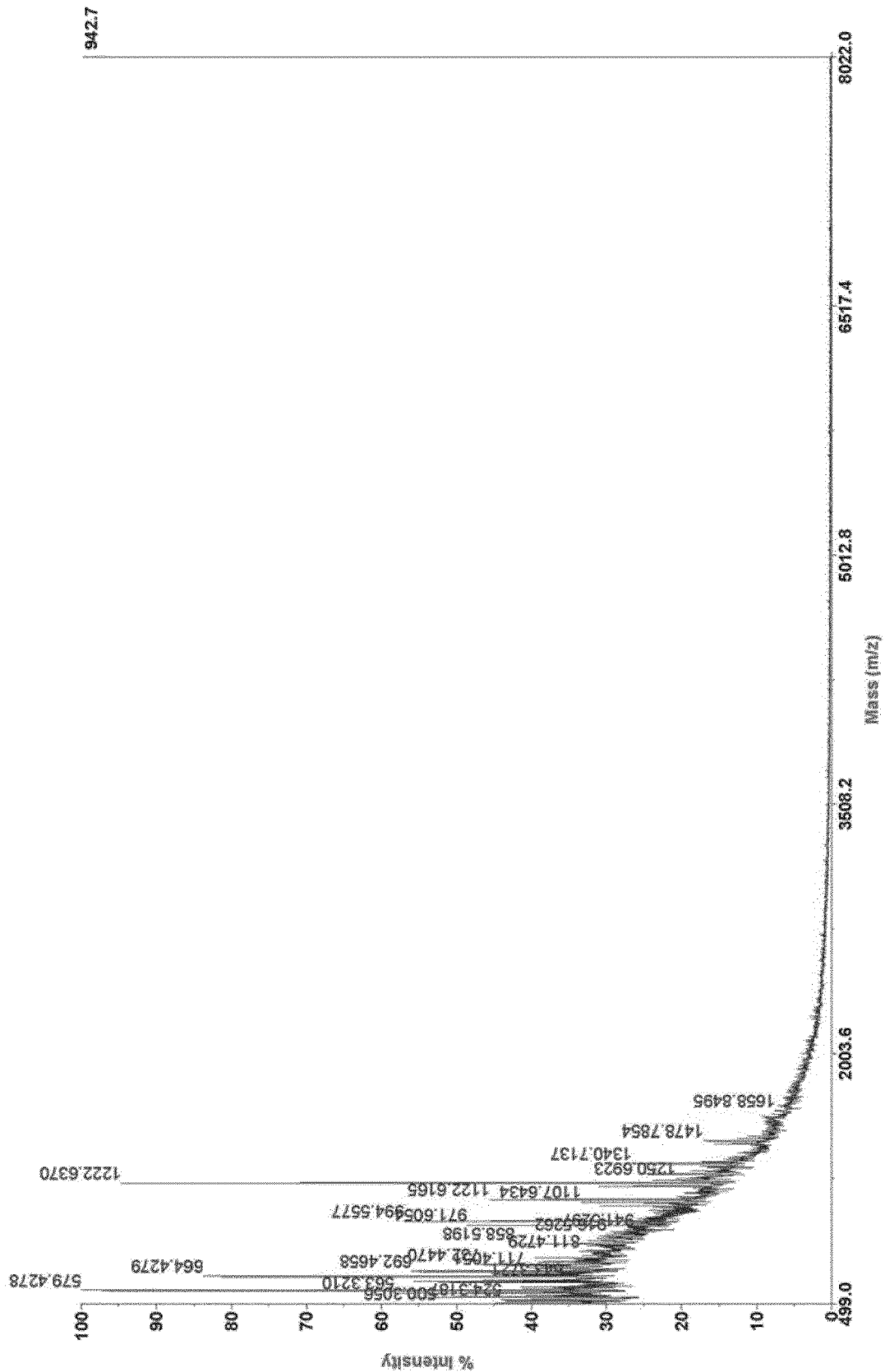

FIG. 7. SDS-PAGE analysis of the expression of estB in *B. subtilis* WB800N strain. M: protein marker; lane 1, control; lane 2, recombinant strain was inducted by IPTG in LB medium for 2.5 h FIG. 8. SDS-PAGE analysis of the expression of estA in *B. subtilis* WB800N strain. M: protein marker; lanes 1 and 2, control; lane 3, recombinant strain was inducted by IPTG in LB medium for 2.5 h FIG. 9. SDS-PAGE analysis of the expression of aprE in *B. subtilis* WB800N strain. M: protein marker; lane 1, control; lane 2, recombinant strain was inducted by IPTG in LB medium for 4 h FIG. 10. SDS-PAGE analysis of the expression of maprE in *B. subtilis* WB800N strain. M: protein marker; lane 1, control; lane 2, recombinant strain was inducted by IPTG in LB medium for 4 h FIGS. 11A and B. SDS-PAGE analysis of the expression of maprE in *B. subtilis* WB800N strain with pHT432 vector (left) and pHT01 (right). M: protein marker; lane 1, control; lane 2, recombinant strain was inducted by IPTG in LB medium for 4 h FIG. 12. Pepsin (12A) and trypsin (12B) digestion of heat denatured Blapr to indicate that cooked Blapr is well digestible in human GI tract FIG. 13. Schematic diagram of the temperature sensitive plasmid pEBkan194-GFP FIG. 14. Schematic diagram of the temperature sensitive plasmid pEBkan194-GFP-aprFR2-10073aprE-W7

Figure 15:
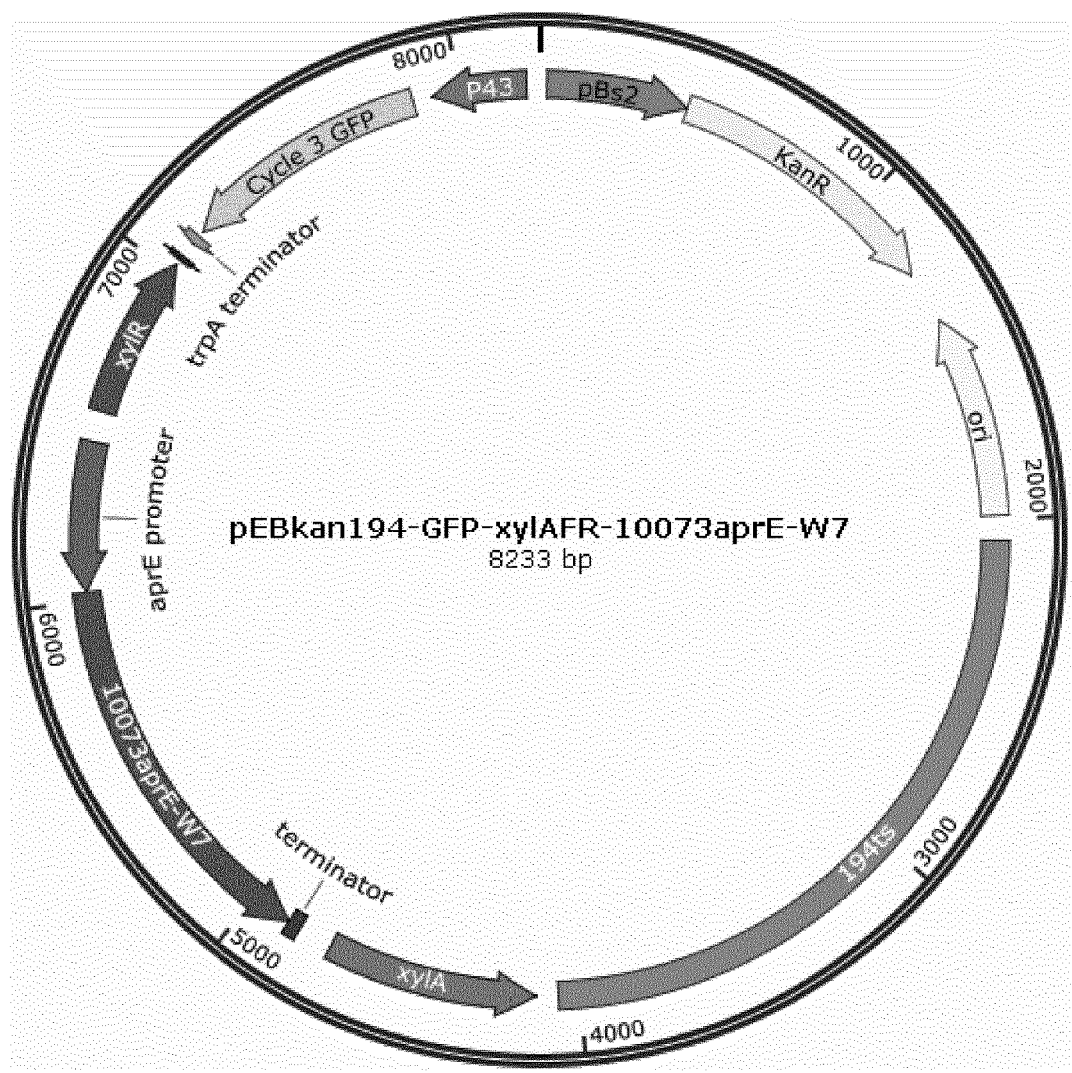

FIG. 15. Schematic diagram of the temperature sensitive plasmid pEBkan194-GFP-xylAFR-10073aprE-W7

FIG. 16. Schematic diagram of the temperature sensitive plasmid pEBkan194-GFP-gntPFR-10073aprE-W7

FIG. 17. Schematic diagram of the temperature sensitive plasmid pEBkan194-GFP-ywaDFR-10073aprE-W7

Figure 18:
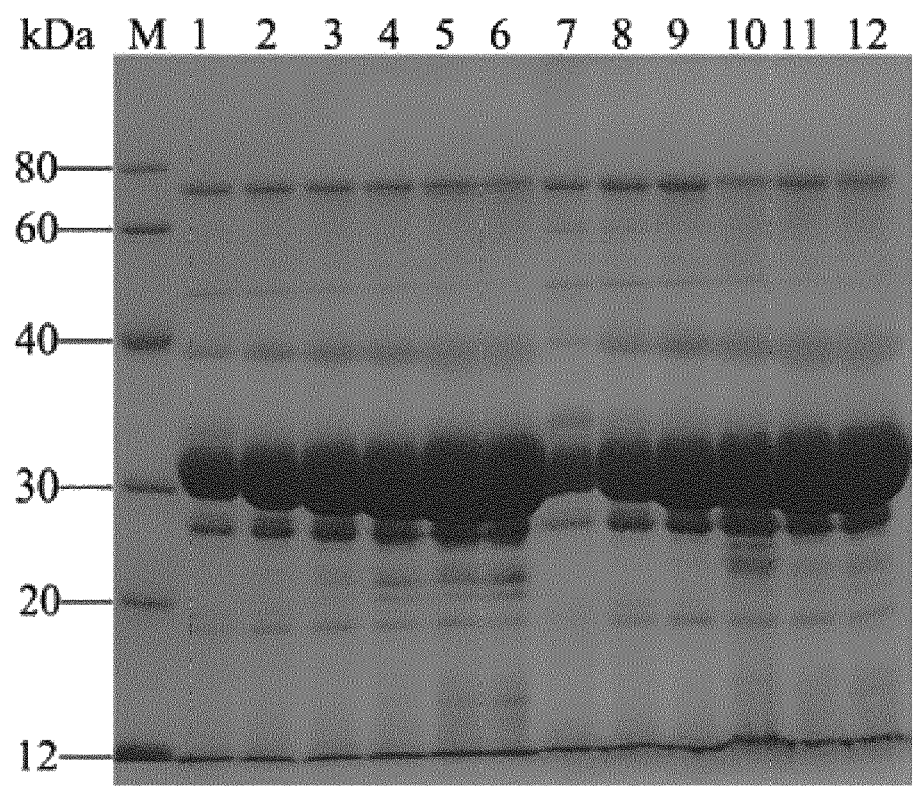

FIG. 18. SDS-PAGE analysis of the production of 10266apr-W4 using YRBLS025 strain in 5 L fermnetor with SC2 and SC3 media. Lane M, low molecular weight marker (TaKaRa); lanes 1-6, 5 μL of culture supernatant of 18, 20, 22, 24, 26 and 28 h with SC2 media, respectively; lanes 7-12, 5 μL of culture supernatant of 18, 20, 22, 24, 26 and 28 h with SC3 media, respectively.

Figure 19:
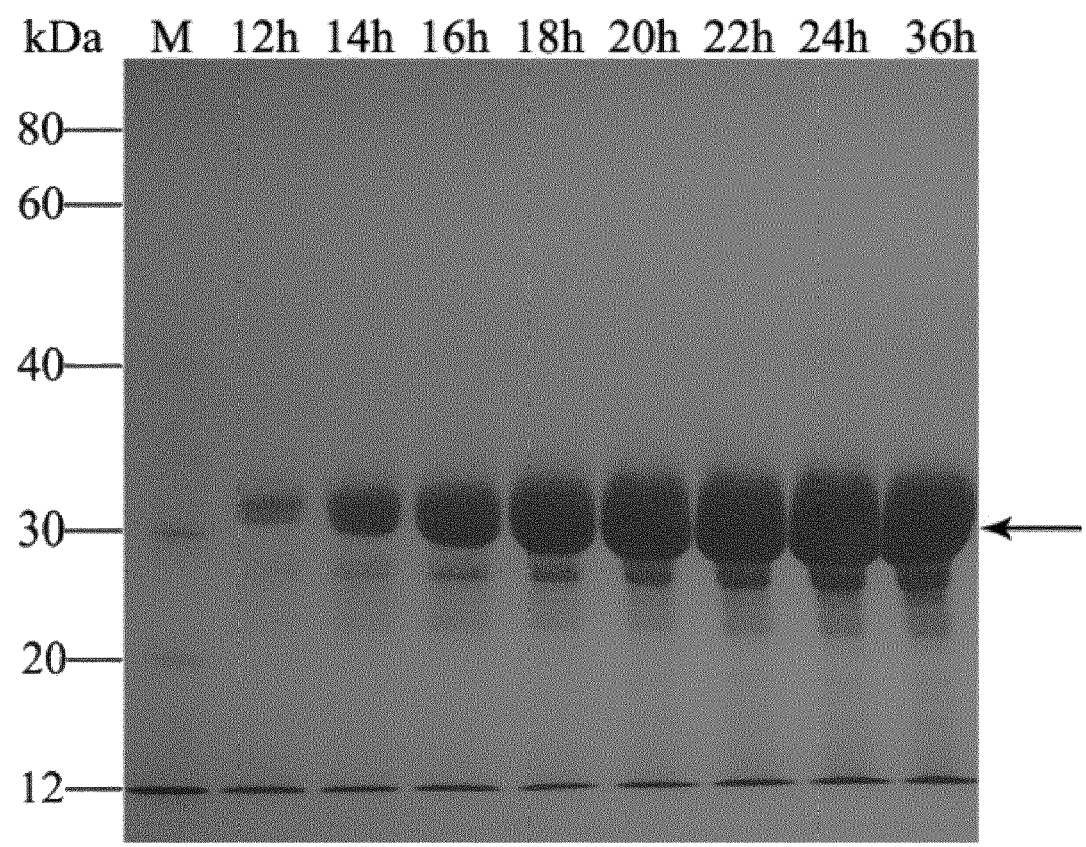

FIG. 19. SDS-PAGE analysis of the production of 10266apr-W4 using YRBLS025 strain in 50 L fermentor with SC3 media. Lane M, low molecular weight marker (TaKaRa); lanes 12 h-36 h, 5 μL of culture supernatant of 12, 14, 16, 18, 20, 22, 24 and 36 h, respectively.

Figure 20:
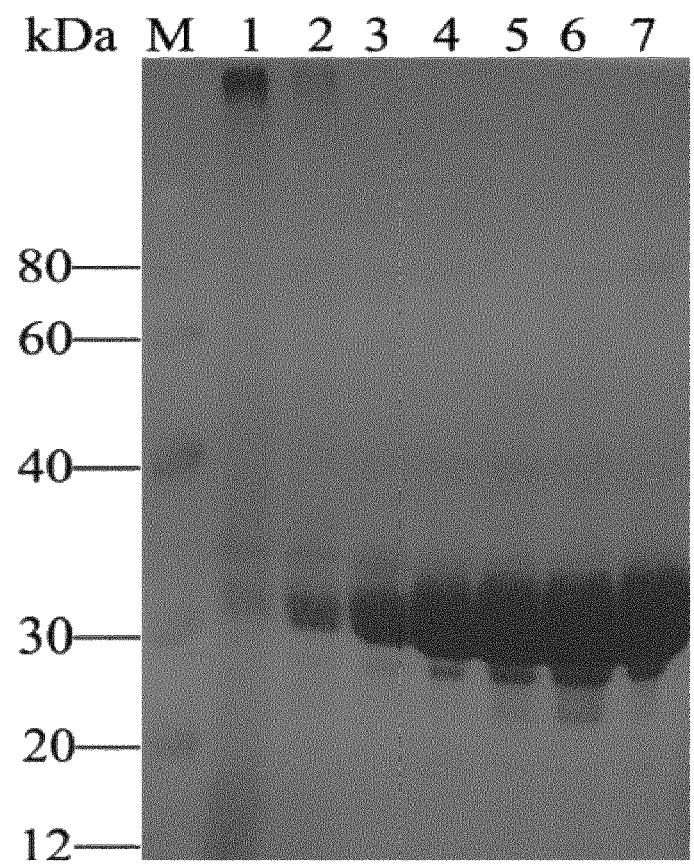

FIG. 20. SDS-PAGE analysis of the production of 10266apr-W4 using YRBLS025 strain in 500 L fermentor with SC3 media. Lane M, low molecular weight marker (TaKaRa); lanes 1-7, 5 μL of culture supernatant of 8, 10, 14, 18, 20, 22 and 25 h, respectively.

ABBREVIATIONS

PKU phenylketonuria
HPA hyperphenylalaninemias
Phe phenylalanine
PAL phenylalanine ammonia lyase
PAH or Pah-gene; PAH or Pah-enzyme phenylalanine hydroxylase
GMP glycomacropeptide
LNAA large neutral amino acids
GTPCH I GTP cyclohydrolase I
PTPS 6-Pyruvoyl tetrahydropterin synthase
SPR S epiapterin reductase
BH4 Tetrahydrobiopterin
BP Biopterins
aa amino acid Definitions cDNA: The term "cDNA" means a DNA molecule that can be prepared by reverse transcription from a mature, spliced mRNA molecule obtained from a cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of the enzyme or variant of the enzyme. The boundaries of the coding sequence are generally determined by an open reading frame, which begins with a start codon such as ATG, GTG or TTG and ends with a stop codon such as TAA, TAG or TGA. The coding sequence may be genomic DNA, cDNA, synthetic DNA, or a combination thereof.

Control sequences: The term "control sequences" means nucleic acid sequences necessary for expression of a polynucleotide encoding a protein or variant of the present invention. Each control sequences must be native (i.e. from the same gene) or foreign (i.e. from a different gene) to the polynucleotide encoding the protein or variant thereof or native or foreign to each other. Such control sequences include a promoter, and transcriptional and translational stop signals. The control sequences may be provided with linkers for the purpose of introducing specific restriction sites facilitating ligation of the control sequence with the coding region of the polynucleotide encoding the protein or variant thereof.

Expression: The term "expression" includes any step involved in the production of a protein thereof including, but not limited to, transcription, post-transcriptional modification, translation, post-translational modification, and secretion.

Expression vector: The term "expression vector" means a linear or circular DNA molecule that comprises a polynucleotide encoding a protein and is operably linked to control sequences that provide for its expression.

Host cell: The term "host cell" means any cell type that is susceptible to transformation, transfection, transduction, or the like with a nucleic acid construct or expression vector comprising a polynucleotide as described herein.

Isolated: The term "isolated" means a substance in the form or environment that does not occur in nature. Non-limiting examples of isolated substances include i) any non-naturally occurring substance, ii) any substance including, but not limited to, any enzyme, variant, nucleic acid, protein, peptide or cofactor, that is at least partially removed from one or more or all of the naturally occurring constituents with which it is associated in nature, iii) any substance modified by the hand of man relative to that substance found in nature, or iv) any substance modified by increasing the amount of the substance relative to other components with which it is naturally associated.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide, such that the control sequence directs expression of the coding sequence.

Phe-free or Phe-low: The term "Phe-free" means the protein in question does not contain any Phe groups. The term "Phe-low" means that the protein in question at the most contains 5% Phe groups.

Recombinant host cell: The term "recombinant host cell" or "host cell" is intended to refer to a cell into which a recombinant nucleic acid such as a recombinant vector has been introduced. A recombinant host cell may be an isolated cell or cell line grown in culture or may be a cell which resides in a living tissue or organism.

Sequence identity: as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods.

In the present context, the homology between two amino acid sequences or between two nucleic acid sequences is described by the parameter "identity". Alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6.

Multiple alignments of protein sequences may be made using "ClustalW". Multiple alignments of DNA sequences may be done using the protein alignment as a template, replacing the amino acids with the corresponding codon from the DNA sequence.

Alternatively, different software can be used for aligning amino acid sequences and DNA sequences. The alignment of two amino acid sequences is e.g. determined by using the Needle program from the EMBOSS package (emboss.org) version 2.8.0. The Needle program implements the global alignment algorithm. The substitution matrix used is BLOSUM62, gap opening penalty is 10, and gap extension penalty is 0.5.

The degree of identity between an amino acid sequence; e.g. SEQ ID NO: 7 and a different amino acid sequence (e.g. SEQ ID NO: 76) is calculated as the number of exact matches in an alignment of the two sequences, divided by the length of the "SEQ ID NO: 7" or the length of the "SEQ ID NO: 76", whichever is the shortest. The result is expressed in percent identity.

An exact match occurs when the two sequences have identical amino acid residues in the same positions of the overlap.

If relevant, the degree of identity between two nucleotide sequences can be determined by the Wilbur-Lipman method (51). using the LASER-GENET™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a particular embodiment, the percentage of identity of an amino acid sequence of a polypeptide with, or to, amino acids of SEQ ID NO: 1 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention is calculated in an analogous way.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethyl-homo-cysteine, nitro-glutamine, homoglutamine, pipecolic acid, thiazolidine carboxylic acid, dehydroproline, 3- and 4-methylpróbline, 3,3-dimethylproline, tert-leucine, norvaline, 2-azaphenyl-alanine, 3-azaphenylalanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (52-55). In a second method, translation is carried out in Xenopus oocytes by microinjection of mutated mRNA and chemically aminoacylated suppressor tRNAs (56). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (57). Naturally occurring amino acid residues can be converted to non-naturally occurring species by in vitro chemical modification. Chemical modification can be combined with site-directed mutagenesis to further expand the range of substitutions.

Vector: The term "vector" is intended to refer to a nucleic acid molecule capable of transporting another nucleic acid to which it has been linked. One type of vector is a "plasmid", which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome. Certain vectors are capable of directing the expression of genes to which they are operably linked.

REFERENCES

[1] Kim W, Erlandsen H, Surendran S, et al. Trends in enzyme therapy for phenylketonuria[J]. Mol Ther. 2004, 10(2): 220-224.

[2] en.wikipedia.org/wiki/Phenylketonuria.
[3] pku.com/What-is-PKU/history-of-phenylketonuria.php.
[4] Schuett V E. Celebrating 75 Years Since the Discovery of PKU[J]. National PKU News. 2009, 21(2): 1.
[5] Kochhar J S, Chan S Y, Ong P S, et al. Clinical therapeutics for phenylketonuria[J]. Drug Delivery and Translational Research. 2012, 2(4): 223-237.
[6] Williams R A, Mamotte C D, Burnett J R. Phenylketonuria: an inborn error of phenylalanine metabolism[J]. Clin Biochem Rev. 2008, 29(1): 31-41.
[7] Kaufman S. A model of human phenylalanine metabolism in normal subjects and in phenylketonuric patients [J]. Proc Natl Acad Sci USA. 1999, 96(6): 3160-3164.
[8] van Spronsen F J, Enns G M. Future treatment strategies in phenylketonuria[J]. Mol Genet Metab. 2010, 99 Suppl 1: S90-S95.
[9] Ney D M, Gleason S T, van Calcar S C, et al. Nutritional management of PKU with glycomacropeptide from cheese whey[J]. J Inherit Metab Dis. 2009, 32(1): 32-39.
[10] Lim K, van Calcar S C, Nelson K L, et al. Acceptable low-phenylalanine foods and beverages can be made with glycomacropeptide from cheese whey for individuals with PKU[J]. Mol Genet Metab. 2007, 92(1-2): 176-178.
[11] Macleod E L, Clayton M K, van Calcar S C, et al. Breakfast with glycomacropeptide compared with amino acids suppresses plasma ghrelin levels in individuals with phenylketonuria[J]. Mol Genet Metab. 2010, 100(4): 303-308.
[12] van Calcar S C, Ney D M. Food Products Made with Glycomacropeptide, a Low-Phenylalanine Whey Protein, Provide a New Alternative to Amino Acid—Based Medical Foods for Nutrition Management of Phenylketonuria [J]. Journal of the Academy of Nutrition and Dietetics. 2012, 112(8): 1201-1210.
[13] Ney D M, Hull A K, van Calcar S C, et al. Dietary glycomacropeptide supports growth and reduces the concentrations of phenylalanine in plasma and brain in a murine model of phenylketonuria[J]. J Nutr. 2008, 138(2): 316-322.
[14] Gamez A, Wang L, Straub M, et al. Toward PKU enzyme replacement therapy: PEGylation with activity retention for three forms of recombinant phenylalanine hydroxylase[J]. Mol Ther. 2004, 9(1): 124-129.
[15] Sarkissian C N, Gamez A. Phenylalanine ammonia lyase, enzyme substitution therapy for phenylketonuria, where are we now?[J]. Mol Genet Metab. 2005, 86 Suppl 1: S22-S26.
[16] Gamez A, Sarkissian C N, Wang L, et al. Development of pegylated forms of recombinant Rhodosporidium toruloides phenylalanine ammonia-lyase for the treatment of classical phenylketonuria[J]. Mol Ther. 2005, 11(6): 986-989.
[17] Sarkissian C N, Gamez A, Wang L, et al. Preclinical evaluation of multiple species of PEGylated recombinant phenylalanine ammonia lyase for the treatment of phenylketonuria[J]. Proc Natl Acad Sci USA. 2008, 105(52): 20894-20899.
[18] Sarkissian C N, Kang T S, Gamez A, et al. Evaluation of orally administered PEGylated phenylalanine ammonia lyase in mice for the treatment of Phenylketonuria[J]. Mol Genet Metab. 2011, 104(3): 249-254.
[19] Sarkissian C N, Kang T S, Gamez A, et al. Evaluation of orally administered PEGylated phenylalanine ammonia lyase in mice for the treatment of Phenylketonuria[J]. Mol Genet Metab. 2011, 104(3): 249-254.
[20] Harding C O, Blau N. Advances and challenges in phenylketonuria[J]. J Inherit Metab Dis. 2010, 33(6): 645-648.
[21] Ding Z, Harding C O, Rebuffat A, et al. Correction of murine PKU following AAV-mediated intramuscular expression of a complete phenylalanine hydroxylating system[J]. Mol Ther. 2008, 16(4): 673-681.
[22] Raper S E, Chirmule N, Lee F S, et al. Fatal systemic inflammatory response syndrome in a ornithine transcarbamylase deficient patient following adenoviral gene transfer[J]. Mol Genet Metab. 2003, 80(1-2): 148-158.
[23] Santos-Sierra S, Kirchmair J, Perna A M, et al. Novel pharmacological chaperones that correct phenylketonuria in mice[J]. Hum Mol Genet. 2012, 21(8): 1877-1887.
[24] Haruki H, Pedersen M G, Gorska K I, et al. Tetrahydrobiopterin biosynthesis as an off-target of sulfa drugs [J]. Science. 2013, 340(6135): 987-991.
[25] Muntau A C, Gersting S W. Phenylketonuria as a model for protein misfolding diseases and for the development of next generation orphan drugs for patients with inborn errors of metabolism[J]. J Inherit Metab Dis. 2010, 33(6): 649-658.
[26] Aguado C, Perez B, Ugarte M, et al. Analysis of the effect of tetrahydrobiopterin on PAH gene expression in hepatoma cells[J]. FEBS Lett. 2006, 580(7): 1697-1701.
[27] Pey A L, Perez B, Desviat L R, et al. Mechanisms underlying responsiveness to tetrahydrobiopterin in mild phenylketonuria mutations[J]. Hum Mutat. 2004, 24(5): 388-399.
[28] Pey A L, Ying M, Cremades N, et al. Identification of pharmacological chaperones as potential therapeutic agents to treat phenylketonuria[J]. J Clin Invest. 2008, 118(8): 2858-2867.
[29] Burton B K, Nowacka M, Hennermann J B, et al. Safety of extended treatment with sapropterin dihydrochloride in patients with phenylketonuria: results of a phase 3b study[J]. Mol Genet Metab. 2011, 103(4): 315-322.
[30] Macdonald A, Ahring K, Dokoupil K, et al. Adjusting diet with sapropterin in phenylketonuria: what factors should be considered?[J]. Br J Nutr. 2011, 106(2): 175-182.
[31] Burton B K, Bausell H, Katz R, et al. Sapropterin therapy increases stability of blood phenylalanine levels in patients with BH4-responsive phenylketonuria (PKU) [J]. Mol Genet Metab. 2010, 101(2-3): 110-114.
[32] Harding C O. New era in treatment for phenylketonuria: Pharmacologic therapy with sapropterin dihydrochloride [J]. Biologics. 2010, 4: 231-236.
[33] Henderson M. METHOD OF SYNTHESIZING TETRAHYDROBIOPTERIN[P]. 349479. [Aug. 6, 2009].
[34] Jungles S. Stable Tablet Formulation[P]. 563418. [Nov. 22, 2007].
[35] Shimizu I. Method for Producing Biopterins Using Tetrahydrobiopterin Biosynthesis Enzyme[P]. 795322. [Apr. 23, 2009].
[36] Yabuta M. Process for producing biopterin[P]. 362914. [Jan. 22, 2004].
[37] Hasegawa H. Compsition Containing Biopterin and Method for Using The Same[P]. 225307. [Sep. 16, 2010].
[38] Yamamoto K, Kataoka E, Miyamoto N, et al. Genetic engineering of *Escherichia coli* for production of tetrahydrobiopterin[J]. Metab Eng. 2003, 5(4): 246-254.
[39] Matalon R, Surendran S, Matalon K M, et al. Future role of large neutral amino acids in transport of phenylalanine into the brain[J]. Pediatrics. 2003, 112(6 Pt 2): 1570-1574.

[40] Pietz J, Kreis R, Rupp A, et al. Large neutral amino acids block phenylalanine transport into brain tissue in patients with phenylketonuria[J]. J Clin Invest. 1999, 103(8): 1169-1178.

[41] Demain A L, Vaishnav P. Production of recombinant proteins by microbes and higher organisms[J]. Biotechnol Adv. 2009, 27(3): 297-306.

[42] Ahang Z, Shojaosadat S A, Nikoopour H. Study of Mycoprotein Production Using *Fusarium oxysporum* PTCC 5115 and Reduction of its RNA Content[J]. Pakistan Journal of Nutrition. 2008, 2(7): 240-243.

[43] Mergulhao F J, Summers D K, Monteiro G A. Recombinant protein secretion in *Escherichia coli* [J]. Biotechnol Adv. 2005, 23(3): 177-202.

[44] Ebisu S, Takagi H, Kadowaki K, et al. Production of human epidermal growth factor by *Bacillus brevis* increased with use of a stable plasmid from *B. brevis* 481[J]. Biosci Biotechnol Biochem. 1992, 56(5): 812-813.

[45] Squires C, Lucy P. Vendor voice: a new paradigm for bacterial strain engineering[J]. BioProcess Int. 2008, 6(Suppl 4): 22-27.

[46] Park E H, Shin Y M, Lim Y Y, et al. Expression of glucose oxidase by using recombinant yeast[J]. J Biotechnol. 2000, 81(1): 35-44.

[47] Schmidt F R. Recombinant expression systems in the pharmaceutical industry[J]. Appl Microbiol Biotechnol. 2004, 65(4): 363-372.

[48] Kobayashi K, Kuwae S, Ohya T, et al. High-level expression of recombinant human serum albumin from the methylotrophic yeast *Pichia pastoris* with minimal protease production and activation[J]. J Biosci Bioeng. 2000, 89(1): 55-61.

[49] Xiong A S, Yao Q H, Peng R H, et al. High level expression of a synthetic gene encoding *Peniophora lycii* phytase in methylotrophic yeast *Pichia pastoris* [J]. Appl Microbiol Biotechnol. 2006, 72(5): 1039-1047.

[50] Werten M W, van den Bosch T J, Wind R D, et al. High-yield secretion of recombinant gelatins by *Pichia pastoris*[J]. Yeast. 1999, 15(11): 1087-1096.

[51] Mayer A F, Hellmuth K, Schlieker H, et al. An expression system matures: a highly efficient and cost-effective process for phytase production by recombinant strains of *Hansenula polymorpha*[J]. Biotechnol Bioeng. 1999, 63(3): 373-381.

[52] Ward O P, Qin W M, Dhanjoon J, et al. Physiology and biotechnology of *Aspergillus*[J]. Adv Appl Microbiol. 2006, 58: 1-75.

[53] Durand H, Clanet M, Tiraby G. Genetic improvement of *Trichoderma reesei* for large scale cellulase production [J]. Enzyme and Microbial Technology. 1988, 10(6): 341-346.

[54] Hassouneh W, Christensen T, Chilkoti A. Elastin-like polypeptides as a purification tag for recombinant proteins [J]. Curr Protoc Protein Sci. 2010, Chapter 6: 6-11.

EXAMPLES

Example 1

Proteins with Less Phe Contents From *Bacillus* and Human

From available published information, proteins No. 1 to 10 from *B. subtilis*, No. 11 from human, No. 12 and 13 from *B. licheniformis* have been selected for expression based on their Phe contents or high expression level in its native host (Table 2).

TABLE 2

Proteins selected for recombinant expression in *B. subtilis* and *B. licheniformis*.

| Abbreviation | Full name | Number of amino acids | Number of Phe | Sequence ID NO* |
|---|---|---|---|---|
| ΔPro1 | minor extracellular protease epr region 135-358 | 224 | 3 | No. 1 |
| ΔPro2 | minor extracellular protease vpr region 180-362 | 183 | 3 | No. 2 |
| ΔamyQ | alpha-amylase region 59-239 | 181 | 6 | No. 3 |
| ΔyjeA | secreted deoxyriboendonuclease region 274-461 | 188 | 3 | No. 4 |
| estA | secreted alkaliphilic lipase | 181 | 4 | No. 5 |
| estB | secreted esterase/lipase | 182 | 3 | No. 6 |
| aprE | serine alkaline protease | 275 | 3 | No. 7 |
| amyE | alpha-amylase | 618 | 22 | No. 8 |
| amyL | alpha-amylase | 483 | 20 | No. 9 |
| nprE | extracellular neutral metalloprotease | 301 | 9 | No. 10 |
| ALAB | human alpha-lactalbumin | 123 | 4 | No. 11 |
| BIapr | alkaline protease | 274 | 3 | No. 12 |
| lip | lipase | 174 | 3 | No. 13 |
| EGFP | Enhanced Green Fluorescent Portein | 239 | 13 | No. 14 |

Expression of these Proteins in *Bacillus*

*B. subtilis* strain WB800N and pHT43 and pHT01 vectors (MoBiTec) were used for expression of the recombinant proteins. The pHT43 and pHT01 both are same except that pHT43 contains amyQ signal peptide while pHT01 does not. Cells were routinely grown in LB medium at 37° C. under aeration. Antibiotics were added where appropriate (ampicillin at 100 μg/ml for *E. coli* and chloramphenicol at 10 μg/ml for *B. subtilis*). The Pgrac promoter of pHT01 vector was replaced with Pgrac promoter mutants P100, P223 and P250 for improving expression level, respectively, resulting in the new recombinant plasmids pHT100, pHT223, and pHT250, respectively. The Pgrac promoter of pHT43 vector was replaced with Pgrac promoter mutants P431, P432 and P433, respectively, resulting in the new recombinant plasmids pHT431, pHT432 and pHT433, respectively. All the above vectors use the strong promoter preceding the groESL operon of *Bacillus subtilis* fused to the lac operator allowing their induction by addition of ITPG. The sequences of pHT43, pHT01, P100, P223, P250, P431, P432 and P433 are SEQ ID NOs 14-21, respectively.

The genetic material corresponding to the proteins of interest is the DNA. Most of the genes encoding the proteins of interest are cloned from *B. subtilis* and *B. licheniformis*. Only the gene fragments encoding ALAB and EGFP were artificial synthesis. All the genes are inserted into the vector by restriction enzyme digestion and T4 DNA Ligase ligation. The nucleotide sequences corresponding to the amino acid sequences are SEQ ID NOs 59-72, respectively.

All the PCR products of the candidate genes were double digested with BamH I and Sma I and then ligated into pHT01, pHT43, pHT100, pHT223, pHT250, pHT431, pHT432 and pHT433 vectors, which were digested with the same restriction endonuclease to form the recombinant vectors. The ligated products were first transformed into *E. coli* DH5α, analyzed for the correct insert by DNA sequencing and then introduced into *B. subtilis* WB800N (nprE aprE epr bpr mpr::ble nprB::bsr Δvpr wprA::hyg cm::neo). The protocol of preparation of competent *B. subtilis* cells and electro-transformation were adopted from Xue et al[58], 1992. All the recombinant *B. subtilis* strains grow aerobically at 37° C. in 2× YT medium (16 g tryptone, 10 g casamino acids, 5 g NaCl). When the $OD_{600}$ of recombinant strains reach 0.7-0.8, split the 2× YT medium into 2 portions and induce with 1 mM IPTG to one portion for induction (t=0 h). Collect samples at different time points for analysis (t=2-6 h). The samples were collected by centrifugation for SDS-PAGE analysis.

The expression of estB (lane 2 in FIG. 7), estA (lane 3 in FIG. 8), and aprE (lane 2 in FIG. 9) in B. subtilis WB800N strains with vector pHT43 were all observed on SDS-PAGE, respectively.

The expression levels of aprE in B. subtilis were improved about 10%-300% when using the new recombinant plasmids compared with commercial vectors pHT01 and pHT43. The highest expression level was obtained when using the pHT431 vector. In general, the extracellular expression vectors with an amyQ signal peptide (pHT431, pHT432 and pHT433) are better than intracellular vectors (pHT100, pHT223 and pHT250).

Expression of Recombinant Proteins Without Phe

Three Phe residues in aprE were replaced with Tyr and Leu by site-directed mutagenesis or using a Multipoints Mutagenesis Kit (TaKaRa, Japan), resulting in aprEF50YF189YF261L (maprE). Design the mutative primer and send to synthesis in a china company (tianyibiotech.com). For site-directed mutagenesis, it is a straightforward and simple process, but the mutative sites must be replaced one by one. The main procedure include the following steps: amplify the template plasmids using the synthetic primers, digest the PCR products with DpnI enzyme, transform the purified product into E. coli DH5.alpha. or TOP10, and send 3-5 clones to sequence in a company (tsingke.net). For multipoint mutagenesis at one time, the process is followed the manual of Multipoints Mutagenesis Kit (TaKaRa, Japan). Four Phe residues in estA were replaced with other amino acids by site-directed mutagenesis, resulting in estAF17YF19YF41CF58Y (mestA1) and estAF17WF19YF41CF58Y (mestA2). The human .alpha.-lactalbumin protein containing four Phe residues is the most important nutritive protein of human milk. In order to produce a Phe free ALAB, the first Phe of ALAB is replaced with Met, and all the other Phe residues of ALAB are replaced with Val, resulting in ALABF3MF31VF53VF80V3 (mALAB). All the mutative genes were inserted into pHT43 vector for expression testing in B. subtilis strain WB800. All the recombinant plasmids have been identified by colony PCR and sequencing.

All the mutative genes were confirmed by sequencing (singke.net). The PCR product of all the mutative genes were double digest with BamH I and Sma I, and then ligate them with expression vector pHT43 or other plasmids digested with the same restriction endonuclease. The ligated products were transformed into E. coli DH5.alpha. or TOP10. The positive clones were identified by colony PCR, which is a common method used in molecular biology by using the microcolony as the template of PCR. Then, 3-5 positive clones were sent to sequencing (tsingke.net). The E. coli clones identified with the right plasmids are preserved and used for plasmid extraction. The recombinant shuttle plasmids were further used for electro-transforming into B. subtilis or B. licheniformis. The positive clones were screened by chloramphenicol plate. 4-8 positive clones were pick up and inoculated into 2.times. YT medium for expression. All the recombinant B. subtilis strains grow aerobically at 37.degree. C. in 2.times. YT medium. When the OD600 of recombinant strains reach 0.7-0.8, the 2.times. YT culture is splited into 2 portions. One portion is induced with 1 mM IPTG and the other is used as control without addition of IPTG. Collect samples at different time points for analysis (t=2-6 h). The samples were collected by centrifugation for SDS-PAGE analysis.

Figure 10:
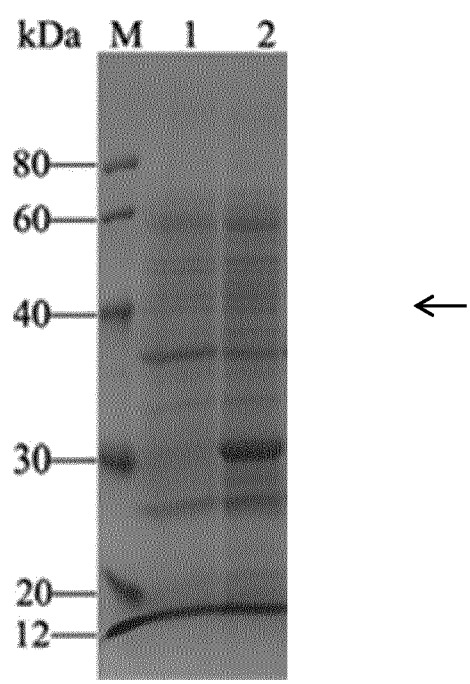

The maprE has been successfully expressed with a 30 kDa brand on SDS-PAGE (FIG. 10). However, the expression of mestA1, mestA2 and mALAB were not observed. The expression levels of mestA1, mestA2 and mALAB were too low.

Methods to Increase the Expression Levels of Recombinant Proteins without Phe

Promoter and secretion signal peptides are usually important for the expression and secretion of a recombinant protein. Expression level has been increase about 3 times by replacing the Pgrac promoter with its mutants and combination with amyQ secretion signal peptide (FIG. 11, pHT432 contains the signal peptide amyQ from B. amyloliquifaciens α-amylase and Pgrac promoter mutant P250, pHT01 does not contain the signal peptide and use Pgrac original promoter).

Expression level has been increase about 3 times by replacing the Pgrac promoter with its mutants and combination with amyQ secretion signal peptide Digestion of Blapr by Pepsin and Trypsin For pepsin digestion test, 20 mg of Blapr protein in 5 ml solution was boiled for 5 min to simulate a cooking process. Then 1 mg of pepsin in 1 ml of solution, pH 2 was added. The reaction mixture was adjusted to pH 2. After 2 hours, sample was taken for mass spectrum analysis. Blapr was fully digested into small peptides (A, FIG. 12)

For trypsin digestion test, 20 mg of Blapr protein in 5 ml solution was boiled for 5 min to simulate a cooking process. Then 1 mg of trypsin in 1 ml of solution, pH 7 was added. The reaction mixture was adjusted to pH 7. After 2 hours, sample was taken for mass spectrum analysis. Blapr was fully digested into small peptides (B, FIG. 12)

Example 2

Production and Purification of Phe-Free Protein
1. Obtain the Genes Encoding Phe-Free Protein Three Phe residues (F50, F189, F261) and one Gln residue (Q19) in aprE of Bacillus subtilis CICC10073 strain were replaced with Trp by standard site-directed mutagenesis PCR or using a Multi-points Mutagenesis Kit (TaKaRa, Japan), resulting in 10073aprE-19W50W189W261W (10073aprE-W7). Four Phe residues (F21, F50, F188, F260) in apr of Bacillus licheniformis CICC10266 strain were replaced with Trp and Tyr by site-directed mutagenesis PCR or using a Multi-points Mutagenesis Kit (TaKaRa, Japan), resulting in 10266apr-21W50Y188W260W (10266apr-W4). All PCR primers were synthesized by a China company (tianyibiotech.com). For site-directed mutagenesis, it is a standard PCR process, but the mutative sites must be replaced one by one. The whole procedure includes the following steps: amplify the template plasmids using the synthetic primers, digest the PCR products with DpnI enzyme, transform the purified product into E. coli DH5.alpha. or TOP10, and send 3-5 clones to sequence by a service company (tsingke.net). For making multi-points mutagenesis at one time, the process is described in the manual of Multi-points Mutagenesis Kit (TaKaRa, Japan). All the mutant genes were confirmed by sequencing (tsingke.net).

2. Knockin 10266apr-W4 Gene into CICC10266 (apr yhfN)
2.1 Initial Host Strain

Bacillus licheniformis CICC10266 (apr yhfN) was used in the construction of the Phe-free production strains for 10266apr-W4 protein. CICC10266 (apr yhfN) is an alkaline protease apr and an intracellular protease yhfN genes defective derivative. *Bacillus licheniformis* CICC10266 (Δapr yhfN) was used in the construction of the Phe-free production strains for 10073aprE-W7 protein. CICC10266 (Δapr yhfN) is an alkaline protease gene deletion and intracellular protease yhfN gene defective derivative.

2.2 Introduced DNA Sequences

The introduced DNA sequences may contain a segment of *B. licheniformis* chromosomal DNA found 5' upstream of the apr gene promoter, a strong apr promoter, the apr signal peptide, the modified alkaline protease, and the 3' downstream of the apr gene. The modified *B. licheniformis* apr gene sequence and the amino acid sequence of the mature Phe-free protein shown in SEQ NO. 73-74.

2.3 Construction of Recombinant *Bacillus licheniformis* with 10266apr-W4 Gene

For developing better bacterial strains that can overproduce the Phe-free protein, the approach generating multiple gene copies in the chromosome of the bacterial strain was used. In the present invention, three distinct sites on the *B. licheniformis* chromosome, apr (alkaline protease locus), xyl (xylose isomerase locus), and gnt (gluconate permease locus) were used as the integration sites. For integrating gene into the three sites, three integrative vectors containing the modified *B. licheniformis* alkaline protease gene were constructed. The method of gene integration in present invention takes advantage of the stimulatory effect of rolling-circle replication of thermo-sensitive plasmids on intramolecular recombination. The plasmid pEBKan194-GFP (FIG. 13), which is naturally temperature sensitive above 42° C., is used for construction of various knockout and knockin vectors. The integrants can be selected on the basis of growth at 42-44° C.

Construction of the three integrative vectors with 10266apr-W4.

First, introduced DNA sequence containing 10266apr-W4 gene was amplified and then inserted into three integrative vectors with the up and down homologous arm gene fragments of apr, xylA, and gntP genes of *B. licheniformis* CICC10266 (pEBkan194-GFP-aprFR1, pEBkan194-GFP-XyIFR, and pEBkan194-GFP-gntPFR) by ClonExpress II One Step Cloning Kit (vazyme.com), respectively, resulting in pEBkan194-GFP-aprFR1-10266apr-W4, pEBkan194-GFP-XyIFR-10266apr-W4, pEBkan194-GFP-gntpFR-10266apr-W4. The products were transformed into *E. coli*. The clones containing the desired plasmids were identified by colony PCR, which is a common method used in molecular biology by using the microcolony as the template of PCR. Then, 3-5 clones were sent to sequencing (tsingke.net). The *E. coli* clones identified with the right plasmids were preserved and used for plasmid extraction. The plasmids were used for electro-transforming into *B. licheniformis* CICC10266 (apr yhfN) strain. The protocol of preparation of competent *B. licheniformis* cells and electro-transformation were adopted from Xue et al. .sup.[1], 1999.

Screening Strains with 10266apr-W4 Gene Integrated

The positive clones were screened by kalamycin resistance plate and green fluorescence. The positive clones were inoculated into 30 mL LB medium and cultured at 42-44° C. Took samples per 8-12 h and identified the homologous single-crossover of integrative vectors and genome of *B. licheniformis* CICC10266 (apr yhfN) strain by colony PCR and sequencing. Then, the single-crossover recombinant clones were further inoculated into 30 mL LB medium and cultured at 42-44° C. Took samples per 8-12 h and plate streaking in kalamycin resistance plate and non-resistance plate. The resistance loss clones were used to identify the homologous double-crossover by colony PCR and sequencing. After confirmation, a marker-free strain with one copy of 10266apr-W4 gene integrated (10266 (yhfN Δapr:: 10266apr-W4) was obtained, which was used as the host strain for further work to integrate more copies.

For integrating more copies of Blapr-W4 gene, the three integrative vectors may be applied one by one. In this invention, two marker-free integrative strains, 10266 (yhfN Δapr::10266apr-W4 xylA::10266ape-W4) and 10266 (yhfN Δapr::10266apr-W4 gntP::10266apr-W4), with two copies of 10266apr-W4 gene were obtained by homologous single-crossover and double-crossover screening as described above. A strain with three copies of the 10266apr-W4 gene will be generated from any of the strains with two copies.

3. Knockin 10073aprE-W7 Gene into CICC10266 (Δapr yhfN)

The whole process for construction of strains to express 10073aprE-W7 is very similar to the described for expression of 10266apr-W4. The introduced DNA sequence containing 10073aprE-W7 gene was amplified and inserted into four knockin vectors with the up and down homologous arm gene fragments of apr, xylA, gntP and ywaD gene of *B. licheniformis* CICC10266 (pEBkan194-GFP-ydeDLC, pEBkan194-GFP-XyIFR, pEB-kan194-GFP-gntPFR and pEBkan194-GFP-ywaDFR) by ClonExpress II One Step Cloning Kit (vazyme.com), resulting in pEBkan194-GFP-aprFR2-10073aprE-W7 (FIG. 14), pEBkan194-GFP-XyIFR-10073aprE-W7 (FIG. 15), pEBkan194-GFP-gntpFR-10073maprEW7 (FIG. 16), pEBkan194-GFP-ywaDFR-10073aprE-W7 (FIG. 17). The positive clones were identified by colony PCR. Then, 3-5 positive clones were sent to sequencing (tsingke.net). The *E. coli* clones identified with the right plasmids were preserved and used for plasmid extraction. The plasmids were then used for electro-transforming into *B. licheniformis* CICC10266 (Lapr yhfN) strain. The protocol of preparation of competent *B. licheniformis* cells and electro-transformation were adopted from Xue et al. .sup.[1], 1999.

The positive clones were screened by kalamycin resistance plate and green fluorescence. The positive clones were inoculated into 30 mL LB medium and cultured at 42-44° C. Took samples per 8-12 h and identified the homologous single-crossover of knockin vectors into the genome of *B. licheniformis* CICC10266 (Δapr yhfN) strain by colony PCR and sequencing. Then, the single-crossover recombinant clones were further inoculated into 30 mL LB medium and cultured at 42-44° C. Took samples per 8-12 h and plate streaking in kalamycin resistance plate and non-resistance plate. The resistance loss clones were used to identify the homologous double-crossover by colony PCR and sequencing. Finally, four marker-free knockin strains with one copy of 10073aprE-W7 gene (10266 (yhfN Δapr.:10073aprE-W7), 10266 (Δapr yhfN xylA::10073aprE-W7), 10266 (Δapr yhfN gntP::10073aprE-W7) and 10266 (Δapr yhfN ywaD::10073aprE-W7)) at each of the four sites were obtained and used as host strains for integrating more copies of 10073apr-W7.

The vectors pEBkan194-GFP-XyIFR-10073aprE-W7 and pEBkan194-GFP-gntpFR-10073maprEW7 were then used for electro-transforming into 10266 (yhfN Δapr.:10073aprE-W7) strain. Two marker-free strains 10266 (yhfN Δapr.: 10073aprE-W7 xylA::10073aprE-W7) and 10266 (yhfN Δapr.:10073aprE-W7 gntP::10073aprE-W7) with two copies of 10073aprE-W7 gene were obtained by homologous single-crossover and double-crossover screening as described above.

The vector pEBkan194-GFP-ywaDFR-10073aprE-W7 was then used for electro-transforming into 10266 (yhfN Δapr.:10073aprE-W7 gntP::10073aprE-W7) strain. Finally, a marker-free strain 10266 (yhfN Δapr.:10073aprE-W7 gntP::10073aprE-W7 ywaD::10073aprE-W7) with three copies of 10073aprE-W7 gene were obtained by homologous single-crossover and double-crossover screening as described above.

4. Expression of 10266apr-W4 and 10073aprE-W7

All the recombinant strains with single and multiple copies of 10266apr-W4 and 10073aprE-W7 genes were used to express protein in shake flask. The positive clones were pick up and inoculated into 10 mL LB medium (Yeast extract 5 g/L, Peptone 10 g/L and NaCl 10 g/L). The recombinant strains were cultured at 37° C. overnight. Then, 2 mL of this pre-culture was used to inoculate 50 mL of the SC1 medium (Soybean cake powder 45 g/L, Corn flour 40 g/L, Yeast extract 2.5 g/L, $K_2HPO_4.3H_2O$ 2.85 g/L, $NaH_2PO_4.2H_2O$ 5.85 g/L, $CaCl_2$, 0.2 g/L and defoamer 1 mL/L) in a 250 mL flask. All the recombinant B. licheniformis strains grew aerobically at 37° C. in SC medium for 24-32 h. Collected samples at different time points for analysis (t=2-6 h). The samples were collected by centrifugation for SDS-PAGE analysis and determination of total protein concentration (Table 3). The protein content was determined via a spectrophotometric method using BSA as a standard[2].

TABLE 3

Expression of 10073aprE-W7 in B. licheniformis system.

| Recombinant strains | Total protein concentration (g/L) |
|---|---|
| CICC10266 (Δapr yhfN) | 0.6 |
| 10266 (yhfN Δapr:: 10073aprE-W7) | 1.04 |
| 10266 (Δapr yhfN xylA:: 10073aprE-W7) | 1.41 |
| 10266 (Δapr yhfN gntP:: 10073aprE-W7) | 1.51 |
| 10266 (Δapr yhfN ywaD:: 10073aprE-W7) | 1.45 |
| 10266 (yhfN Δapr::10073aprE-W7 xylA::10073aprE-W7) | 1.91 |
| 10266 (yhfN Δapr::10073aprE-W7 gntP::10073aprE-W7) | 1.64 |
| 10266 (yhfN Δapr::10073aprE-W7 gntP::10073aprE-W7 ywaD::10073aprE-W7) | 1.43 |
| 10266 (yhfN Δapr:10266apr-W4) | 1.9 |
| 10266 (yhfN Δapr::10266apr-W4 xylA:: 10266ape-W4) | 2.2 |
| 10266 (yhfN Δapr::10266apr-W4 gnfP:: 10266apr-W4) | 2.85 |

5. Production of Phe-Free Protein 10266apr-W4

The YRBLS025 strain (10266 (yhfN Δapr.:10266apr-W4 gntP:: 10266apr-W4)) harboring two copies of 10266apr-W4 gene was used to produce the 10266apr-W4 in fermenter. This strain was streaked on nutrient agar LB medium at 30° C. for 7 days and stored at 4° C.

5.1 Fermentation in 5 L Fermenter

A single clone was picked up from LB plate and inoculated into 10 mL LB medium. The recombinant strains were cultured at 37° C. overnight. Then, 3 ml of this pre-culture was used to inoculate 120 mL of the LB medium in a 500 mL flask, and cultured at 37° C. and 200 rpm. After 10-12 h of culture, the 120 mL seed culture was inoculated into 5 L fermenter with 2.5 L fermentation media SC2 and SC3. The following SC2 and SC3 media were used with the compositions (final concentrations in g/L).

SC2 media: Soybean cake powder 63.6, Corn flour 56, Yeast extract 2.5, $K_2HPO_4.3H_2O$ 2.85, $NaH_2PO_4.2H_2O$ 5.85, $CaCl_2$, 0.2 and defoamer 2 mL/L.

SC3 media: Soybean cake powder 79.4, Corn flour 70.6, Yeast extract 2.5, $K_2HPO_4.3H_2O$ 2.85, $NaH_2PO_4.2H_2O$ 5.85, $CaCl_2$, 0.2 and defoamer 2 mL/L.

Medium pH was adjusted to 7.5 by addition of 1 mol/L NaOH solution before sterilization. The fermentation medium SC2 and SC3 were autoclaved separately for 25 min at 121° C. The cultivation was carried out for 24-36 h at 37° C. with agitation at 200-800 rpm and aeration at 0.4-1 liter $min^{-1}$ $liter^{-1}$. The dissolved oxygen (DO) was controlled at 25%-60%. Collected samples at different time points for analysis (t=2-4 h). The samples were collected by centrifugation for SDS-PAGE analysis and determination of total protein concentration. The 10266apr-W4 has been successfully expressed with a 30 kDa brand on SDS-PAGE (FIG. 18). The total protein concentration achieved 4.44 g/L and 5.19 g/L when using SC2 and SC3 as fermentation media, respectively (Table 4).

TABLE 4

Production of 10266aprE-W4 in 5 L fermnetor with SC2 and SC3 media

| Fermentation | SC2 media | | SC3 media | |
|---|---|---|---|---|
| time (h) | OD600 | Total protein (g/L) | OD600 | Total protein (g/L) |
| 18 | 80.8 | 2.17 | 100.4 | 2.03 |
| 20 | 85 | 2.87 | 108.8 | 3.09 |
| 22 | 82.2 | 3.45 | 109.2 | 3.75 |
| 24 | 83.8 | 4.05 | 116.8 | 4.49 |
| 26 | 82.8 | 4.36 | 113.4 | 5.04 |
| 28 | 84.6 | 4.44 | 113 | 5.19 |
| 36 | 88.3 | 4.22 | 117.6 | 5.06 |

5.2 Fermentation in 50 L Fermentor

A single clone was picked up from LB plate and inoculated into 10 mL LB medium. The recombinant strains were cultured at 37° C. overnight. Then, 3 ml of this pre-culture was used to inoculate 120 mL of the LB medium in a 500 mL flask, and cultured at 37° C. and 200 rpm. After 10-12 h of culture when the OD600 at 12-14, the 80 mL seed culture inoculated into 5 L fermentor with 2.5 L fermentation media SC1. After 8-10 h of culture when the OD600 at 15-17, 1.5 L seed culture was inoculated into 50 L fermenter with 30 L fermentation media SC3.

Medium pH was adjusted to 7.5 by addition of 1 mol/L NaOH solution before sterilization. The fermentation medium SC2 and SC3 were autoclaved separately for 25 min at 121° C. Fermentation was performed in a laboratory 50-liter fermenter (Shanghai Baoxing, china) with a working volume of 30 liter. The cultivation was carried out for 24-36 h at 37° C. with agitation at 200-600 rpm and aeration at 0.4-1 liter $min^{-1}$ $liter^{-1}$. The dissolved oxygen (DO) was controlled at 25%-60%. Collected samples at different time points for analysis (t=2-4 h). The samples were collected by centrifugation for SDS-PAGE analysis and determination of total protein concentration. The 10266apr-W4 has been successfully expressed with a 30 kDa brand on SDS-PAGE (FIG. 19). The total protein concentration achieved 4.91 g/L at 24 h of culture (Table 5).

TABLE 5

Production of 10266aprE-W4 in a 50 L fermenter with SC3 media

| Time (h) | OD600 | Total protein (g/L) |
|---|---|---|
| 12 | 74.8 | 1.9 |
| 14 | 94.8 | 2.23 |
| 16 | 107.3 | 2.89 |
| 18 | 114.8 | 3.54 |

TABLE 5-continued

Production of 10266aprE-W4 in a 50 L fermenter with SC3 media

| Time (h) | OD600 | Total protein (g/L) |
|---|---|---|
| 20 | 117 | 4.09 |
| 22 | 119 | 4.65 |
| 24 | 125 | 4.91 |
| 27 | 122 | 4.76 |

5.3 Fermentation in 500 L Fermenter

A single clone was picked up from LB plate and inoculated into 10 mL LB medium. The recombinant strains were cultured at 37° C. overnight. Then, 3 ml of this pre-culture was used to inoculate 120 mL of the LB medium in a 500 mL flask, and culture at 37° C. and 200 rpm. After 8-10 h of culture when the OD600 at 9-12, the 80 mL seed culture was inoculated into 5 L fermenter with 2.0 L fermentation media SC1. After 6-8 h of culture when the OD600 at 12-16, 1.0 L seed culture was inoculated into 50 L fermenter with 25 L fermentation media SC1. After 7-9 h of culture when the OD600 at 25-27, 20 L seed culture was inoculated into 500 L fermenter with 300 L fermentation media SC3. Medium pH was adjusted to 7.5 by addition of 1 mol/L NaOH solution before sterilization. Fermentation was performed in a laboratory 500-liter fermenter (Shanghai Baoxing, china) with a working volume of 300 L. The cultivation was carried out for 24-36 h at 37° C. with agitation at 200-300 rpm and aeration at 0.4-1 liter min$^{-1}$ liter$^{-1}$. The dissolved oxygen (DO) was controlled at 20%-50%. Collected samples at different time points for analysis (t=2-4 h). The samples were collected by centrifugation for SDS-PAGE analysis and determination of total protein concentration. The 10266apr-W4 has been successfully expressed with a 30 kDa brand on SDS-PAGE (FIG. 20). The total protein concentration achieved 3.89 g/L at 22 h of culture (Table 6).

TABLE 6

Production of 10266aprE-W4 in 50 L fermentor with SC3 media

| Time (h)) | OD600 | Total protein (g/L) |
|---|---|---|
| 20 | 74.2 | 3.78 |
| 22 | 78.2 | 3.89 |
| 25 | 83.6 | 3.51 |

6. Purification of Phe-Free Protein

The purification process was done as following: (1) Collect the culture broth; (2) Collect the filtrate using tangential flow filtration system with 0.1 μm or 0.2 μm ceramic membrane, and then add proper amount pure water to rinse the concentrated fluid. The rinsed fluid was filtered by the same method, collect the filtrate and combine with the previous filtrate; (3) Adjust the pH of filtrate to 1.6±0.15 by 6 M HCl, then make it standing 2-4 hours at room temperature; (4) Discard the supernatant, and pump the remaining solid suspension into the storage tank on the tangential flow system with 50-100 nm ceramic membrane filtration, and then the solid suspension is concentrated to a tenth of the start volume; (5) Use the tangential flow system with 50 nm ceramic membrane to make its pH to 3.5-6 by pure water and concentrate about one eighth or a tenth of the start volume; (6) Drying this concentrate by Centrifugal spray dryer.; (7) Aseptic packaging for finished products.

References for Example 2

[1] Gang-Ping Xue, Jennifer S. Johnson, Brian P. Dalrymple. High osmolarity improves the electro-transformation efficiency of the gram-positive bacteria *Bacillus subtilis* and *Bacillus licheniformis*, Journal of Microbiological Methods, 1999, 34(3):183-191.

[2] Bradford M M. A rapid and sensitive method for the quantitation of microgram quantities of protein utilizing the principle of protein-dye binding. Anal Biochem, 1976, 72:248-254.

---

The invention claimed is:

1. A method for preparing a recombinant Phe-free or Phe-low protein, the method comprising expressing a Phe-free or Phe-low protein from and/or in a *B. licheniformis* expression system and/or a *B. licheniformis* recombinant host cell into which a nucleotide encoding a recombinant Phe-free or Phe-low protein has been inserted into the genome, wherein the amino acid sequence of the Phe-free or Phe-low protein has at least 85% sequence identity with SEQ ID NO:12, and wherein, in the amino acid sequence of the Phe-free or Phe-low protein, 60% or more of the Phe residues of SEQ ID NO:12 have been replaced with one or more large neutral amino acids (LNAAs) selected from Tyr, Trp, Ile, Leu, Val, Met and His.

2. The method according to claim 1, wherein the expression system does not contain any antibiotic genes or any spore-formation genes.

3. The method according to claim 1, wherein the expression system and/or the recombinant host cell is *B. licheniformis* CICC10266.

4. The method according to claim 1, wherein the amino acid sequence of the Phe-free or Phe-low protein has at least 95% sequence identity with SEQ ID NO:12.

5. The method according to claim 1, wherein the amino acid sequence of the Phe-free or Phe-low protein has at least 98% sequence identity with SEQ ID NO:12.

6. The method according to claim 1, wherein, in the amino acid sequence of the Phe-free or Phe-low protein, two of the Phe residues of SEQ ID NO:12 have been replaced with one or more LNAA's selected from Tyr, Trp, Thr, Ile, Leu, Val, Met and His.

7. The method according to claim 1, wherein in the amino acid sequence of the Phe-free or Phe-low protein, all of the Phe residues of SEQ ID NO:12 have been replaced with one or more LNAA's selected from Tyr, Try, Thr, Ile, Leu, Val, Met and His.

8. The method according to claim 1, wherein the protein is Phe-free and wherein the amino acid sequence of the Phe-free protein has at least 75% sequence identity with a sequence selected from SEQ ID NOs 28-30, and SEQ ID NO:76.

9. The method according to claim 8, wherein the protein is Phe-free and wherein the amino acid sequence of the Phe-free protein has at least 85% sequence identity with a sequence selected from SEQ ID NOs 28-30 and SEQ ID NO:76.

10. The method according to claim 9, wherein the protein is Phe-free and wherein the amino acid sequence of the Phe-free protein has at least 95% sequence identity with a sequence selected from SEQ ID NOs 28-30 and SEQ ID NO:76.

11. The method according to claim 10, wherein the protein is Phe-free and wherein the amino acid sequence of the Phe-free protein is selected from SEQ ID NOs 28-30 and SEQ ID NO:76.

12. A recombinant Phe-free protein, wherein the amino acid sequence of the Phe-free protein is selected from sequences having at least 85% sequence identity with SEQ ID NO:12, wherein, in the amino acid sequence of the Phe-free protein, all Phe residues of SEQ ID NO:12 have been replaced with one or more LNAA's selected from Tyr, Trp, Thr, Ile, Leu, Val, Met and His, and sequences having at least 85% sequence identity with SEQ ID NO:28, SEQ ID NO:29, and SEQ ID NO:76.

13. A recombinant Phe-free protein according to claim 12, wherein the amino acid sequence of the Phe-free protein is selected from sequences having at least 95% sequence identity with SEQ ID NO:12 wherein all Phe residues of SEQ ID NO:12 have been replaced with one or more LNAA's selected from Tyr, Trp, Thr, Ile, Leu, Val, Met and His.

14. A recombinant Phe-free protein according to claim 12, wherein, in the amino acid sequence of the Phe-free protein, all Phe in SEQ ID NO:12 have been replaced with one or more LNAA's selected from Tyr, Trp, Thr, Ile, Leu, Val, Met and His.

15. An isolated nucleic acid comprising a nucleic acid sequence that encodes a protein as defined in claim 12.

16. A vector comprising a nucleic acid sequence that encodes a protein as defined in claim 12.

17. A vector according to claim 16, wherein the vector is selected from the group consisting of SEQ ID NO:15 (pHT01), SEQ ID NO:16 (pHT43), SEQ ID NO:17 (pHT100), SEQ ID NO:18 (pHT223), SEQ ID NO:19 (pHT250), SEQ ID NO:20 (pHT431), SEQ ID NO:21 (pHT432) and SEQ ID NO:22 (pHT433).

18. A recombinant microorganism comprising the vector of claim 16, wherein the recombinant microorganism is *B. licheniformis*.

19. A medical food comprising a recombinant Phe-free protein as defined in claim 12.

* * * * *

SEQUENCE LISTING

<160> NUMBER OF SEQ ID NOS: 80

<210> SEQ ID NO 1
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asn Ile Lys Ile Ala Val Ile Asp Ser Gly Ile Ser Pro His Asp Asp
1               5                   10                  15

Leu Ser Ile Ala Gly Gly Tyr Ser Ala Val Ser Tyr Thr Ser Ser Tyr
                20                  25                  30

Lys Asp Asp Asn Gly His Gly Thr His Val Ala Gly Ile Ile Gly Ala
            35                  40                  45

Lys His Asn Gly Tyr Gly Ile Asp Gly Ile Ala Pro Glu Ala Gln Ile
        50                  55                  60

Tyr Ala Val Lys Ala Leu Asp Gln Asn Gly Ser Gly Asp Leu Gln Ser
65                  70                  75                  80

Leu Leu Gln Gly Ile Asp Trp Ser Ile Ala Asn Arg Met Asp Ile Val
                85                  90                  95

Asn Met Ser Leu Gly Thr Thr Ser Asp Ser Lys Ile Leu His Asp Ala

```
                100                 105                 110
Val Asn Lys Ala Tyr Glu Gln Gly Val Leu Leu Val Ala Ala Ser Gly
        115                 120                 125

Asn Asp Gly Asn Gly Lys Pro Val Asn Tyr Pro Ala Ala Tyr Ser Ser
    130                 135                 140

Val Val Ala Val Ser Ala Thr Asn Glu Lys Asn Gln Leu Ala Ser Phe
145                 150                 155                 160

Ser Thr Thr Gly Asp Glu Val Glu Phe Ser Ala Pro Gly Thr Asn Ile
                165                 170                 175

Thr Ser Thr Tyr Leu Asn Gln Tyr Tyr Ala Thr Gly Ser Gly Thr Ser
            180                 185                 190

Gln Ala Thr Pro His Ala Ala Ala Met Phe Ala Leu Leu Lys Gln Arg
        195                 200                 205

Asp Pro Ala Glu Thr Asn Val Gln Leu Arg Glu Met Arg Lys Asn
    210                 215                 220

<210> SEQ ID NO 2
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Lys Gly Ile Lys Val Ala Ile Ile Asp Thr Gly Val Glu Tyr Asn
1               5                   10                  15

His Pro Asp Leu Lys Lys Asn Phe Gly Gln Tyr Lys Gly Tyr Asp Phe
            20                  25                  30

Val Asp Asn Asp Tyr Asp Pro Lys Glu Thr Pro Thr Gly Asp Pro Arg
        35                  40                  45

Gly Glu Ala Thr Asp His Gly Thr His Val Ala Gly Thr Val Ala Ala
    50                  55                  60

Asn Gly Thr Ile Lys Gly Val Ala Pro Asp Ala Thr Leu Leu Ala Tyr
65                  70                  75                  80

Arg Val Leu Gly Pro Gly Gly Ser Gly Thr Thr Glu Asn Val Ile Ala
                85                  90                  95

Gly Val Glu Arg Ala Val Gln Asp Gly Ala Asp Val Met Asn Leu Ser
            100                 105                 110

Leu Gly Asn Ser Leu Asn Asn Pro Asp Trp Ala Thr Ser Thr Ala Leu
        115                 120                 125

Asp Trp Ala Met Ser Glu Val Val Ala Val Thr Ser Asn Gly Asn
    130                 135                 140

Ser Gly Pro Asn Gly Trp Thr Val Gly Ser Pro Gly Thr Ser Arg Glu
145                 150                 155                 160

Ala Ile Ser Val Gly Ala Thr Gln Leu Pro Leu Asn Glu Tyr Ala Val
                165                 170                 175

Thr Phe Gly Ser Tyr Ser Ser
            180

<210> SEQ ID NO 3
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 3

Trp Ser Phe Asn Thr Leu Lys His Asn Met Lys Asp Ile His Asp Ala
1               5                   10                  15

Gly Tyr Thr Ala Ile Gln Thr Ser Pro Ile Asn Gln Val Lys Glu Gly
            20                  25                  30

Asn Gln Gly Asn Lys Ser Met Ser Asn Trp Tyr Trp Leu Tyr Gln Pro
        35                  40                  45

Thr Ser Tyr Gln Ile Gly Asn Arg Tyr Leu Gly Thr Glu Gln Glu Phe
    50                  55                  60

Lys Glu Met Cys Ala Ala Glu Glu Tyr Gly Ile Lys Val Ile Val
65                  70                  75                  80

Asp Ala Val Ile Asn His Thr Thr Ser Asp Tyr Ala Val Ile Ser Asn
                85                  90                  95

Glu Ile Lys Ser Ile Pro Asn Trp Thr His Gly Asn Thr Gln Ile Lys
            100                 105                 110

Asn Trp Ser Asp Arg Trp Asp Val Thr Gln Asn Ser Leu Leu Gly Leu
        115                 120                 125

Tyr Asp Trp Asn Thr Gln Asn Thr Gln Val Gln Ser Tyr Leu Lys Arg
    130                 135                 140

Phe Leu Glu Arg Ala Leu Asn Asp Gly Ala Asp Gly Phe Arg Phe Asp
145                 150                 155                 160

Ala Ala Lys His Ile Glu Leu Pro Asp Asp Gly Ser Tyr Gly Ser Gln
                165                 170                 175

Phe Trp Pro Asn Ile
            180

<210> SEQ ID NO 4
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Pro Asn Gln Lys Val Ile Ala Leu Thr Phe Asp Asp Gly Pro Asn
1               5                   10                  15

Pro Ala Thr Thr Asn Gln Ile Leu Asp Ser Leu Lys Lys Tyr Lys Gly
            20                  25                  30

His Ala Thr Phe Phe Val Leu Gly Ser Arg Val Gln Tyr Tyr Pro Glu
        35                  40                  45

Thr Leu Ile Arg Met Leu Lys Glu Gly Asn Glu Val Gly Asn His Ser
    50                  55                  60

Trp Ser His Pro Leu Leu Thr Arg Leu Ser Val Lys Glu Ala Leu Lys
65                  70                  75                  80

Gln Ile Asn Asp Thr Gln Asp Ile Ile Glu Lys Ile Ser Gly Tyr Arg
                85                  90                  95

Pro Thr Leu Val Arg Pro Pro Tyr Gly Gly Ile Asn Asp Glu Leu Arg
            100                 105                 110

Ser Gln Met Lys Met Asp Val Ala Leu Trp Asp Val Asp Pro Glu Asp
        115                 120                 125

Trp Lys Asp Arg Asn Lys Lys Thr Ile Val Asp Arg Val Met Asn Gln
    130                 135                 140

Ala Gly Asp Gly Arg Thr Ile Leu Ile His Asp Ile Tyr Arg Thr Ser
145                 150                 155                 160
```

Ala Asp Ala Ala Asp Glu Ile Ile Lys Lys Leu Thr Asp Gln Gly Tyr
                165                 170                 175

Gln Leu Val Thr Val Ser Gln Leu Glu Glu Val Lys
            180                 185

<210> SEQ ID NO 5
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Glu His Asn Pro Val Val Met Val His Gly Ile Gly Gly Ala Ser
1               5                   10                  15

Phe Asn Phe Ala Gly Ile Lys Ser Tyr Leu Val Ser Gln Gly Trp Ser
            20                  25                  30

Arg Asp Lys Leu Tyr Ala Val Asp Phe Trp Asp Lys Thr Gly Thr Asn
        35                  40                  45

Tyr Asn Asn Gly Pro Val Leu Ser Arg Phe Val Gln Lys Val Leu Asp
    50                  55                  60

Glu Thr Gly Ala Lys Lys Val Asp Ile Val Ala His Ser Met Gly Gly
65                  70                  75                  80

Ala Asn Thr Leu Tyr Tyr Ile Lys Asn Leu Asp Gly Gly Asn Lys Val
                85                  90                  95

Ala Asn Val Val Thr Leu Gly Gly Ala Asn Arg Leu Thr Thr Gly Lys
            100                 105                 110

Ala Leu Pro Gly Thr Asp Pro Asn Gln Lys Ile Leu Tyr Thr Ser Ile
        115                 120                 125

Tyr Ser Ser Ala Asp Met Ile Val Met Asn Tyr Leu Ser Arg Leu Asp
    130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr Asn
            180

<210> SEQ ID NO 6
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ser Val His Asn Pro Val Val Leu Val His Gly Ile Ser Gly Ala
1               5                   10                  15

Ser Tyr Asn Phe Phe Ala Ile Lys Asn Tyr Leu Ile Ser Gln Gly Trp
            20                  25                  30

Gln Ser Asn Lys Leu Tyr Ala Ile Asp Phe Tyr Asp Lys Thr Gly Asn
        35                  40                  45

Asn Leu Asn Asn Gly Pro Gln Leu Ala Ser Tyr Val Asp Arg Val Leu
    50                  55                  60

Lys Glu Thr Gly Ala Lys Lys Val Asp Ile Val Ala His Ser Met Gly
65                  70                  75                  80

-continued

Gly Ala Asn Thr Leu Tyr Tyr Ile Lys Tyr Leu Gly Gly Asn Lys
              85                  90                  95

Ile Gln Asn Val Val Thr Leu Gly Gly Ala Asn Gly Leu Val Ser Ser
            100                 105                 110

Thr Ala Leu Pro Gly Thr Asp Pro Asn Gln Lys Ile Leu Tyr Thr Ser
            115                 120                 125

Ile Tyr Ser Leu Asn Asp Gln Ile Val Ile Asn Ser Leu Ser Arg Leu
130                 135                 140

Gln Gly Ala Arg Asn Ile Gln Leu Tyr Gly Ile Gly His Ile Gly Leu
145                 150                 155                 160

Leu Ser Asn Ser Gln Val Asn Gly Tyr Ile Lys Glu Gly Leu Asn Gly
                165                 170                 175

Gly Gly Leu Asn Thr Asn
            180

<210> SEQ ID NO 7
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

-continued

Leu Gly Asn Ser Phe Tyr Tyr Gly Lys Gly Leu Ile Asn Val Gln Ala
              260                 265                 270

Ala Ala Gln
        275

<210> SEQ ID NO 8
<211> LENGTH: 618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
            20                  25                  30

Gly Tyr Thr Ala Ile Gln Thr Ser Pro Ile Asn Gln Val Lys Glu Gly
        35                  40                  45

Asn Gln Gly Asp Lys Ser Met Ser Asn Trp Tyr Trp Leu Tyr Gln Pro
    50                  55                  60

Thr Ser Tyr Gln Ile Gly Asn Arg Tyr Leu Gly Thr Glu Gln Glu Phe
65                  70                  75                  80

Lys Glu Met Cys Ala Ala Glu Glu Tyr Gly Ile Lys Val Ile Val
                85                  90                  95

Asp Ala Val Ile Asn His Thr Thr Ser Asp Tyr Ala Ala Ile Ser Asn
                100                 105                 110

Glu Val Lys Ser Ile Pro Asn Trp Thr His Gly Asn Thr Gln Ile Lys
            115                 120                 125

Asn Trp Ser Asp Arg Trp Asp Val Thr Gln Asn Ser Leu Leu Gly Leu
    130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
                180                 185                 190

Phe Trp Pro Asn Ile Thr Asn Thr Ser Ala Glu Phe Gln Tyr Gly Glu
            195                 200                 205

Ile Leu Gln Asp Ser Ala Ser Arg Asp Ala Ala Tyr Ala Asn Tyr Met
    210                 215                 220

Asp Val Thr Ala Ser Asn Tyr Gly His Ser Ile Arg Ser Ala Leu Lys
225                 230                 235                 240

Asn Arg Asn Leu Gly Val Ser Asn Ile Ser His Tyr Ala Ser Asp Val
                245                 250                 255

Ser Ala Asp Lys Leu Val Thr Trp Val Glu Ser His Thr Tyr Ala
                260                 265                 270

Asn Asp Asp Glu Glu Ser Thr Trp Met Ser Asp Asp Ile Arg Leu
            275                 280                 285

Gly Trp Ala Val Ile Ala Ser Arg Ser Gly Ser Thr Pro Leu Phe Phe
    290                 295                 300

Ser Arg Pro Glu Gly Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr

```
            325                 330                 335
Ala Val Asn Arg Phe His Asn Val Met Ala Gly Gln Pro Glu Glu Leu
            340                 345                 350

Ser Asn Pro Asn Gly Asn Asn Gln Ile Phe Met Asn Gln Arg Gly Ser
        355                 360                 365

His Gly Val Val Leu Ala Asn Ala Gly Ser Ser Val Ser Ile Asn
    370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
                405                 410                 415

Arg Ser Val Ala Val Leu Tyr Pro Asp Asp Ile Ala Lys Ala Pro His
                420                 425                 430

Val Phe Leu Glu Asn Tyr Lys Thr Gly Val Thr His Ser Phe Asn Asp
            435                 440                 445

Gln Leu Thr Ile Thr Leu Arg Ala Asp Ala Asn Thr Thr Lys Ala Val
    450                 455                 460

Tyr Gln Ile Asn Asn Gly Pro Glu Thr Ala Phe Lys Asp Gly Asp Gln
465                 470                 475                 480

Phe Thr Ile Gly Lys Gly Asp Pro Phe Gly Lys Thr Tyr Thr Ile Met
                485                 490                 495

Leu Lys Gly Thr Asn Ser Asp Gly Val Thr Arg Thr Glu Lys Tyr Ser
            500                 505                 510

Phe Val Lys Arg Asp Pro Ala Ser Ala Lys Thr Ile Gly Tyr Gln Asn
        515                 520                 525

Pro Asn His Trp Ser Gln Val Asn Ala Tyr Ile Tyr Lys His Asp Gly
    530                 535                 540

Ser Arg Val Ile Glu Leu Thr Gly Ser Trp Pro Gly Lys Pro Met Thr
545                 550                 555                 560

Lys Asn Ala Asp Gly Ile Tyr Thr Leu Thr Leu Pro Ala Asp Thr Asp
                565                 570                 575

Thr Thr Asn Ala Lys Val Ile Phe Asn Asn Gly Ser Ala Gln Val Pro
            580                 585                 590

Gly Gln Asn Gln Pro Gly Phe Asp Tyr Val Leu Asn Gly Leu Tyr Asn
        595                 600                 605

Asp Ser Gly Leu Ser Gly Ser Leu Pro His
    610                 615

<210> SEQ ID NO 9
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Asn Leu Lys Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60
```

-continued

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Arg Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ala
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 10
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
His Ala Ala Ala Thr Gly Ser Gly Thr Thr Leu Lys Gly Ala Thr Val
1               5                   10                  15

Pro Leu Asn Ile Ser Tyr Glu Gly Gly Lys Tyr Val Leu Arg Asp Leu
            20                  25                  30

Ser Lys Pro Thr Gly Thr Gln Ile Ile Thr Tyr Asp Leu Gln Asn Arg
        35                  40                  45

Gln Ser Arg Leu Pro Gly Thr Leu Val Ser Ser Thr Thr Lys Thr Phe
    50                  55                  60

Thr Ser Ser Ser Gln Arg Ala Ala Val Asp Ala His Tyr Asn Leu Gly
65                  70                  75                  80

Lys Val Tyr Asp Tyr Phe Tyr Ser Asn Phe Lys Arg Asn Ser Tyr Asp
                85                  90                  95

Asn Lys Gly Ser Lys Ile Val Ser Ser Val His Tyr Gly Thr Gln Tyr
            100                 105                 110

Asn Asn Ala Ala Trp Thr Gly Asp Gln Met Ile Tyr Gly Asp Gly Asp
        115                 120                 125

Gly Ser Phe Phe Ser Pro Leu Ser Gly Ser Leu Asp Val Thr Ala His
    130                 135                 140

Glu Met Thr His Gly Val Thr Gln Glu Thr Ala Asn Leu Ile Tyr Glu
145                 150                 155                 160

Asn Gln Pro Gly Ala Leu Asn Glu Ser Phe Ser Asp Val Phe Gly Tyr
                165                 170                 175

Phe Asn Asp Thr Glu Asp Trp Asp Ile Gly Glu Asp Ile Thr Val Ser
            180                 185                 190

Gln Pro Ala Leu Arg Ser Leu Ser Asn Pro Thr Lys Tyr Asn Gln Pro
        195                 200                 205

Asp Asn Tyr Ala Asn Tyr Arg Asn Leu Pro Asn Thr Asp Glu Gly Asp
    210                 215                 220

Tyr Gly Gly Val His Thr Asn Ser Gly Ile Pro Asn Lys Ala Ala Tyr
225                 230                 235                 240

Asn Thr Ile Thr Lys Leu Gly Val Ser Lys Ser Gln Gln Ile Tyr Tyr
                245                 250                 255

Arg Ala Leu Thr Thr Tyr Leu Thr Pro Ser Ser Thr Phe Lys Asp Ala
            260                 265                 270

Lys Ala Ala Leu Ile Gln Ser Ala Arg Asp Leu Tyr Gly Ser Thr Asp
        275                 280                 285

Ala Ala Lys Val Glu Ala Ala Trp Asn Ala Val Gly Leu
    290                 295                 300
```

<210> SEQ ID NO 11
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Lys Gln Phe Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Cys Lys Ser Ser
    50                  55                  60

Gln Val Pro Gln Ser Arg Asn Ile Cys Asp Ile Ser Cys Asp Lys Phe
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
                100                 105                 110

Glu Lys Leu Glu Gln Trp Leu Cys Glu Lys Leu
            115                 120
```

<210> SEQ ID NO 12
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Val Lys Val Leu Asn
                85                  90                  95

Ser Ser Gly Ser Gly Ser Tyr Ser Gly Ile Val Ser Gly Ile Glu Trp
                100                 105                 110

Ala Thr Thr Asn Gly Met Asp Val Ile Asn Met Ser Leu Gly Gly Pro
            115                 120                 125

Ser Gly Ser Thr Ala Met Lys Gln Ala Val Asp Asn Ala Tyr Ala Arg
        130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
                180                 185                 190

Ala Glu Leu Glu Val Met Ala Pro Gly Ala Gly Val Tyr Ser Thr Tyr
            195                 200                 205

Pro Thr Ser Thr Tyr Ala Thr Leu Asn Gly Thr Ser Met Ala Ser Pro
        210                 215                 220

His Val Ala Gly Ala Ala Ala Leu Ile Leu Ser Lys His Pro Asn Leu
```

```
225                 230                 235                 240
Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 13
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser His Asn Pro Val Val Met Val His Gly Ile Gly Gly Ala Asp
1               5                   10                  15

Tyr Asn Phe Ile Gly Ile Lys Ser Tyr Leu Gln Ser Gln Gly Trp Thr
                20                  25                  30

Ser Ser Glu Leu Tyr Ala Ile Asn Phe Ile Asp Lys Thr Gly Asn Asn
            35                  40                  45

Ile Asn Asn Ala Pro Arg Leu Ser Glu Tyr Ile Lys Arg Val Leu Asn
        50                  55                  60

Gln Thr Gly Ala Ser Lys Val Asp Ile Val Ala His Ser Met Gly Gly
65                  70                  75                  80

Ala Asn Thr Leu Tyr Tyr Ile Lys Asn Leu Asp Gly Ala Asp Lys Val
                85                  90                  95

Gly His Val Val Thr Leu Gly Gly Ala Asn Arg Leu Val Thr Asn Thr
                100                 105                 110

Ala Pro Gln Asn Asp Lys Ile Ser Tyr Thr Ser Ile Tyr Ser Thr Ser
            115                 120                 125

Asp Tyr Ile Val Leu Asn Ser Leu Ser Lys Leu Asp Gly Ala Asn Asn
        130                 135                 140

Val Gln Ile Ser Gly Val Ser His Val Gly Leu Leu Phe Ser Ser Lys
145                 150                 155                 160

Val Asn Ala Leu Ile Lys Asp Gly Leu Thr Ala Ser Gly Lys
                165                 170

<210> SEQ ID NO 14
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: EGFP

<400> SEQUENCE: 14

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60
```

Phe Ser Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Lys
225                 230                 235

```
<210> SEQ ID NO 15
<211> LENGTH: 7956
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pHT01

<400> SEQUENCE: 15
ttaagttatt ggtatgactg gttttaagcg caaaaaaagt tgcttttttcg tacctattaa    60 tgtatcgttt tagaaaaccg actgtaaaaa gtacagtcgg cattatctca tattataaaa   120
gccagtcatt aggcctatct gacaattcct gaatagagtt cataaacaat cctgcatgat   180
aaccatcaca aacagaatga tgtacctgta agatagcgg taaatatatt gaattacctt   240
tattaatgaa ttttcctgct gtaataatgg gtagaaggta attactatta ttattgatat   300
ttaagttaaa cccagtaaat gaagtccatg gaataataga agagaaaaa gcattttcag   360 gtataggtgt tttgggaaac aatttccccg aaccattata tttctctaca tcagaaaggt   420
ataaatcata aaactctttg aagtcattct ttacaggagt ccaaatacca gagaatgttt   480
tagatacacc atcaaaaatt gtataagtg gctctaactt atcccaataa cctaactctc   540
cgtcgctatt gtaaccagtt ctaaaagctg tatttgagtt tatcacccctt gtcactaaga   600 aaataaatgc agggtaaaat ttatatcctt cttgttttat gtttcggtat aaaacactaa   660
tatcaatttc tgtggttata ctaaaagtcg tttgttggtt caaataatga ttaaatatct   720
cttttctctt ccaattgtct aaatcaattt tattaaagtt catttgatat gcctcctaaa   780
tttttatcta aagtgaattt aggaggctta cttgtctgct ttcttcatta gaatcaatcc   840 tttttaaaa gtcaatatta ctgtaacata aatatatatt ttaaaatat cccactttat   900 ccaattttcg tttgttgaac taatgggtgc tttagttgaa gaataaaaga ccacattaaa   960
aaatgtggtc ttttgtgttt ttttaaagga tttgagcgta gcgaaaaatc cttttctttc  1020
```

```
ttatcttgat aataagggta actattgccg atcgtccatt ccgacagcat cgccagtcac    1080
tatggcgtgc tgctagcgcc attcgccatt caggctgcgc aactgttggg aagggcgatc    1140
ggtgcgggcc tcttcgctat tacgccagct ggcgaaaggg ggatgtgctg caaggcgatt    1200
aagttgggta acgccagggt tttcccagtc acgacgttgt aaaacgacgg ccagtgaatt    1260
cgagctcagg ccttaactca cattaattgc gttgcgctca ctgcccgctt tccagtcggg    1320
aaacctgtcg tgccagctgc attaatgaat cggccaacgc gcggggagag gcggtttgcg    1380
tattgggcgc cagggtggtt tttcttttca ccagtgagac gggcaacagc tgattgccct    1440
tcaccgcctg gccctgagag agttgcagca agcggtccac gctggtttgc cccagcaggc    1500
gaaaatcctg tttgatggtg gttaacggcg ggatataaca tgagctgtct cggtatcgt     1560 cgtatcccac taccgagata tccgcaccaa cgcgcagccc ggactcggta atggcgcgca    1620
ttgcgcccag cgccatctga tcgttggcaa ccagcatcgc agtgggaacg atgccctcat    1680
tcagcatttg catggtttgt tgaaaaccgg acatggcact ccagtcgcct tcccgttccg    1740
ctatcggctg aatttgattg cgagtgagat atttatgcca gccagcagcg cagacgcg     1800 ccgagacaga acttaatggg cccgctaaca gcgcgatttg ctggtgaccc aatgcgacca    1860
gatgctccac gcccagtcgc gtaccgtctt catgggagaa aataatactg ttgatgggtg    1920
tctggtcaga gacatcaaga aataacgccg gaacattagt gcaggcagct tccacagcaa    1980
tggcatcctg gtcatccagc ggatagttaa tgatcagccc actgacgcgt tgcgcgagaa    2040
gattgtgcac cgccgtttta caggcttcga cgccgcttcg ttctaccatc gacaccacca    2100
cgctggcacc cagttgatcg cgcgagatt taatcgccgc gacaatttgc gacggcgcgt     2160
gcagggccag actggaggtg gcaacgccaa tcagcaacga ctgtttgccc gccagttgtt    2220
gtgccacgcg gttgggaatg taattcagct ccgccatcgc cgcttccact ttttcccgcg    2280
ttttcgcaga aacgtggctg gcctggttca ccacgcggga aacggtctga taagagacac    2340
cggcatactc tgcgacatcg tataacgtta ctggtttcat caaaatcgtc tccctccgtt    2400
tgaatatttg attgatcgta accagatgaa gcactctttc cactatccct acagtgttat    2460
ggcttgaaca atcacgaaac aataattggt acgtacgatc tttcagccga ctcaaacatc    2520
aaatcttaca aatgtagtct ttgaaagtat tacatatgta agatttaaat gcaaccgttt    2580
tttcggaagg aaatgatgac ctcgtttcca ccggaattag cttggtacca gctattgtaa    2640
cataatcggt acggggtgtga aaaagctaac ggaaagggga gcggaaaaga atgatgtaag    2700
cgtgaaaaat ttttttatctt atcacttgaa attggaaggg agattcttta ttataagaat    2760
tgtggaattg tgagcggata acaattccca attaaggag gaaggatcct ctagagtcga    2820
cgtcccgggg gcagcccgcc taatgagcgg gctttttttca cgtcacgcgt ccatggagat    2880
ctttgtctgc aactgaaaag tttataccttt acctggaaca aatggttgaa acatacgagg    2940
ctaatatcgg cttattagga atagtccctg tactaataaa atcaggtgga tcagttgatc    3000
agtatatttt ggacgaagct cggaaagaat ttggagatga cttgcttaat tccacaatta    3060
aattaaggga aagaataaag cgatttgatg ttcaaggaat cacggaagaa gatactcatg    3120
ataaagaagc tctaaaacta ttcaataacc ttacaatgga attgatcgaa agggtggaag    3180
gttaatggta cgaaaattag gggatctacc tagaaagcca caaggcgata ggtcaagctt    3240
aaagaaccct tacatggatc ttacagattc tgaaagtaaa gaaacaacag aggttaaaca    3300
aacagaacca aaaagaaaaa aagcattgtt gaaaacaatg aaagttgatg tttcaatcca    3360
```

```
taataagatt aaatcgctgc acgaaattct ggcagcatcc gaagggaatt catattactt    3420
agaggatact attgagagag ctattgataa gatggttgag acattacctg agagccaaaa    3480
aacttttat gaatatgaat taaaaaaag aaccaacaaa ggctgagaca gactccaaac      3540
gagtctgttt ttttaaaaaa aatattagga gcattgaata tatattagag aattaagaaa    3600
gacatgggaa taaaaatatt ttaaatccag taaaaatatg ataagattat ttcagaatat    3660
gaagaactct gtttgttttt gatgaaaaaa caaacaaaaa aaatccacct aacgaatct     3720
caatttaact aacagcggcc aaactgagaa gttaaatttg agaagggaa aaggcggatt     3780
tatacttgta tttaactatc tccatttta cattttatta aaccccatac aagtgaaaat     3840
cctcttttac actgttcctt taggtgatcg cggagggaca ttatgagtga agtaaaccta   3900
aaaggaaata cagatgaatt agtgtattat cgacagcaaa ccactggaaa taaaatcgcc   3960
aggaagagaa tcaaaaaagg gaaagaagaa gtttattatg ttgctgaaac ggaagagaag   4020
atatggacag aagagcaaat aaaaaacttt tctttagaca aatttggtac gcatatacct   4080
tacatagaag gtcattatac aatcttaaat aattacttct ttgattttg gggctatttt    4140
ttaggtgctg aaggaattgc gctctatgct cacctaactc gttatgcata cggcagcaaa   4200
gacttttgct ttcctagtct acaaacaatc gctaaaaaa tggacaagac tcctgttaca    4260
gttagaggct acttgaaact gcttgaaagg tacggtttta tttggaaggt aaacgtccgt   4320
aataaaccca aggataacac agaggaatcc ccgattttta agattagacg taaggttcct   4380
ttgctttcag aagaactttt aaatggaaac cctaatattg aaattccaga tgacgaggaa   4440
gcacatgtaa agaaggcttt aaaaaaggaa aaagagggtc ttccaaaggt tttgaaaaaa   4500
gagcacgatg aattgttaa aaaatgatg gatgagtcag aaacaattaa tattccagag     4560
gccttacaat atgacacaat gtatgaagat atactcagta aaggagaaat tcgaaaagaa   4620
atcaaaaaac aaatacctaa tcctacaaca tcttttgaga gtatatcaat gacaactgaa   4680
gaggaaaaag tcgacagtac tttaaaaagc gaaatgcaaa atcgtgtctc taagccttct   4740
tttgataccct ggtttaaaaa cactaagatc aaaattgaaa ataaaaattg tttattactt   4800
gtaccgagtg aatttgcatt tgaatggatt aagaaaagat atttagaaac aattaaaaca   4860
gtccttgaag aagctggata tgttttcgaa aaaatcgaac taagaaaagt gcaataaact   4920
gctgaagtat ttcagcagtt ttttttattt agaaatagtg aaaaaatat aatcagggag    4980
gtatcaatat ttaatgagta ctgatttaaa tttatttaga ctggaattaa taattaacac   5040
gtagactaat taaaatttaa tgagggataa agaggataca aaaatattaa tttcaatccc   5100
tattaaattt taacaagggg gggattaaaa tttaattaga ggtttatcca caagaaaaga   5160
ccctaataaa atttttacta gggttataac actgattaat ttcttaatgg gggagggatt   5220
aaaatttaat gacaaagaaa acaatctttt aagaaaagct tttaaaagat aataataaaa   5280
agagctttgc gattaagcaa aactcttac ttttcattg acattatcaa attcatcgat     5340
ttcaaattgt tgttgtatca taaagttaat tctgttttgc acaaccttt caggaatata   5400
aaacacatct gaggcttgtt ttataaactc agggtcgcta aagtcaatgt aacgtagcat   5460
atgatatggt atagcttcca cccaagttag cctttctgct tcttctgaat gttttttcata  5520
tacttccatg ggtatctcta atgattttc ctcatgtagc aaggtatgag caaaaagttt    5580
atggaattga tagttcctct ctttttcttc aactttttta tctaaaacaa acactttaac   5640
atctgagtca atgtaagcat aagatgtttt tccagtcata atttcaatcc caatctttt    5700
agacagaaat tctggacgta aatctttttgg tgaaagaatt tttttatgta gcaatatatc   5760
```

-continued

```
cgatacagca ccttctaaaa gcgttggtga ataggggcatt ttacctatct cctctcattt      5820
tgtggaataa aaatagtcat attcgtccat ctacctatcc tattatcgaa cagttgaact      5880
ttttaatcaa ggatcagtcc ttttttttcat tattcttaaa ctgtgctctt aactttaaca     5940
actcgatttg ttttccaga tctcgagggt aactagcctc gccgatcccg caagaggccc       6000
ggcagtcagg tggcactttt cggggaaatg tgcgcggaac ccctatttgt ttattttctct      6060
aaatacattc aaatatgtat ccgctcatga gacaataacc ctgataaatg cttcaataat      6120
attgaaaaag gaagagtatg agtattcaac atttccgtgt cgcccttatt ccctttttg       6180
cggcattttg ccttcctgtt tttgctcacc cagaaacgct ggtgaaagta aaagatgctg      6240
aagatcagtt gggtgcacga gtgggttaca tcgaactgga tctcaacagc ggtaagatcc      6300
ttgagagttt cgccccgaa gaacgttttc caatgatgag cacttttaaa gttctgctat      6360
gtggcgcggt attatcccgt attgacgccg ggcaagagca actcggtcgc cgcatacact      6420
attctcagaa tgacttggtt gagtactcac cagtcacaga aaagcatctt acggatggca     6480
tgacagtaag agaattatgc agtgctgcca taaccatgag tgataacact gcggccaact      6540
tacttctgac aacgatcgga ggaccgaagg agctaaccgc ttttttgcac aacatggggg      6600
atcatgtaac tcgccttgat cgttgggaac cggagctgaa tgaagccata ccaaacgacg      6660
agcgtgacac cacgatgcct gtagcaatgg caacaacgtt gcgcaaacta ttaactggcg      6720
aactacttac tctagcttcc cggcaacaat taatagactg gatggaggcg gataaagttg      6780
caggaccact tctgcgctcg gcccttccgg ctggctggtt tattgctgat aaatctggag      6840
ccggtgagcg tgggtctcgc ggtatcattg cagcactggg gccagatggt aagccctccc      6900
gtatcgtagt tatctacacg acggggagtc aggcaactat ggatgaacga aatagacaga     6960
tcgctgagat aggtgcctca ctgattaagc attggtaact gtcagaccaa gtttactcat      7020
atatacttta gattgattta aaacttcatt tttaatttaa aaggatctag gtgaagatcc      7080
tttttgataa tctcatgacc aaaatccctt aacgtgagtt ttcgttccac tgagcgtcag      7140
accccgtaga aaagatcaaa ggatcttctt gagatccttt ttttctgcgc gtaatctgct      7200
gcttgcaaac aaaaaaacca ccgctaccag cggtggtttg tttgccggat caagagctac     7260
caactctttt tccgaaggta actggcttca gcagagcgca gataccaaat actgtccttc      7320
tagtgtagcc gtagttaggc caccacttca agaactctgt agcaccgcct acatacctcg     7380
ctctgctaat cctgttacca gtggctgctg ccagtggcga taagtcgtgt cttaccgggt     7440
tggactcaag acgatagtta ccggataagg cgcagcggtc gggctgaacg gggggttcgt      7500
gcacacagcc cagcttggag cgaacgacct acaccgaact gagataccta cagcgtgagc      7560
tatgagaaag cgccacgctt cccgaaggga gaaaggcgga caggtatccg gtaagcggca      7620
gggtcggaac aggagagcgc acgagggagc ttccagggggg aaacgcctgg tatctttata     7680
gtcctgtcgg gtttcgccac ctctgacttg agcgtcgatt tttgtgatgc tcgtcagggg     7740
ggcggagcct atggaaaaac gccagcaacg cggccttttt acggttcctg gccttttgct     7800
ggccttttgc tcacatgttc tttcctgcgt tatcccctga ttctgtggat aaccgtatta      7860
ccgcctttga gtgagctgat accgctcgcc gcagccgaac gaccgagcgc agcgagtcag     7920
tgagcgagga agcggaagag cgcccaatac gcatgc                               7956
```

<210> SEQ ID NO 16
<211> LENGTH: 8057
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pHT43

<400> SEQUENCE: 16

```
ttaagttatt ggtatgactg gttttaagcg caaaaaaagt tgcttttccg tacctattaa      60
tgtatcgttt tagaaaaccg actgtaaaaa gtacagtcgg cattatctca tattataaaa     120
gccagtcatt aggcctatct gacaattcct gaatagagtt cataaacaat cctgcatgat     180
aaccatcaca aacagaatga tgtacctgta aagatagcgg taaatatatt gaattacctt     240
tattaatgaa ttttcctgct gtaataatgg gtagaaggta attactatta ttattgatat     300
ttaagttaaa cccagtaaat gaagtccatg gaataataga aagagaaaaa gcattttcag     360
gtataggtgt tttgggaaac aatttccccg aaccattata tttctctaca tcagaaaggt     420
ataaatcata aaactctttg aagtcattct ttacaggagt ccaaatacca gagaatgttt     480
tagatacacc atcaaaaatt gtataaagtg gctctaactt atcccaataa cctaactctc     540
cgtcgctatt gtaaccagtt ctaaaagctg tatttgagtt tatcacccct gtcactaaga     600
aaataaatgc agggtaaaat ttatatcctt cttgttttat gtttcggtat aaaacactaa     660
tatcaatttc tgtggttata ctaaaagtcg tttgttggtt caataatga ttaaatatct     720
cttttctctt ccaattgtct aaatcaattt tattaaagtt catttgatat gcctcctaaa     780
tttttatcta aagtgaattt aggaggctta cttgtctgct ttcttcatta gaatcaatcc     840
ttttttaaaa gtcaatatta ctgtaacata aatatatatt ttaaaaatat cccactttat     900
ccaattttcg tttgttgaac taatgggtgc tttagttgaa gaataaagac cacattaaaa     960
aatgtggtct tttgtgtttt tttaaaggat ttgagcgtag cgaaaaatcc ttttctttct    1020
tatcttgata ataagggtaa ctattgccga tcgtccattc cgacagcatc gccagtcact    1080
atggcgtgct gctagcgcca ttcgccattc aggctgcgca actgttggga agggcgatcg    1140
gtgcgggcct cttcgctatt acgccagctg gcgaaagggg gatgtgctgc aaggcgatta    1200
agttgggtaa cgccagggtt ttcccagtca cgacgttgta aaacgacggc cagtgaattc    1260
gagctcaggc cttaactcac attaattgcg ttgcgctcac tgcccgcttt ccagtcggga    1320
aacctgtcgt gccagctgca ttaatgaatc ggccaacgcg cggggagagg cggtttgcgt    1380
attgggcgcc agggtggttt ttcttttcac cagtgagacg ggcaacagct gattgccctt    1440
caccgcctgg ccctgagaga gttgcagcaa gcggtccacg ctggtttgcc ccagcaggcg    1500
aaaatcctgt ttgatggtgg ttgacggcgg gatataacat gagctgtctt cggtatcgtc    1560
gtatcccact accgagatat ccgcaccaac gcgcagcccg gactcggtaa tggcgcgcat    1620
tgcgcccagc gccatctgat cgttggcaac cagcatcgca gtgggaacga tgccctcatt    1680
cagcatttgc atggtttgtt gaaaaccgga catggcactc cagtcgcctt cccgttccgc    1740
tatcggctga atttgattgc gagtgagata tttatgccag ccagccagac gcagacgcgc    1800
cgagacagaa cttaatgggc ccgctaacag cgcgatttgc tggtgaccca atgcgaccag    1860
atgctccacg cccagtcgcg taccgtcttc atgggagaaa ataatactgt tgatgggtgt    1920
ctggtcagag acatcaagaa ataacgccgg aacattagtg caggcagctt ccacagcaat    1980
ggcatcctgg tcatccagcg gatagttaat gatcagccca ctgacgcgtt gcgcgagaag    2040
attgtgcacc gccgctttac aggcttcgac gccgcttcgt tctaccatcg acaccaccac    2100
```

```
gctggcaccc agttgatcgg cgcgagattt aatcgccgcg acaatttgcg acggcgcgtg    2160
cagggccaga ctggaggtgg caacgccaat cagcaacgac tgtttgcccg ccagttgttg    2220
tgccacgcgg ttgggaatgt aattcagctc cgccatcgcc gcttccactt tttcccgcgt    2280
tttcgcagaa acgtggctgg cctggttcac cacgcgggaa acggtctgat aagagacacc    2340
ggcatactct gcgacatcgt ataacgttac tggtttcatc aaaatcgtct ccctccgttt    2400
gaatatttga ttgatcgtaa ccagatgaag cactctttcc actatcccta cagtgttatg    2460
gcttgaacaa tcacgaaaca ataattggta cgtacgatct ttcagccgac tcaaacatca    2520
aatcttacaa atgtagtctt tgaaagtatt acatatgtaa gatttaaatg caaccgtttt    2580
ttcggaagga aatgatgacc tcgtttccac cggaattagc ttggtaccag ctattgtaac    2640
ataatcggta cggggtgaa aaagctaacg gaaagggag cggaaaagaa tgatgtaagc    2700
gtgaaaaatt ttttatctta tcacttgaaa ttggaaggga gattctttat tataagaatt    2760
gtggaattgt gagcggataa caattcccaa ttaaaggagg aaggatcaat gattcaaaaa    2820
cgaaagcgga cagtttcgtt cagacttgtg cttatgtgca cgctgttatt tgtcagtttg    2880
ccgattacaa aaacatcagc cgtaggatcc tctagagtcg acgtcccgg ggcagcccgc    2940 ctaatgagcg ggctttttc acgtcacgcg tccatgagaa tctttgtctg caactgaaaa    3000
gtttatacct tacctggaac aaatggttga acatacgag gctaatatcg gcttattagg    3060
aatagtccct gtactaataa aatcaggtgg atcagttgat cagtatattt tggacgaagc    3120
tcggaaagaa tttggagatg acttgcttaa ttccacaatt aaattaaggg aaagaataaa    3180
gcgatttgat gttcaaggaa tcacggaaga agatactcat gataaagaag ctctaaaact    3240
attcaataac cttacaatgg aattgatcga aagggtggaa ggttaatggt acgaaaatta    3300
ggggatctac ctagaaagcc acaaggcgat aggtcaagct taaagaaccc ttacatggat    3360
cttacagatt ctgaaagtaa agaaacaaca gaggttaaac aaacagaacc aaaaagaaaa    3420
aaagcattgt tgaaaacaat gaaagttgat gtttcaatcc ataataagat taaatcgctg    3480
cacgaaattc tggcagcatc cgaagggaat tcatattact tagaggatac tattgagaga    3540
gctattgata gatggttga gacattacct gagagccaaa aaacttttta tgaatatgaa    3600 ttaaaaaaa gaaccaacaa aggctgagac agactccaaa cgagtctgtt tttttaaaaa    3660
aaatattagg agcattgaat atatattaga gaattaagaa agacatggga ataaaaatat    3720
tttaaatcca gtaaaaatat gataagatta tttcagaata tgaagaactc tgtttgtttt    3780
tgatgaaaaa acaaacaaaa aaaatccacc taacggaatc tcaatttaac taacagcggc    3840
caaactgaga agttaaattt gagaagggga aaaggcggat ttatacttgt atttaactat    3900
ctccatttta acattttatt aaaccccata caagtgaaaa tcctcttta cactgttcct    3960 ttaggtgatc gcggagggac attatgagtg aagtaaacct aaaaggaaat acagatgaat    4020
tagtgtatta tcgacagcaa accactggaa ataaaatcgc caggaagaga atcaaaaaag    4080
ggaaagaaga agtttattat gttgctgaaa cggaagagaa gatatggaca gaagagcaaa    4140
taaaaaactt ttctttagac aaatttggta cgcatatacc ttacatagaa ggtcattata    4200
caatcttaaa taattacttc tttgattttt ggggctattt tttaggtgct gaaggaattg    4260
cgctctatgc tcacctaact cgttatgcat acggcagcaa agacttttgc tttcctagtc    4320
tacaaacaat cgctaaaaaa atggacaaga ctcctgttac agttagaggc tacttgaaac    4380
tgcttgaaag gtacggtttt atttggaagg taaacgtccg taataaaacc aaggataaca    4440
cagaggaatc cccgattttt aagattagac gtaaggttcc tttgctttca gaagaacttt    4500
```

```
taaatggaaa ccctaatatt gaaattccag atgacgagga agcacatgta aagaaggctt    4560
taaaaaagga aaagagggt cttccaaagg ttttgaaaaa agagcacgat gaatttgtta    4620
aaaaaatgat ggatgagtca gaaacaatta atattccaga ggccttacaa tatgacacaa    4680
tgtatgaaga tatactcagt aaaggagaaa ttcgaaaaga aatcaaaaaa caaataccta    4740
atcctacaac atcttttgag agtatatcaa tgacaactga agaggaaaaa gtcgacagta    4800
ctttaaaaag cgaaatgcaa aatcgtgtct ctaagccttc ttttgatacc tggtttaaaa    4860
acactaagat caaaattgaa ataaaaatt gtttattact tgtaccgagt gaatttgcat     4920
ttgaatggat taagaaaaga tatttagaaa caattaaaac agtccttgaa gaagctggat    4980
atgttttcga aaaaatcgaa ctaagaaaag tgcaataaac tgctgaagta tttcagcagt    5040 ttttttatt tagaaatagt gaaaaaaata taatcaggga ggtatcaata tttaatgagt     5100
actgatttaa atttatttag actggaatta ataattaaca cgtagactaa ttaaaattta    5160
atgagggata aagaggatac aaaaatatta atttcaatcc ctattaaatt ttaacaaggg    5220
ggggattaaa atttaattag aggtttatcc acaagaaaag accctaataa aattttact    5280 agggttataa cactgattaa tttcttaatg ggggagggat taaaatttaa tgacaaagaa    5340
aacaatcttt taagaaaagc ttttaaaaga taataataaa aagagctttg cgattaagca    5400
aaactcttta cttttttcatt gacattatca aattcatcga tttcaaattg ttgttgtatc    5460
ataaagttaa ttctgttttg cacaaccttt tcaggaatat aaaacacatc tgaggcttgt    5520
tttataaact cagggtcgct aaagtcaatg taacgtagca tatgatatgg tatagcttcc    5580
acccaagtta gccttttctgc ttcttctgaa tgttttttcat atacttccat gggtatctct    5640
aaatgatttt cctcatgtag caaggtatga gcaaaaagtt tatggaattg atagttcctc    5700 tcttttctt caactttttt atctaaaaca aacactttaa catctgagtc aatgtaagca    5760
taagatgttt ttccagtcat aatttcaatc ccaaatcttt tagacagaaa ttctggacgt    5820
aaatcttttg gtgaaagaat ttttttatgt agcaatatat ccgatacagc accttctaaa    5880
agcgttggtg aatagggcat tttacctatc tcctctcatt ttgtggaata aaaatagtca    5940
tattcgtcca tctacctatc ctattatcga acagttgaac ttttaatca aggatcagtc     6000 cttttttca ttattcttaa actgtgctct taactttaac aactcgattt gttttttccag    6060 atctcgaggg taactagcct cgccgatccc gcaagaggcc cggcagtcag gtggcacttt    6120
tcggggaaat gtgcgcggaa cccctatttg tttatttttc taaatacatt caaatatgta    6180
tccgctcatg agacaataac cctgataaat gcttcaataa tattgaaaaa ggaagagtat    6240
gagtattcaa catttccgtg tcgcccttat tcccttttt gcggcatttt gccttcctgt     6300
ttttgctcac ccagaaacgc tggtgaaagt aaaagatgct gaagatcagt tgggtgcacg    6360
agtgggttac atcgaactgg atctcaacag cggtaagatc cttgagagtt ttcgccccga    6420
agaacgtttt ccaatgatga gcacttttaa agttctgcta tgtggcgcgg tattatcccg    6480
tattgacgcc gggcaagagc aactcggtcg ccgcatacac tattctcaga atgacttggt    6540
tgagtactca ccagtcacag aaaagcatct tacggatggc atgacagtaa gagaattatg    6600
cagtgctgcc ataaccatga gtgataacac tgcggccaac ttacttctga caacgatcgg    6660
aggaccgaag gagctaaccg cttttttgca acatgggg gatcatgtaa ctcgccttga    6720
tcgttgggaa ccggagctga atgaagccat accaaacgac gagcgtgaca ccacgatgcc    6780
tgtagcaatg gcaacaacgt tgcgcaaact attaactggc gaactactta ctctagcttc    6840
```

-continued

```
ccggcaacaa ttaatagact ggatggaggc ggataaagtt gcaggaccac ttctgcgctc      6900
ggcccttccg gctggctggt ttattgctga taaatctgga gccggtgagc gtgggtctcg      6960
cggtatcatt gcagcactgg ggccagatgg taagccctcc cgtatcgtag ttatctacac      7020
gacggggagt caggcaacta tggatgaacg aaatagacag atcgctgaga taggtgcctc      7080
actgattaag cattggtaac tgtcagacca agtttactca tatatacttt agattgattt      7140
aaaacttcat ttttaattta aaaggatcta ggtgaagatc cttttttgata atctcatgac      7200 caaaatccct taacgtgagt tttcgttcca ctgagcgtca gaccccgtag aaaagatcaa      7260
aggatcttct tgagatcctt tttttctgcg cgtaatctgc tgcttgcaaa caaaaaaacc      7320
accgctacca gcggtggttt gtttgccgga tcaagagcta ccaactcttt ttccgaaggt      7380
aactggcttc agcagagcgc agataccaaa tactgtcctt ctagtgtagc cgtagttagg      7440
ccaccacttc aagaactctg tagcaccgcc tacatacctc gctctgctaa tcctgttacc      7500
agtggctgct gccagtggcg ataagtcgtg tcttaccggg ttggactcaa gacgatagtt      7560
accggataag gcgcagcggt cgggctgaac ggggggttcg tgcacacagc ccagcttgga      7620
gcgaacgacc tacaccgaac tgagatacct acagcgtgag ctatgagaaa gcgccacgct      7680
tcccgaaggg agaaaggcgg acaggtatcc ggtaagcggc agggtcggaa caggagagcg      7740
cacgagggag cttccagggg gaaacgcctg gtatctttat agtcctgtcg ggtttcgcca      7800
cctctgactt gagcgtcgat ttttgtgatg ctcgtcaggg gggcggagcc tatggaaaaa      7860
cgccagcaac gcggcctttt tacggttcct ggccttttgc tggccttttg ctcacatgtt      7920
ctttcctgcg ttatcccctg attctgtgga taaccgtatt accgcctttg agtgagctga      7980
taccgctcgc cgcagccgaa cgaccgagcg cagcgagtca gtgagcgagg aagcggaaga      8040
gcgcccaata cgcatgc                                                    8057
```

```
<210> SEQ ID NO 17
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P100

<400> SEQUENCE: 17
ggtaccaaag gaggtaagga tcactagaaa attttttaaa aaatctcttg acattggaag       60
ggagatatgt tattataaga attgcggaat tgtgagcgga taacaattcc catataaagg      120
aggaaggatc c                                                           131

<210> SEQ ID NO 18
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P223

<400> SEQUENCE: 18
ggtaccaaag gaggtaagga tcactagaaa attttttaaa aaatctcttg acattggaag       60
ggagatatgt tataataaga atttgtggat tgtgagcgga tcacaattcc acaaccaaca      120
ccaattaaag gaggaaggat cc                                               142
```

<210> SEQ ID NO 19
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P250

<400> SEQUENCE: 19
ggtaccaaag gaggtaagga tcactagaaa attttttaaa aaatctcttg acattggaag      60
ggagatatgt tattataaga atttgtggat tgtgagcgga tcacaattcc acaaccaaca     120
ccaattaaag gaggaaggat cc                                              142

<210> SEQ ID NO 20
<211> LENGTH: 291
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P431

<400> SEQUENCE: 20
ggtaccaaag gaggtaagga tcactagaaa attttttaaa aaatctcttg acattggaag      60
ggagatatgt tattataaga attgcggaat tgtgagcgga taacaattcc catataaagg     120
aggaaggatc aatgattcaa aaacgaaagc ggacagtttc gttcagactt gtgcttatgt     180
gcacgctgtt atttgtcagt ttgccgatta caaaaacatc agccgtagga tccatgtcta     240
gagtcgacgt cgctcatcac catcaccatc accatcacta acgtccccgg g             291

<210> SEQ ID NO 21
<211> LENGTH: 302
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P432

<400> SEQUENCE: 21
ggtaccaaag gaggtaagga tcactagaaa attttttaaa aaatctcttg acattggaag      60
ggagatatgt tattataaga atttgtggat tgtgagcgga tcacaattcc acaaccaaca     120
ccaattaaag gaggaaggat caatgattca aaaacgaaag cggacagttt cgttcagact     180
tgtgcttatg tgcacgctgt tatttgtcag tttgccgatt acaaaaacat cagccgtagg     240
atccatgtct agagtcgacg tcgctcatca ccatcaccat caccatcact aacgtccccg     300
gg                                                                    302

<210> SEQ ID NO 22
<211> LENGTH: 302
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P433

<400> SEQUENCE: 22

```
ggtaccaaag gaggtaagga tcactagaaa attttttaaa aaatctcttg acattggaag      60
ggagatatgt tataataaga atttgtggat tgtgagcgga tcacaattcc acaaccaaca     120
ccaattaaag gaggaaggat caatgattca aaaacgaaag cggacagttt cgttcagact     180
tgtgcttatg tgcacgctgt tatttgtcag tttgccgatt acaaaaacat cagccgtagg     240
atccatgtct agagtcgacg tcgctcatca ccatcaccat caccatcact aacgtccccg     300
gg                                                                   302
```

<210> SEQ ID NO 23
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: encoding the signal peptide of amyQ

<400> SEQUENCE: 23

```
atgattcaaa aacgaaagcg gacagtttcg ttcagacttg tgcttatgtg cacgctgtta      60
tttgtcagtt tgccgattac aaaaacatca gcc                                  93
```

<210> SEQ ID NO 24
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: encoding the native signal of aprE

<400> SEQUENCE: 24

```
gtgagaagca aaaaattgtg gatcagcttg ttgtttgcgt taacgttaat ctttacgatg      60
gcgttcagca acatgtctgc gcaggct                                         87
```

<210> SEQ ID NO 25
<211> LENGTH: 45
<212> TYPE: PRT
<213> ORGANISM: Bacillus subtilis
<220> FEATURE:
<223> OTHER INFORMATION: PDB code 2B9K

<400> SEQUENCE: 25

```
Ala Ile Lys Leu Val Gln Ser Pro Asn Gly Asn Phe Ala Ala Ser Phe
1               5                   10                  15

Val Leu Asp Gly Thr Lys Trp Ile Phe Lys Tyr Tyr Asp Ser Ser Lys
            20                  25                  30

Gly Tyr Trp Val Gln Ile Tyr Glu Val Trp Asp Arg Lys
        35                  40                  45
```

<210> SEQ ID NO 26
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: aprE50Y189Y261L

<400> SEQUENCE: 26

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Tyr Val Pro Ser Glu Thr Asn Pro Tyr Gln Asp Gly Ser Ser His
50                  55                  60

Gly Thr His Val Ala Gly Thr Ile Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
                100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Tyr Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Leu Tyr Tyr Gly Lys Gly Leu Ile Asn Val Gln Ala
                260                 265                 270

Ala Ala Gln
        275

<210> SEQ ID NO 27
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 7:
      aprE50Y189Y261LCC

<400> SEQUENCE: 27

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Tyr Val Pro Ser Glu Thr Asn Pro Tyr Gln Asp Gly Ser Ser His

```
                 50                  55                  60

Gly Thr His Val Ala Gly Thr Ile Ala Ala Leu Asn Asn Ser Ile Gly
 65                  70                  75                  80

Val Leu Gly Val Ala Pro Ser Ala Ser Leu Tyr Ala Val Lys Val Leu
                     85                  90                  95

Asp Ser Thr Gly Ser Gly Gln Tyr Ser Trp Ile Ile Asn Gly Ile Glu
                    100                 105                 110

Trp Ala Ile Ser Asn Asn Met Asp Val Ile Asn Met Ser Leu Gly Gly
                115                 120                 125

Pro Thr Gly Ser Thr Ala Leu Lys Thr Val Val Asp Lys Ala Val Ser
            130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                    165                 170                 175

Val Gly Ala Val Asn Ser Ser Asn Gln Arg Ala Ser Tyr Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                    245                 250                 255

Leu Gly Asn Ser Leu Tyr Tyr Gly Lys Gly Leu Ile Asn Val Gln Ala
                260                 265                 270

Ala Ala Gln Cys Cys
            275

<210> SEQ ID NO 28
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 12:
      Blapr58Y188Y260W

<400> SEQUENCE: 28

Ala Gln Thr Val Pro Tyr Gly Ile Pro Leu Ile Lys Ala Asp Lys Val
  1               5                  10                  15

Gln Ala Gln Gly Tyr Lys Gly Ala Asn Val Lys Val Ala Val Leu Asp
                 20                  25                  30

Thr Gly Ile Gln Ala Ser His Pro Asp Leu Asn Val Val Gly Gly Ala
             35                  40                  45

Ser Tyr Val Ala Gly Glu Ala Tyr Asn Thr Asp Gly Asn His Gly
         50                  55                  60

Thr His Val Ala Gly Thr Val Ala Ala Leu Asp Asn Thr Thr Gly Val
 65                  70                  75                  80

Leu Gly Val Ala Pro Asn Val Ser Leu Tyr Ala Val Lys Val Leu Asn
                     85                  90                  95

Ser Ser Gly Ser Gly Ser Tyr Ser Gly Ile Val Ser Gly Ile Glu Trp
                100                 105                 110
```

```
Ala Thr Thr Asn Gly Met Asp Val Ile Asn Met Ser Leu Gly Gly Pro
            115                 120                 125

Ser Gly Ser Thr Ala Met Lys Gln Ala Val Asp Asn Ala Tyr Ala Arg
            130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Tyr Ser Ser Val Gly
            180                 185                 190

Ala Glu Leu Glu Val Met Ala Pro Gly Ala Gly Val Tyr Ser Thr Tyr
            195                 200                 205

Pro Thr Ser Thr Tyr Ala Thr Leu Asn Gly Thr Ser Met Ala Ser Pro
            210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Trp Tyr Tyr Gly Lys Gly Leu Ile Asn Val Glu Ala Ala
            260                 265                 270

Ala Gln
```

<210> SEQ ID NO 29
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 12:
      Blapr58Y188Y260WCC

<400> SEQUENCE: 29

```
Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Tyr Val Ala Gly Glu Ala Tyr Asn Thr Asp Gly Asn His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Pro
            115                 120                 125

Ser Gly Ser Thr Ala Met Lys Gln Ala Val Asp Asn Ala Tyr Ala Arg
            130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175
```

```
Gly Ala Val Asp Ser Asn Ser Asn Arg Ala Ser Tyr Ser Ser Val Gly
            180                 185                 190

Ala Glu Leu Glu Val Met Ala Pro Gly Ala Gly Val Tyr Ser Thr Tyr
            195                 200                 205

Pro Thr Ser Thr Tyr Ala Thr Leu Asn Gly Thr Ser Met Ala Ser Pro
            210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Trp Tyr Tyr Gly Lys Gly Leu Ile Asn Val Glu Ala Ala
            260                 265                 270

Ala Gln Cys Cys
        275

<210> SEQ ID NO 30
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 12:
      Blapr58C188Y260W

<400> SEQUENCE: 30

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Cys Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Tyr Ser Ser Val Gly
            180                 185                 190

Ala Glu Leu Glu Val Met Ala Pro Gly Ala Gly Val Tyr Ser Thr Tyr
            195                 200                 205

Pro Thr Ser Thr Tyr Ala Thr Leu Asn Gly Thr Ser Met Ala Ser Pro
            210                 215                 220

His Val Ala Gly Ala Ala Ala Leu Ile Leu Ser Lys His Pro Asn Leu
225                 230                 235                 240
```

Ser Ala Ser Gln Val Arg Asn Arg Leu Ser Ser Thr Ala Thr Tyr Leu
            245                 250                 255

Gly Ser Ser Trp Tyr Tyr Gly Lys Gly Leu Ile Asn Val Glu Ala Ala
        260                 265                 270

Ala Gln

<210> SEQ ID NO 31
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 5:
      estA17Y19Y41C58Y

<400> SEQUENCE: 31

Ala Glu His Asn Pro Val Val Met Val His Gly Ile Gly Gly Ala Ser
1               5                   10                  15

Tyr Asn Tyr Ala Gly Ile Lys Ser Tyr Leu Val Ser Gln Gly Trp Ser
            20                  25                  30

Arg Asp Lys Leu Tyr Ala Val Asp Cys Trp Asp Lys Thr Gly Thr Asn
        35                  40                  45

Tyr Asn Asn Gly Pro Val Leu Ser Arg Tyr Val Gln Lys Val Leu Asp
    50                  55                  60

Glu Thr Gly Ala Lys Lys Val Asp Ile Val Ala His Ser Met Gly Gly
65                  70                  75                  80

Ala Asn Thr Leu Tyr Tyr Ile Lys Asn Leu Asp Gly Gly Asn Lys Val
                85                  90                  95

Ala Asn Val Val Thr Leu Gly Gly Ala Asn Arg Leu Thr Thr Gly Lys
            100                 105                 110

Ala Leu Pro Gly Thr Asp Pro Asn Gln Lys Ile Leu Tyr Thr Ser Ile
        115                 120                 125

Tyr Ser Ser Ala Asp Met Ile Val Met Asn Tyr Leu Ser Arg Leu Asp
    130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr Asn
            180

<210> SEQ ID NO 32
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 5:
      estA17W19Y41C58Y

<400> SEQUENCE: 32

Ala Glu His Asn Pro Val Val Met Val His Gly Ile Gly Gly Ala Ser
1               5                   10                  15

Trp Asn Tyr Ala Gly Ile Lys Ser Tyr Leu Val Ser Gln Gly Trp Ser
            20                  25                  30

Arg Asp Lys Leu Tyr Ala Val Asp Cys Trp Asp Lys Thr Gly Thr Asn
            35                  40                  45

Tyr Asn Asn Gly Pro Val Leu Ser Arg Tyr Val Gln Lys Val Leu Asp
 50                  55                  60

Glu Thr Gly Ala Lys Lys Val Asp Ile Val Ala His Ser Met Gly Gly
 65                  70                  75                  80

Ala Asn Thr Leu Tyr Tyr Ile Lys Asn Leu Asp Gly Gly Asn Lys Val
                 85                  90                  95

Ala Asn Val Val Thr Leu Gly Gly Ala Asn Arg Leu Thr Thr Gly Lys
            100                 105                 110

Ala Leu Pro Gly Thr Asp Pro Asn Gln Lys Ile Leu Tyr Thr Ser Ile
            115                 120                 125

Tyr Ser Ser Ala Asp Met Ile Val Met Asn Tyr Leu Ser Arg Leu Asp
130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr Asn
            180

<210> SEQ ID NO 33
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 6: estB20Y21M40C

<400> SEQUENCE: 33

Glu Ser Val His Asn Pro Val Val Leu Val His Gly Ile Ser Gly Ala
1               5                   10                  15

Ser Tyr Asn Tyr Met Ala Ile Lys Asn Tyr Leu Ile Ser Gln Gly Trp
            20                  25                  30

Gln Ser Asn Lys Leu Tyr Ala Ile Asp Cys Tyr Asp Lys Thr Gly Asn
            35                  40                  45

Asn Leu Asn Asn Gly Pro Gln Leu Ala Ser Tyr Val Asp Arg Val Leu
 50                  55                  60

Lys Glu Thr Gly Ala Lys Lys Val Asp Ile Val Ala His Ser Met Gly
 65                  70                  75                  80

Gly Ala Asn Thr Leu Tyr Tyr Ile Lys Tyr Leu Gly Gly Gly Asn Lys
                 85                  90                  95

Ile Gln Asn Val Val Thr Leu Gly Gly Ala Asn Gly Leu Val Ser Ser
            100                 105                 110

Thr Ala Leu Pro Gly Thr Asp Pro Asn Gln Lys Ile Leu Tyr Thr Ser
            115                 120                 125

Ile Tyr Ser Leu Asn Asp Gln Ile Val Ile Asn Ser Leu Ser Arg Leu
130                 135                 140

Gln Gly Ala Arg Asn Ile Gln Leu Tyr Gly Ile Gly His Ile Gly Leu
145                 150                 155                 160

Leu Ser Asn Ser Gln Val Asn Gly Tyr Ile Lys Glu Gly Leu Asn Gly
                165                 170                 175

Gly Gly Leu Asn Thr Asn
            180

```
<210> SEQ ID NO 34
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 11: ALAB-V4

<400> SEQUENCE: 34

Lys Gln Val Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Val His
            20                  25                  30

Thr Ser Gly Tyr Asp Thr Gln Ala Ile Val Glu Asn Asn Glu Ser Thr
        35                  40                  45

Glu Tyr Gly Leu Val Gln Ile Ser Asn Lys Leu Trp Cys Lys Ser Ser
    50                  55                  60

Gln Val Pro Gln Ser Arg Asn Ile Cys Asp Ile Ser Cys Asp Lys Val
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120

<210> SEQ ID NO 35
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 11: ALAB-M1V3

<400> SEQUENCE: 35

Lys Gln Met Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Val His
            20                  25                  30

Thr Ser Gly Tyr Asp Thr Gln Ala Ile Val Glu Asn Asn Glu Ser Thr
        35                  40                  45

Glu Tyr Gly Leu Val Gln Ile Ser Asn Lys Leu Trp Cys Lys Ser Ser
    50                  55                  60

Gln Val Pro Gln Ser Arg Asn Ile Cys Asp Ile Ser Cys Asp Lys Val
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120

<210> SEQ ID NO 36
<211> LENGTH: 123
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 11: ALAB-Y1V3

<400> SEQUENCE: 36

Lys Gln Met Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Val His
            20                  25                  30

Thr Ser Gly Tyr Asp Thr Gln Ala Ile Val Glu Asn Asn Glu Ser Thr
        35                  40                  45

Glu Tyr Gly Leu Val Gln Ile Ser Asn Lys Leu Trp Cys Lys Ser Ser
    50                  55                  60

Gln Val Pro Gln Ser Arg Asn Ile Cys Asp Ile Ser Cys Asp Lys Val
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120

<210> SEQ ID NO 37
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated protein of SEQ ID NO 11: ALAB-H1V3

<400> SEQUENCE: 37

Lys Gln His Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Val His
            20                  25                  30

Thr Ser Gly Tyr Asp Thr Gln Ala Ile Val Glu Asn Asn Glu Ser Thr
        35                  40                  45

Glu Tyr Gly Leu Val Gln Ile Ser Asn Lys Leu Trp Cys Lys Ser Ser
    50                  55                  60

Gln Val Pro Gln Ser Arg Asn Ile Cys Asp Ile Ser Cys Asp Lys Val
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120

<210> SEQ ID NO 38
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: aprE50Y189Y261L
```

<400> SEQUENCE: 38

```
gtgagaagca aaaaattgtg gatcagcttg ttgtttgcgt taacgttaat ctttacgatg    60
gcgttcagca acatgtctgc gcaggctgcc ggaaaaagca gtacagaaaa gaaatacatt   120
gtcggattta aacagacaat gagtgccatg agttccgcca agaaaaagga tgttatttct   180
gaaaaaggcg gaaaggttca aaagcaattt aagtatgtta acgcggccgc agcaacattg   240
gatgaaaaag ctgtaaaaga attgaaaaaa gatccgagcg ttgcatatgt ggaagaagat   300
catattgcac atgaatatgc gcaatctgtt ccttatggca tttctcaaat taaagcgccg   360
gctcttcact ctcaaggcta cacaggctct aacgtaaaag tagctgttat cgacagcgga   420
attgactctt ctcatcctga cttaaacgtc agaggcggag caagctacgt accttctgaa   480
acaaacccat accaggacgg cagttctcac ggtacgcatg tagccggtac gattgccgct   540
cttaataact caatcggtgt tctgggcgta gcgccaagcg catcattata tgcagtaaaa   600
gtgcttgatt caacaggaag cggccaatat agctggatta ttaacggcat tgagtgggcc   660
atttccaaca atatggatgt tatcaacatg agccttggcg gacctactgg ttctacagcg   720
ctgaaaacag tcgttgacaa agccgttttc agcggtatcg tcgttgctgc cgcagccgga   780
aacgaaggtt catccggaag cacaagcaca gtcggctacc ctgcaaaata tccttctact   840
attgcagtag gtgcggtaaa cagcagcaac caaagagctt catactccag cgcaggttct   900
gagcttgatg tgatggctcc tggcgtgtcc atccaaagca cacttcctgg aggcacttac   960
ggcgcttata acggaacgtc catggcgact cctcacgttg ccggagcagc agcgttaatt  1020
cttctaagc acccgacttg gacaaacgcg caagtccgtg atcgtttaga aagcactgca  1080
acatatcttg gaaactctct ctactatgga aaagggttaa tcaacgtaca agcagctgca  1140
caataa                                                             1146
```

<210> SEQ ID NO 39
<211> LENGTH: 1152
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: aprE50Y189Y261LCC

<400> SEQUENCE: 39

```
gtgagaagca aaaaattgtg gatcagcttg ttgtttgcgt taacgttaat ctttacgatg    60
gcgttcagca acatgtctgc gcaggctgcc ggaaaaagca gtacagaaaa gaaatacatt   120
gtcggattta aacagacaat gagtgccatg agttccgcca agaaaaagga tgttatttct   180
gaaaaaggcg gaaaggttca aaagcaattt aagtatgtta acgcggccgc agcaacattg   240
gatgaaaaag ctgtaaaaga attgaaaaaa gatccgagcg ttgcatatgt ggaagaagat   300
catattgcac atgaatatgc gcaatctgtt ccttatggca tttctcaaat taaagcgccg   360
gctcttcact ctcaaggcta cacaggctct aacgtaaaag tagctgttat cgacagcgga   420
attgactctt ctcatcctga cttaaacgtc agaggcggag caagctacgt accttctgaa   480
acaaacccat accaggacgg cagttctcac ggtacgcatg tagccggtac gattgccgct   540
cttaataact caatcggtgt tctgggcgta gcgccaagcg catcattata tgcagtaaaa   600
gtgcttgatt caacaggaag cggccaatat agctggatta ttaacggcat tgagtgggcc   660
atttccaaca atatggatgt tatcaacatg agccttggcg gacctactgg ttctacagcg   720
```

```
ctgaaaacag tcgttgacaa agccgtttcc agcggtatcg tcgttgctgc cgcagccgga    780
aacgaaggtt catccggaag cacaagcaca gtcggctacc ctgcaaaata tccttctact    840
attgcagtag gtgcggtaaa cagcagcaac caaagagctt catactccag cgcaggttct    900
gagcttgatg tgatggctcc tggcgtgtcc atccaaagca cacttcctgg aggcacttac    960
ggcgcttata acggaacgtc catggcgact cctcacgttg ccggagcagc agcgttaatt   1020
ctttctaagc acccgacttg gacaaacgcg caagtccgtg atcgtttaga aagcactgca   1080
acatatcttg gaaactctct ctactatgga aaagggttaa tcaacgtaca agcagctgca   1140
caatgttgct aa                                                       1152
```

<210> SEQ ID NO 40
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Blapr58Y188Y260W

<400> SEQUENCE: 40

```
atgatgagga aaaagagttt ttggcttggg atgctgacgg ccttaatgct cgtgttcacg     60
atggccttca gcgattccgc gtctgctgct cagccggcga aaaatgttga aaaggattat    120
attgtcggat ttaagtcggg agtgaaaacc gcatccgtca aaaggacat catcaaagag    180 agcggcggaa aagtggacaa gcagtttaga atcatcaacg cggcaaaagc gaagctagac    240
aaagaagcgc ttgaggaagt caaaaatgat ccggatgtcg cttatgtgga agaggatcac    300
gtagctcatg ctttggcgca aaccgttcct acggcattc ctctcattaa agcggacaaa    360
gtgcaggctc aaggctacaa gggagcgaac gtaaaagtcg ccgtcctgga tacaggaatc    420
caagcttctc atccggactt gaacgtagtc ggcggagcaa gctacgtagc tggcgaagct    480
tataacaccg acggcaacgg aacgggcacg catgttgccg gtacagtagc tgcgcttgac    540
aatacaacgg gtgtattagg cgttgcgccg aacgtatcct tgtacgcggt taaagtgctg    600
aattcaagcg gaagcggatc ttacagcggc attgtaagcg gaatcgagtg ggcgacgaca    660
aacggcatgg atgttatcaa catgagcctt ggaggaccat caggctcaac agcgatgaaa    720
caggcggttg acaatgcata tgcaagaggg gttgtcgttg tggcggctgc tgggaacagc    780
ggatcttcag gaaacacgaa tacaatcggc tatcctgcga aatacgactc tgtcatcgca    840
gttggcgcgg tagactctaa cagcaacaga gcttcatatt ccagcgtcgg agcagagctt    900
gaagtcatgg ctcctggcgc aggcgtgtac agcacttacc caaccagcac ttatgcaaca    960
ttgaacggaa cgtcaatggc ttctcctcat gtagcgggag cagcagcttt gatcttgtca   1020
aaacatccga acctttcagc ttcacaagtc cgcaaccgtc tctccagtac ggcgacttat   1080
ttgggaagct cctggtacta tggaaaaggt ctgatcaatg tcgaagctgc cgctcaataa   1140
```

<210> SEQ ID NO 41
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Blapr58Y188Y260WCC

<400> SEQUENCE: 41

```
atgatgagga aaaagagttt ttggcttggg atgctgacgg ccttaatgct cgtgttcacg    60
atggccttca gcgattccgc gtctgctgct cagccggcga aaaatgttga aaaggattat   120
attgtcggat ttaagtcggg agtgaaaacc gcatccgtca aaaggacat catcaaagag    180
agcggcggaa aagtggacaa gcagtttaga atcatcaacg cggcaaaagc gaagctagac   240
aaagaagcgc ttgaggaagt caaaaatgat ccggatgtcg cttatgtgga agaggatcac   300
gtagctcatg ctttggcgca aaccgttcct tacggcattc tctcattaa agcggacaaa    360
gtgcaggctc aaggctacaa gggagcgaac gtaaaagtcg ccgtcctgga tacaggaatc   420
caagcttctc atccggactt gaacgtagtc ggcggagcaa gctacgtagc tggcgaagct   480
tataacaccg acggcaacgg acacggcacg catgttgccg gtacagtagc tgcgcttgac   540
aatacaacgg gtgtattagg cgttgcgccg aacgtatcct tgtacgcggt taaagtgctg   600
aattcaagcg gaagcggatc ttacagcggc attgtaagcg gaatcgagtg ggcgacgaca   660
aacggcatgg atgttatcaa catgagcctt ggaggaccat caggctcaac agcgatgaaa   720
caggcggttg acaatgcata tgcaagaggg gttgtcgttg tggcggctgc tgggaacagc   780
ggatcttcag gaaacacgaa tacaatcggc tatcctgcga aatacgactc tgtcatcgca   840
gttggcgcgg tagactctaa cagcaacaga gcttcatatt ccagcgtcgg agcagagctt   900
gaagtcatgg ctcctggcgc aggcgtgtac agcacttacc caaccagcac ttatgcaaca   960
ttgaacggaa cgtcaatggc ttctcctcat gtagcgggag cagcagcttt gatcttgtca  1020
aaacatccga acctttcagc ttcacaagtc cgcaaccgtc tctccagtac ggcgacttat  1080
ttgggaagct cctggtacta tggaaaaggt ctgatcaatg tcgaagctgc cgctcaatgt  1140
tgctaa                                                              1146
```

<210> SEQ ID NO 42
<211> LENGTH: 1140
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Blapr58C188Y260W

<400> SEQUENCE: 42

```
atgatgagga aaagagtttt ttggcttggg atgctgacgg ccttaatgct cgtgttcacg    60
atggccttca gcgattccgc gtctgctgct cagccggcga aaaatgttga aaaggattat   120
attgtcggat ttaagtcggg agtgaaaacc gcatccgtca aaaggacat catcaaagag    180
agcggcggaa aagtggacaa gcagtttaga atcatcaacg cggcaaaagc gaagctagac   240
aaagaagcgc ttgaggaagt caaaaatgat ccggatgtcg cttatgtgga agaggatcac   300
gtagctcatg ctttggcgca aaccgttcct tacggcattc tctcattaa agcggacaaa    360
gtgcaggctc aaggctacaa gggagcgaac gtaaaagtcg ccgtcctgga tacaggaatc   420
caagcttctc atccggactt gaacgtagtc ggcggagcaa gctgcgtagc tggcgaagct   480
tataacaccg acggcaacgg acacggcacg catgttgccg gtacagtagc tgcgcttgac   540
aatacaacgg gtgtattagg cgttgcgccg aacgtatcct tgtacgcggt taaagtgctg   600
aattcaagcg gaagcggatc ttacagcggc attgtaagcg gaatcgagtg ggcgacgaca   660
aacggcatgg atgttatcaa catgagcctt ggaggaccat caggctcaac agcgatgaaa   720
```

| | |
|---|---|
| caggcggttg acaatgcata tgcaagaggg gttgtcgttg tggcggctgc tgggaacagc | 780 |
| ggatcttcag gaaacacgaa tacaatcggc tatcctgcga aatacgactc tgtcatcgca | 840 |
| gttggcgcgg tagactctaa cagcaacaga gcttcatatt ccagcgtcgg agcagagctt | 900 |
| gaagtcatgg ctcctggcgc aggcgtgtac agcacttacc caaccagcac ttatgcaaca | 960 |
| ttgaacggaa cgtcaatggc ttctcctcat gtagcgggag cagcagcttt gatcttgtca | 1020 |
| aaacatccga acctttcagc ttcacaagtc cgcaaccgtc tctccagtac ggcgacttat | 1080 |
| ttgggaagct cctggtacta tggaaaaggt ctgatcaatg tcgaagctgc cgctcaataa | 1140 |

<210> SEQ ID NO 43
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: estA17Y19Y41C58Y

<400> SEQUENCE: 43

| | |
|---|---|
| gctgaacaca atccagtcgt tatggttcac ggtattggag gggcatcata caattatgcg | 60 |
| ggaattaaga gctatctcgt atctcagggc tggtcgcggg acaagctgta tgcagttgat | 120 |
| tgttgggaca agacaggcac aaattataac aatggaccgg tattatcacg atatgtgcaa | 180 |
| aaggttttag atgaaacggg tgcgaaaaaa gtggatattg tcgctcacag catgggggc | 240 |
| gcgaacacac tttactacat aaaaaatctg gacggcggaa ataaagttgc aaacgtcgtg | 300 |
| acgcttggcg gcgcgaaccg tttgacgaca ggcaaggcgc ttccgggaac agatccaaat | 360 |
| caaaagattt tatacacatc catttacagc agtgccgata tgattgtcat gaattactta | 420 |
| tcaagattag atggtgctag aaacgttcaa atccatggcg ttggacacat cggccttctg | 480 |
| tacagcagcc aagtcaacag cctgattaaa gaagggctga acggcggggg ccagaatacg | 540 |
| aattaa | 546 |

<210> SEQ ID NO 44
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: estA17W19Y41C58Y

<400> SEQUENCE: 44

| | |
|---|---|
| gctgaacaca atccagtcgt tatggttcac ggtattggag gggcatcatg gaattatgcg | 60 |
| ggaattaaga gctatctcgt atctcagggc tggtcgcggg acaagctgta tgcagttgat | 120 |
| tgttgggaca agacaggcac aaattataac aatggaccgg tattatcacg atatgtgcaa | 180 |
| aaggttttag atgaaacggg tgcgaaaaaa gtggatattg tcgctcacag catgggggc | 240 |
| gcgaacacac tttactacat aaaaaatctg gacggcggaa ataaagttgc aaacgtcgtg | 300 |
| acgcttggcg gcgcgaaccg tttgacgaca ggcaaggcgc ttccgggaac agatccaaat | 360 |
| caaaagattt tatacacatc catttacagc agtgccgata tgattgtcat gaattactta | 420 |
| tcaagattag atggtgctag aaacgttcaa atccatggcg ttggacacat cggccttctg | 480 |
| tacagcagcc aagtcaacag cctgattaaa gaagggctga acggcggggg ccagaatacg | 540 |
| aattaa | 546 |

<210> SEQ ID NO 45
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: estB20Y21M40C

<400> SEQUENCE: 45

```
gagtcagtac ataatcctgt cgttcttgtt catggaataa gtggtgcatc atacaactat    60
atggctatta aaaactactt aatttctcaa ggctggcaaa gcaacaaact gtacgcaatt   120
gattgttatg ataaaacagg aaacaaccta ataacggcc cgcagcttgc ttcatatgtt    180
gaccgtgttt taaaagagac tggggcaaaa aaagtagata ttgtggctca tagtatggga   240
ggcgccaata cgctgtacta tattaaatat ttaggcgggg gcaataagat tcaaaatgtc   300
gtaacgcttg gagggctaa tggtttagtg tcatcaaccg cgctgccggg cacagaccct    360
aatcaaaaga tcctctatac atctatttac agtctcaatg atcaaattgt catcaatagc   420
ttgtctcggt tacaaggagc gcgaaacatc cagctttatg gcatcggtca tattggcttg   480
ctttctaata gccaagtgaa cggctatatc aaagaagggc tgaatggcgg aggcctcaat   540
acaaattaa                                                           549
```

<210> SEQ ID NO 46
<211> LENGTH: 372
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: ALAB-V4

<400> SEQUENCE: 46

```
aagcaagtca caaatgtga gctgtcccag ctgctgaaag acatagatgg ttatggaggc    60
atcgctttgc ctgaattgat ctgtaccatg gttcacacca gtggttatga cacacaagcc   120
atagttgaaa acaatgaaag cacggaatat ggactcgtcc agatcagtaa taagctttgg   180
tgcaagagca gccaggtccc tcagtcaagg aacatctgtg acatctcctg tgacaaggtc   240
ctggatgatg acattactga tgacataatg tgtgccaaga agatcctgga tattaaagga   300
attgactact ggttggccca taaagccctc tgcactgaga agctggaaca gtggctttgt   360
gagaagttgt ga                                                      372
```

<210> SEQ ID NO 47
<211> LENGTH: 372
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: ALAB-M1V3

<400> SEQUENCE: 47

```
aagcaaatga caaatgtga gctgtcccag ctgctgaaag acatagatgg ttatggaggc    60
atcgctttgc ctgaattgat ctgtaccatg gttcacacca gtggttatga cacacaagcc   120
atagttgaaa acaatgaaag cacggaatat ggactcgtcc agatcagtaa taagctttgg   180
```

```
tgcaagagca gccaggtccc tcagtcaagg aacatctgtg acatctcctg tgacaaggtc    240
ctggatgatg acattactga tgacataatg tgtgccaaga agatcctgga tattaaagga    300
attgactact ggttggccca taaagccctc tgcactgaga agctggaaca gtggctttgt    360
gagaagttgt ga                                                       372

<210> SEQ ID NO 48
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: ALAB-Y1V3

<400> SEQUENCE: 48
aagcaatata caaaatgtga gctgtcccag ctgctgaaag acatagatgg ttatggaggc    60
atcgctttgc ctgaattgat ctgtaccatg gttcacacca gtggttatga cacacaagcc    120
atagttgaaa acaatgaaag cacggaatat ggactcgtcc agatcagtaa taagctttgg    180
tgcaagagca gccaggtccc tcagtcaagg aacatctgtg acatctcctg tgacaaggtc    240
ctggatgatg acattactga tgacataatg tgtgccaaga agatcctgga tattaaagga    300
attgactact ggttggccca taaagccctc tgcactgaga agctggaaca gtggctttgt    360
gagaagttgt ga                                                       372

<210> SEQ ID NO 49
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: ALAB-H1V3

<400> SEQUENCE: 49
aagcaacata caaaatgtga gctgtcccag ctgctgaaag acatagatgg ttatggaggc    60
atcgctttgc ctgaattgat ctgtaccatg gttcacacca gtggttatga cacacaagcc    120
atagttgaaa acaatgaaag cacggaatat ggactcgtcc agatcagtaa taagctttgg    180
tgcaagagca gccaggtccc tcagtcaagg aacatctgtg acatctcctg tgacaaggtc    240
ctggatgatg acattactga tgacataatg tgtgccaaga agatcctgga tattaaagga    300
attgactact ggttggccca taaagccctc tgcactgaga agctggaaca gtggctttgt    360
gagaagttgt ga                                                       372

<210> SEQ ID NO 50
<211> LENGTH: 263
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P43 promoter from genome of B. subtilis

<400> SEQUENCE: 50
agccattgaa catacggttg atttaataac tgacaaacat caccctcttg ctaaagcggc    60
caaggacgct gccgccgggg ctgtttgcgt ttttgccgtg atttcgtgta tcattggttt    120
```

```
acttattttt ttgccaaagc tgtaatggct gaaaattctt acatttattt tacatttta    180 gaaatgggcg tgaaaaaaag cgcgcgatta tgtaaaatat aaagtgatag cggtaccatt    240
ataggtaaga gaggaatgta cac                                           263
```

<210> SEQ ID NO 51
<211> LENGTH: 434
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PaprE promoter from genome of B. subtilis

<400> SEQUENCE: 51

```
cttatttctt cctccctctc ataattttt tcattctatc ccttttctgt aaagtttatt     60
tttcagaata cttttatcat catgctttga aaaaatatca cgataatatc cattgttctc    120
acggaagcac acgcaggtca tttgaacgaa ttttttcgac aggaatttgc cgggactcag    180
gagcatttaa cctaaaaaag catgacattt cagcataatg aacatttact catgtctatt    240
ttcgttcttt tctgtatgaa aatagttatt tcgagtctct acggaaatag cgagagatga    300
tatacctaaa tagagataaa atcatctcaa aaaaatgggt ctactaaaat attattccat    360
ctattacaat aaattcacag aatagtcttt taagtaagtc tactctgaat tttttaaaa    420 ggagagggta aaga                                                    434
```

<210> SEQ ID NO 52
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PNprE promoter from genome of B. subtilis

<400> SEQUENCE: 52

```
tcctttactt cttattaagg cctcattcgg ttagacagcg gactttcaa aaagtttcaa     60 gatgaaacaa aaatatctca tcttcccctt gatatgtaaa aaacataact cttgaatgaa    120
ccaccacatg acacttgact catcttgata ttattcaaca aaaacaaaca caggacaata    180
ctatcaattt tgtctagtta tgttagtttt tgttgagtat tccagaatgc tagtttaata    240
taacaatata aagttttcag tattttcaaa aaggggggatt tatt                   284
```

<210> SEQ ID NO 53
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PamyE promoter from genome of B. subtilis

<400> SEQUENCE: 53

```
tagagtgatt gtgataattt taaatgtaag cgttaacaaa attctccagt cttcacatcg     60
gtttgaaagg aggaagcgga agaatgaagt aagagggatt tttgactccg aagtaagtct    120
tcaaaaaatc aaataaggag tgtcaaga                                      148
```

<210> SEQ ID NO 54
<211> LENGTH: 359
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PsipS promoter from genome of B. licheniformis

<400> SEQUENCE: 54

```
tgactgtctt tcttttccc gctcagggct gtatggatcg taattgtcat agtactcttc      60
gtagctgctc attttgaggc aatcaccgcc tttgggtcat gatatgataa tgtattataa    120
agagggcgt tttgcctgtg catatataac ggttttcgt gctgtaaata agctgatcaa     180
ctgacaaaat tcaacattga ataaggatt tttcgtttca accgctaata ttatatgtat    240
caaccatttt tttacggctg cgcctgccgg tgcttgcgga aagcattcag acggacggcc   300
tgatatgata gaaggagcgg aatgccgatg aaacgatccg gaagtgaagg agagtactt    359
```

<210> SEQ ID NO 55
<211> LENGTH: 407
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PBlapr promoter from genome of B. licheniformis

<400> SEQUENCE: 55

```
tacgcctttc acatgagctg atttcatatc ttacacccgt ttctgtatgc gatatattgc    60
atattttaat agatgatcga ctaggccgca acctccttcg gcaaaaaatg atctcataaa   120
ataaatgaat agtattttca taaatgaat cagacgaagc aatctcctgt cattcacgga    180
ccccgggacc tctttccctg ccaggttgaa gcggtctatt catactttcg aaccgaatat   240
ttttctaaaa cagttattaa taaccaataa atttaaattg gccgttcaaa aaaatgggtc   300
taccatataa ttcattttt ttctataata aattaacaga ataattagaa tagagtatat    360
tattcttcta tttcaattat tctgaataaa acggaggaga gtgagta                 407
```

<210> SEQ ID NO 56
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PamyS promoter from genome of B. licheniformis

<400> SEQUENCE: 56

```
agtgaagaag cagagaggct attgaataaa tgagtagaaa gcgccatatc ggcgcttttc    60
ttttggaaga aaatataggg aaaatggtat ttgttaaaaa ttctgaatat ttatacaata   120
tcatatgttt cacattgaaa ggggaggaga atc                                153
```

<210> SEQ ID NO 57
<211> LENGTH: 605
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Pcry82 promoter, a synthetic promoter based on
      the pcry32a promoter from the B. thuringiensis

<400> SEQUENCE: 57

```
gtgctttttt tgttgacatt gaagaattat taatgttata attaattaaa gataatatct    60
ttgaattgta acgcccctca aaagtaagaa ctacaaaaaa agaatacgtt atatagaaat   120
atgtttgaac cttcttcaga ttacaaatat attcggacgg actctacctc aaatgcttat   180
ctaactatag aatgacatac aagcacaacc ttgaaaattt gaaatataa ctaccaatga    240 acttgttcat gtgaattatc gctgtattta attttctcaa ttcaatatat aatatgccaa   300
tacattgtta caagtagaaa ttaagacacc cttgatagcc ttactatacc taacatgatg   360
tagtattaaa tgaatatgta aatatattta tgataagaag cgacttattt ataatcatta   420
catatttttc tattggaatg attaagattc caatagaata gtgtataaat tatttatctt   480
gaaaggaggg atgcctaaaa acgaagaaca ttaaaaacat atatttgcac cgtctaatgg   540
atttatgaaa aatcatttta tcagtttgaa aattatgtat tatgataaga aagggaggaa   600
gaaaa                                                               605
```

<210> SEQ ID NO 58
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PAPase promoter from genome of B. licheniformis

<400> SEQUENCE: 58

```
gtaccttctg aggatttggc tctagaggac tggaaccgcg tcatatcaac caatttgacg    60
gggatgtttc taggatgccg ggaagcgatc ggctatatgc tcgaccataa tattaaaggc   120
tcggtcatca atatgtccag cgtccatcag caaatcccgt ggccgcattt tgtccattat   180
gcggcaagca agggcggggc aaaactgctg acggaaaccc ttgcccttga atatgccccg   240
aaaggaatcc gggtaaacgc gatcggcccc ggtgcaatcg atacgccgat taacgccgaa   300
aaattcgctg atcccgaatt gaaaaaaggc gttattgaat tgattcctat agggtatatc   360
ggaaagccgg aggaagtcgc agcctgcgcg gcctggctag catccgaaga agcaagctat   420
gtgacgggcc tgacgctgta tgtagacggc gggatgacaa atacccggg attccaagcg    480 ggaaaagggt gaaagaagg cggatgcctt ctttttcatca taagcccatg aaaatttaca   540
taagattaat agaaagcaaa agtgctgttt acatagcaat gatagtgtag gtgtgtcaac   600
aaaatgcagt tatggaggga gtacataaga                                    630
```

<210> SEQ ID NO 59
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta Pro1 gene fragments

<400> SEQUENCE: 59

```
aatatcaaaa ttgccgtcat tgacagcggg atctccccc acgatgacct gtcgattgcc    60
ggcgggtatt cagctgtcag ttatacctct tcttacaaag atgataacgg ccacggaaca   120
```

```
catgtcgcag ggattatcgg agccaagcat aacggctacg gaattgacgg catcgcaccg    180
gaagcacaaa tatacgcggt taaagcgctt gatcagaacg gctcggggga tcttcaaagt    240
cttctccaag gaattgactg gtcgatcgca acaggatgg acatcgtcaa tatgagcctt     300
ggcacgacgt cagacagcaa aatccttcat gacgccgtga acaaagcata tgaacaaggt    360
gttctgcttg ttgccgcaag cggtaacgac ggaaacggca agccagtgaa ttatccggcg    420
gcatacagca gtgtcgttgc ggtttcagca acaaacgaaa agaatcagct tgcctccttt    480
tcaacaactg gagatgaagt tgaattttca gcaccgggga caaacatcac aagcacttac    540
ttaaaccagt attatgcaac gggaagcgga acatcccaag cgacaccgca cgccgctgcc    600
atgtttgcct tgttaaaaca gcgtgatcct gccgagacaa acgtccagct tcgcgaggaa    660
atgcggaaaa actaa                                                    675
```

<210> SEQ ID NO 60
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta Pro2 gene fragments

<400> SEQUENCE: 60

```
ggaaaaggca tcaaggtggc gattattgac actggggttg aatacaatca cccagatctg    60
aagaaaaact ttggacaata taaggatac gattttgtgg acaatgatta cgatccaaaa     120
gaaacaccaa ccggcgatcc gagggcgag gcaactgacc atggcacaca cgtagccgga    180
actgtggctg caaacggaac gattaaaggc gtagcgcctg atgccacact tcttgcttat    240
cgtgtgttag ggcctggcgg aagcggcaca acggaaaacg tcatcgcggg cgtggaacgt    300
gcagtgcagg acggggcaga tgtgatgaac ctgtctctcg gaaactcttt aaacaacccg    360
gactgggcga caagcacagc gcttgactgg gccatgtcag aaggcgttgt cgctgttacc    420
tcaaacggca acagcggacc gaacggctgg acagtcggat cgccgggcac atcaagagaa    480
gcgatttctg tcggtgcgac tcagctgccg ctcaatgaat acgccgtcac tttcggctcc    540
tactcttcat aa                                                       552
```

<210> SEQ ID NO 61
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta amyQ gene fragments

<400> SEQUENCE: 61

```
tggtcgttca atacgttaaa acacaatatg aaggatattc atgatgcagg atatacagcc    60
attcagacat ctccgattaa ccaagtaaag gaagggaatc aaggagataa agcatgtcg    120 aactggtact ggctgtatca gccgacatcg tatcaaattg caaccgtta cttaggtact    180 gaacaagaat ttaaagaaat gtgtgcagcc gctgaagaat atggcataaa ggtcattgtt    240
gacgcggtca tcaatcatac caccagtgat tatgccgcga tttccaatga ggttaagagt    300
attccaaact ggacacatgg aaacacacaa attaaaaact ggtctgatcg atgggatgtc    360
acgcagaatt cattgctcgg gctgtatgac tggaatacac aaaatacaca agtacagtcc    420
```

```
tatctgaaac ggttcttaga cagggcattg aatgacgggg cagacggttt tcgatttgat      480
gccgccaaac atatagagct tccagatgat ggcagttacg gcagtcaatt ttggccgaat      540
atctaa                                                                 546
```

<210> SEQ ID NO 62
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta yjeA gene

<400> SEQUENCE: 62

```
ctttgccatc aaggaggatt atatcgaact ttactttgac acatatcagg ttgcagcagg       60
ctatcttgga gagcaatcga ttgccattaa gaaaagtctt ttgaaagaca ttctgaaaga      120
acaatatatt gataaagcaa aaaataaaaa taaaatcaaa gaacaaaagc cgaagcatga      180
agtgatttct ttacccaaag aggaaacagt tgatccaaat caaaaagtca ttgcgcttac      240
tttcgacgac ggcccgaatc ctgcgacaac aaatcagatt ctagactcct tgaagaaata      300
taagggtcat gccacgtttt ttgttttggg gagcagagtt caatattatc cggaaacgct      360
aataagaatg ctgaaagaag gaaatgaggt tgggaaccat tcatggagcc atccgcttct      420
cacaaggctt tcagtgaaag aagcgttaaa gcagatcaat gatacgcaag acatcattga      480
aaaaataagc ggatatcgtc cgacgcttgt aagaccccca tacggcggca ttaatgatga      540
actgcggagt caaatgaaaa tggataa                                          567
```

<210> SEQ ID NO 63
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: estA gene fragments without native signal
      peptide

<400> SEQUENCE: 63

```
gctgaacaca atccagtcgt tatggttcac ggtattggag gggcatcatt caattttgcg       60
ggaattaaga gctatctcgt atctcagggc tggtcgcggg acaagctgta tgcagttgat      120
ttttgggaca agacaggcac aaattataac aatggaccgg tattatcacg atttgtgcaa      180
aaggttttag atgaaacggg tgcgaaaaaa gtggatattg tcgctcacag catgggggc       240 gcgaacacac tttactacat aaaaaaatctg acggcggaa ataaagttgc aaacgtcgtg      300
acgcttggcg gcgcgaaccg tttgacgaca ggcaaggcgc ttccgggaac agatccaaat      360
caaaagattt tatacacatc catttacagc agtgccgata tgattgtcat gaattactta      420
tcaagattag atggtgctag aaacgttcaa atccatggcg ttggacacat cggccttctg      480
tacagcagcc aagtcaacag cctgattaaa gaagggctga acggcggggg ccagaatacg      540
aattaa                                                                 546
```

<210> SEQ ID NO 64
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: estB gene fragments without native signal
      peptide

<400> SEQUENCE: 64

| | | | | | |
|---|---|---|---|---|---|
| gagtcagtac | ataatcctgt | cgttcttgtt | catggaataa | gtggtgcatc | atacaacttt | 60 |
| ttcgctatta | aaaactactt | aatttctcaa | ggctggcaaa | gcaacaaact | gtacgcaatt | 120 |
| gatttttatg | ataaaacagg | aaacaaccta | ataacggcc | cgcagcttgc | ttcatatgtt | 180 |
| gaccgtgttt | taaagagac | tggggcaaaa | aaagtagata | ttgtggctca | tagtatggga | 240 |
| ggcgccaata | cgctgtacta | tattaaatat | ttaggcgggg | gcaataagat | tcaaaatgtc | 300 |
| gtaacgcttg | gagggctaa | tggtttagtg | tcatcaaccg | cgctgccggg | cacagaccct | 360 |
| aatcaaaaga | tcctctatac | atctatttac | agtctcaatg | atcaaattgt | catcaatagc | 420 |
| ttgtctcggt | tacaaggagc | gcgaaacatc | cagctttatg | gcatcggtca | tattggcttg | 480 |
| ctttctaata | gccaagtgaa | cggctatatc | aaagaagggc | tgaatggcgg | aggcctcaat | 540 |
| acaaattaa | | | | | | 549 |

<210> SEQ ID NO 65
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: aprE gene

<400> SEQUENCE: 65

| | | | | | |
|---|---|---|---|---|---|
| gtgagaagca | aaaaattgtg | gatcagcttg | ttgtttgcgt | taacgttaat | ctttacgatg | 60 |
| gcgttcagca | acatgtctgc | gcaggctgcc | ggaaaaagca | gtacgaaaaa | gaaatacatt | 120 |
| gtcggattta | aacagacaat | gagtgccatg | agttccgcca | agaaaaagga | tgttatttct | 180 |
| gaaaaaggcg | gaaaggttca | aaagcaattt | aagtatgtta | acgcggccgc | agcaacattg | 240 |
| gatgaaaaag | ctgtaaaaga | attgaaaaaa | gatccgagcg | ttgcatatgt | ggaagaagat | 300 |
| catattgcac | atgaatatgc | gcaatctgtt | ccttatggca | tttctcaaat | taaagcgccg | 360 |
| gctcttcact | ctcaaggcta | cacaggctct | aacgtaaaag | tagctgttat | cgacagcgga | 420 |
| attgactctt | ctcatcctga | cttaaacgtc | agaggcggag | caagcttcgt | accttctgaa | 480 |
| acaaacccat | accaggacgg | cagttctcac | ggtacgcatg | tagccggtac | gattgccgct | 540 |
| cttaataact | caatcggtgt | tctgggcgta | gcgccaagcg | catcattata | tgcagtaaaa | 600 |
| gtgcttgatt | caacaggaag | cggccaatat | agctggatta | ttaacggcat | tgagtgggcc | 660 |
| atttccaaca | atatggatgt | tatcaacatg | agccttggcg | gacctactgg | ttctacagcg | 720 |
| ctgaaaacag | tcgttgacaa | agccgtttcc | agcggtatcg | tcgttgctgc | cgcagccgga | 780 |
| aacgaaggtt | catccggaag | cacaagcaca | gtcggctacc | ctgcaaaata | tccttctact | 840 |
| attgcagtag | gtgcggtaaa | cagcagcaac | caaagagctt | cattctccag | cgcaggttct | 900 |
| gagcttgatg | tgatggctcc | tggcgtgtcc | atccaaagca | cacttcctgg | aggcacttac | 960 |
| ggcgcttata | acggaacgtc | catggcgact | cctcacgttg | ccggagcagc | agcgttaatt | 1020 |
| cttttctaagc | acccgacttg | gacaaacgcg | caagtccgtg | atcgtttaga | aagcactgca | 1080 |
| acatatcttg | gaaactcttt | ctactatgga | aaagggttaa | tcaacgtaca | agcagctgca | 1140 | caataa 1146

<210> SEQ ID NO 66
<211> LENGTH: 1980
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: amyE gene

<400> SEQUENCE: 66

| | | | | | |
|---|---|---|---|---|---|
| atgtttgcaa | aacgattcaa | aacctcttta | ctgccgttat | tcgctggatt | tttattgctg | 60 |
| tttcatttgg | ttctggcagg | accggcggct | gcgagtgctg | aaacggcgaa | caaatcgaat | 120 |
| gagcttacag | caccgtcgat | caaaagcgga | accattcttc | atgcatggaa | ttggtcgttc | 180 |
| aatacgttaa | aacacaatat | gaaggatatt | catgatgcag | gatatacagc | cattcagaca | 240 |
| tctccgatta | accaagtaaa | ggaagggaat | caaggagata | aaagcatgtc | gaactggtac | 300 |
| tggctgtatc | agccgacatc | gtatcaaatt | ggcaaccgtt | acttaggtac | tgaacaagaa | 360 |
| tttaaagaaa | tgtgtgcagc | cgctgaagaa | tatggcataa | aggtcattgt | tgacgcggtc | 420 |
| atcaatcata | ccaccagtga | ttatgccgcg | atttccaatg | aggttaagag | tattccaaac | 480 |
| tggacacatg | gaaacacaca | aattaaaaac | tggtctgatc | gatgggatgt | cacgcagaat | 540 |
| tcattgctcg | gctgtatga | ctggaataca | caaatacac | aagtacagtc | ctatctgaaa | 600 |
| cggttcttag | acagggcatt | gaatgacggg | gcagacggtt | tcgatttga | tgccgccaaa | 660 |
| catatagagc | ttccagatga | tggcagttac | ggcagtcaat | tttggccgaa | tatcacaaat | 720 |
| acatctgcag | agttccaata | cggagaaatc | ctgcaggata | gtgcctccag | agatgctgca | 780 |
| tatgcgaatt | atatggatgt | gacagcgtct | aactatgggc | attccataag | gtccgcttta | 840 |
| aagaatcgta | atctgggcgt | gtcgaatatc | tcccactatg | catctgatgt | gtctgcggac | 900 |
| aagctagtga | catgggtaga | gtcgcatgat | acgtatgcca | atgatgatga | agagtcgaca | 960 |
| tggatgagcg | atgatgatat | ccgtttaggc | tgggcggtga | tagcttctcg | ttcaggcagt | 1020 |
| acgcctcttt | tcttttccag | acctgaggga | ggcggaaatg | gtgtgaggtt | cccggggaaa | 1080 |
| agccaaatag | cgatcgcgg | gagtgcttta | tttgaagatc | aggctatcac | tgcggtcaat | 1140 |
| agatttcaca | atgtgatggc | tggacagcct | gaggaactct | cgaacccgaa | tggaaacaac | 1200 |
| cagatattta | tgaatcagcg | cggctcacat | ggcgttgtgc | tggcaaatgc | aggttcatcc | 1260 |
| tctgtctcta | tcaatacggc | aacaaaattg | cctgatggca | ggtatgacaa | taaagctgga | 1320 |
| gcgggttcat | ttcaagtgaa | cgatggtaaa | ctgacaggca | cgatcaatgc | caggtctgta | 1380 |
| gctgtgcttt | atcctgatga | tattgcaaaa | gcgcctcatg | ttttccttga | aattacaaaa | 1440 |
| acaggtgtaa | cacattcttt | caatgatcaa | ctgacgatta | ccttgcgtgc | agatgcgaat | 1500 |
| acaacaaaag | ccgtttatca | atcaataat | ggaccagaga | cggcgtttaa | ggatggagat | 1560 |
| caattcacaa | tcggaaaagg | agatccattt | ggcaaaacat | acaccatcat | gttaaaagga | 1620 |
| acgaacagtg | atggtgtaac | gaggaccgag | aaatacagtt | ttgttaaaag | agatccagcg | 1680 |
| tcggccaaaa | ccatcggcta | tcaaaatccg | aatcattgga | gccaggtaaa | tgcttatatc | 1740 |
| tataaacatg | atgggagccg | agtaattgaa | ttgaccggat | cttggcctgg | aaaaccaatg | 1800 |
| actaaaaatg | cagacggaat | ttacacgctg | acgctgcctg | cggacacgga | tacaaccaac | 1860 |
| gcaaaagtga | ttttaataa | tggcagcgcc | caagtgcccg | gtcagaatca | gcctggcttt | 1920 |

```
gattacgtgc taaatggttt atataatgac tcgggcttaa gcggttctct tccccattga    1980
```

<210> SEQ ID NO 67
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: amyL gene

<400> SEQUENCE: 67

```
atgaaacaac aaaaacggct ttacgcccga ttgctgccgc tgttatttgc gctcatcttc      60
ttgctgcctc attctgcagc agcggcggca aatcttaaag gacgctgat gcagtatttt     120 gaatggtaca tgcccaatga cggccaacat tggaagcgct tgcaaaacga ctcggcatat    180
ttggctgaac acggtattac tgccgtctgg attcccccgg catataaggg aacgagccaa    240
gcggatgtgg gctacggtgc ttacgacctt tatgatttag gggagtttca tcaaaaaggg    300
acggttcgga caaagtacgg cacaaaagga gagctgcaat ctgcgatcaa aagtcttcat    360
tcccgcgaca ttaacgttta cggggatgtg gtcatcaacc acaaaggcgg cgctgatgcg    420
accgaagatg taaccgcggt tgaagtcgat cccgctgacc gcaaccgcgt aatttcagga    480
gaacaccgaa ttaaagcctg gacacatttt catttccgg ggcgcggcag cacatacagc     540
gattttaaat ggcattggta ccatttgac ggaaccgatt gggacgagtc ccgaaagctg     600
aaccgcatct ataagtttca aggaaaggct tgggattggg aagtttccaa tgaaaacggc    660
aactatgatt atttgatgta tgccgacatc gattatgacc atcctgatgt cgcagcagaa    720
attaagagat ggggcacttg gtatgccaat gaactgcaat tggacggttt ccgtcttgat    780
gctgtcaaac acattaaatt ttcttttttg cgggattggg ttaatcatgt cagggaaaaa    840
acggggaagg aaatgtttac ggtagctgaa tattggcaga tgactttggg cgcgctggaa    900
aactatttga acaaaacaaa ttttaatcat tcagtgtttg acgtgccgct tcattatcag    960
ttccatgctg catcgacaca gggaggcggc tatgatatga ggaaattgct gaacggtacg   1020 gtcgttttcca agcatccgtt gaaagcggtt acatttgtcg ataaccatga tacacagccg   1080
gggcaatcgc ttgagtcgac tgtccaaaca tggtttaagc cgcttgctta cgcttttatt   1140
ctcacaaggg aatctggata ccctcaggtt ttctacgggg atatgtacgg gacgaaagga   1200
gactcccagc gcgaaattcc tgccttgaaa cacaaaattg aaccgatctt aaaagcgaga   1260
aaacagtatg cgtacggagc acagcatgat tatttcgacc accatgacat tgtcggctgg   1320
acaagggaag cgacagctc ggttgcaaat tcaggtttgg cggcattaat aacagacgga   1380
cccggtgggg caaagcgaat gtatgtcggc cggcaaaacg ccggtgagac atggcatgac   1440
attaccggaa accgttcgga gccggttgtc atcaattcgg aaggctgggg agagtttcac   1500
gtaaacggcg ggtcggtttc aatttatgtt caaagatag                            1539
```

<210> SEQ ID NO 68
<211> LENGTH: 1566
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: NprE gene

<400> SEQUENCE: 68

```
gtgggtttag gtaagaaatt gtctgttgct gtcgctgctt cgtttatgag tttatcaatc      60
agcctgccag gtgttcaggc tgctgaaggt catcagctta agagaatca aacaaatttc     120
ctctccaaaa acgcgattgc gcaatcagaa ctctctgcac caaatgacaa ggctgtcaag    180
cagttttga aaagaacag caacattttt aaaggtgacc cttccaaaag gctgaagctt      240
gttgaaagca cgactgatgc ccttggatac aagcactttc gatatgcgcc tgtcgttaac    300
ggagtgccaa ttaaagattc gcaagtgatc gttcacgtcg ataaatccga taatgtctat    360
gcggtcaatg gtgaattaca caatcaatct gctgcaaaaa cagataacag ccaaaaagtc    420
tcttctgaaa aagcgctggc actcgctttc aaagctatcg gcaaatcacc agacgctgtt   480
tctaacggag cggccaaaaa cagcaataaa gccgaattaa aagcgataga acaaaaagac    540
ggcagctatc gtcttgctta cgacgtgacg attcgctatg tcgagcctga acctgcaaac    600
tgggaagtct tagttgacgc cgaaacaggc agcattttaa aacagcaaaa taaagtagaa    660
catgccgccg ccactggaag cggaacaacg ctaaagggcg caactgttcc tttgaacatc    720
tcttatgaag gcggaaaata tgttctaaga gatctttcaa aaccaacagg caccccaaatc   780
atcacatatg atttgcaaaa cagacaaagc cgccttccgg gcacgcttgt ctcaagcaca    840
acgaaaacat ttacatcttc atcacagcgg gcagccgttg acgcacacta taacctcggt   900
aaagtgtacg attattttta ttcaaacttt aaacgaaaca gctatgataa caaaggcagt    960
aaaatcgttt cttccgttca ctacggcact caatacaata acgctgcatg gacaggagac   1020
cagatgattt acgtgatgg cgacggttca ttcttctctc cgctttccgg ctcattagat    1080
gtgacagcgc atgaaatgac acatggcgtc acccaagaaa cagccaactt gatttatgaa   1140
aatcagccag gtgcattaaa cgagtctttc tctgacgtat tcgggtattt taacgataca   1200
gaagactggg acatcggtga agacattacg gtcagccagc ctgctcttcg cagcctgtcc   1260
aaccctacaa aatacaacca gcctgacaat tacgccaatt accgaaacct tccaaacaca   1320
gatgaaggcg attatggcgg tgtacacaca aacagcggaa ttccaaacaa agccgcttac   1380
aacaccatca caaaacttgg tgtatctaaa tcacagcaaa tctattaccg tgcgttaaca   1440
acgtacctca cgccttcttc cacgttcaaa gatgccaagg cagctctcat tcagtctgcc   1500
cgtgacctct acggctcaac tgatgccgct aaagttgaag cagcctggaa tgctgttgga   1560
ttgtaa                                                                1566
```

<210> SEQ ID NO 69
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: ALAB gene without native signal peptide

<400> SEQUENCE: 69

```
aagcaattca caaaatgtga gctgtcccag ctgctgaaag acatagatgg ttatggaggc      60
atcgctttgc ctgaattgat ctgtaccatg tttcacacca gtggttatga cacacaagcc    120
atagttgaaa acaatgaaag cacggaatat ggactcttcc agatcagtaa taagctttgg    180
tgcaagagca gccaggtccc tcagtcaagg aacatctgtg acatctcctg tgacaagttc    240
ctggatgatg acattactga tgacataatg tgtgccaaga gatcctgga tattaaagga     300
```

```
attgactact ggttggccca taaagccctc tgcactgaga agctggaaca gtggctttgt    360
gagaagttgt ga                                                       372
```

<210> SEQ ID NO 70
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Blapr gene

<400> SEQUENCE: 70

```
atgatgagga aaaagagttt ttggcttggg atgctgacgg ccttaatgct cgtgttcacg     60
atggccttca gcgattccgc gtctgctgct cagccggcga aaatgttga aaaggattat    120 attgtcggat ttaagtcggg agtgaaaacc gcatccgtca aaaggacat catcaaagag    180 agcggcggaa aagtggacaa gcagtttaga atcatcaacg cggcaaaagc gaagctagac    240
aaagaagcgc ttgaggaagt caaaaatgat ccggatgtcg cttatgtgga gaggatcac    300 gtagctcatg cttggcgca aaccgttcct acggcattc ctctcattaa gcggacaaaa     360
gtgcaggctc aaggctacaa gggagcgaac gtaaaagtcg ccgtcctgga tacaggaatc    420
caagcttctc atccggactt gaacgtagtc ggcggagcaa gcttcgtagc tggcgaagct    480
tataacaccg acggcaacgg acacggcacg catgttgccg gtacagtagc tgcgcttgac    540
aatacaacgg gtgtattagg cgttgcgccg aacgtatcct tgtacgcggt taaagtgctg    600
aattcaagcg gaagcggatc ttacagcggc attgtaagcg gaatcgagtg ggcgacgaca    660
aacggcatgg atgttatcaa catgagcctt ggaggaccat caggctcaac agcgatgaaa    720
caggcggttg acaatgcata tgcaagaggg gttgtcgttg tggcggctgc tgggaacagc    780
ggatcttcag gaaacacgaa tacaatcggc tatcctgcga aatacgactc tgtcatcgca    840
gttggcgcgg tagactctaa cagcaacaga gcttcattttt ccagcgtcgg agcagagctt    900
gaagtcatgg ctcctggcgc aggcgtgtac agcacttacc caaccagcac ttatgcaaca    960
ttgaacggaa cgtcaatggc ttctcctcat gtagcgggag cagcagcttt gatcttgtca   1020
aaacatccga acctttcagc ttcacaagtc cgcaaccgtc tctccagtac ggcgacttat   1080
ttgggaagct ccttctacta tggaaaaggt ctgatcaatg tcgaagctgc cgctcaataa   1140
```

<210> SEQ ID NO 71
<211> LENGTH: 615
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Lip gene

<400> SEQUENCE: 71

```
atgcgtcgtc attcattttt atctattcta ttgatttgca tgctgtctgt tgtgtccgta     60 tttttcgttcc ggccttcagc agcttccgcc gcttcccaca atccggtcgt catggtccac    120
ggcatcggcg gagccgatta aacttcatc ggcattaaat cgtatttaca atctcaaggc     180
tggacaagca gtgagcttta cgccatcaac tttatcgata aaacgggaaa taatataaac    240
aatgctccga gattatccga atacatcaag cgtgtgctga tcaaacagg agcatcaaaa    300 gtcgatattg tcgcccacag catgggcggg gccaatacgc tctattatat taaaaatctg    360
```

```
gatggtgcgg ataaagtcgg acatgtcgtc acccttgggg gcgctaatcg tctcgttaca    420
aacacggcgc ctcagaatga caaaatctca tacacttcga tttacagcac aagcgactat    480
atcgtcttaa acagcctctc caaacttgat ggtgcaaaca atgtgcaaat ctcaggcgta    540
agccatgtcg gtcttttgtt cagcagcaaa gtaaatgcct tgattaaaga cgggctgacc    600
gccagcggga aataa                                                      615
```

<210> SEQ ID NO 72
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: EGFP gene

<400> SEQUENCE: 72

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcagcta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actcacggca tggacgagct gtacaagtaa    720
```

<210> SEQ ID NO 73
<211> LENGTH: 1140
<212> TYPE: DNA
<213> ORGANISM: Bacillus licheniformis
<220> FEATURE:
<223> OTHER INFORMATION: 10266apr gene

<400> SEQUENCE: 73

```
atgatgagga aaagagtttt ttggcttggg atgctgacgg ccttcatgct cgtgttcacg     60
atggcattca gcgattccgc ttctgctgct caaccggcga aaaatgttga aaaggattat    120
attgtcggat ttaagtcagg agtgaaaacc gcatctgtca aaaaggacat catcaaagag    180
agcggcggaa aagtggacaa gcagtttaga atcatcaacg cggcaaaagc gaagctagac    240
aaagaagcgc ttaaggaagt caaaaatgat ccggatgtcg cttatgtgga agaggatcat    300
gtggcccatg ccttggcgca aaccgttcct tacggcattc ctctcattaa agcggacaaa    360
gtgcaggctc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggatc atacagcggc attgtaagcg gaatcgagtg ggcgacaaca    660
```

```
aacggcatgg atgttatcaa tatgagcctt gggggagcat caggctcgac agcgatgaaa      720
caggcagtcg acaatgcata tgcaagaggg gttgtcgttg tagctgcagc agggaacagc      780
ggatcttcag gaaacacgaa tacaattggc tatcctgcga aatacgattc tgtcatcgct      840
gttggtgcgg tagactctaa cagcaacaga gcttcatttt ccagcgtcgg agcagagctt      900
gaagtcatgg ctcctggcgc aggcgtatac agcacttacc caacgaacac ttatgcaaca      960
ttgaacggaa cgtcaatggc ttctcctcat gtagcgggag cagcagcttt gatcttgtca     1020
aaacatccga acctttcagc ttcacaagtc cgcaaccgtc tctccagcac ggcgacttat     1080
ttgggaagct ccttctacta tgggaaaggt ctgatcaatg tcgaagctgc cgctcaataa     1140
```

<210> SEQ ID NO 74
<211> LENGTH: 274
<212> TYPE: PRT
<213> ORGANISM: Bacillus licheniformis
<220> FEATURE:
<223> OTHER INFORMATION: 10266apr

<400> SEQUENCE: 74

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```

<210> SEQ ID NO 75
<211> LENGTH: 1140
<212> TYPE: DNA
<213> ORGANISM: Bacillus licheniformis
<220> FEATURE:
<223> OTHER INFORMATION: 10266apr-W4

<400> SEQUENCE: 75

```
atgatgagga aaaagagttt ttggcttggg atgctgacgg ccttcatgct cgtgttcacg      60
atggcattca gcgattccgc ttctgctgct caaccggcga aaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctggaa gggagcgaat gtaaaagtag ccgtcctgga tacaggaatc     420
caagcttctc atccggactt gaacgtagtc ggcggagcaa gctatgtggc tggcgaagct     480
tataacaccg acggcaacgg acacggcaca catgttgccg gtacagtagc tgcgcttgac     540
aatacaacgg gtgtattagg cgttgcgcca agcgtatcct tgtacgcggt aaagtactg      600
aattcaagcg gaagcggatc atacagcggc attgtaagcg gaatcgagtg ggcgacaaca     660
aacggcatgg atgttatcaa tatgagcctt gggggagcat caggctcgac agcgatgaaa     720
caggcagtcg acaatgcata tgcaagaggg gttgtcgttg tagctgcagc agggaacagc     780
ggatcttcag gaaacacgaa tacaattggc tatcctgcga aatacgattc tgtcatcgct     840
gttggtgcgg tagactctaa cagcaacaga gcttcatggt ccagcgtcgg agcagagctt     900
gaagtcatgg ctcctggcgc aggcgtatac agcacttacc caacgaacac ttatgcaaca     960
ttgaacggaa cgtcaatggc ttctcctcat gtagcgggag cagcagcttt gatcttgtca    1020
aaacatccga accttttcagc ttcacaagtc cgcaaccgtc tctccagcac ggcgacttat    1080
ttgggaagct cctggtacta tgggaaaggt ctgatcaatg tcgaagctgc cgctcaataa    1140
```

<210> SEQ ID NO 76
<211> LENGTH: 274
<212> TYPE: PRT
<213> ORGANISM: Bacillus licheniformis
<220> FEATURE:
<223> OTHER INFORMATION: 10266apr-W4

<400> SEQUENCE: 76

```
Ala Gln Thr Val Pro Tyr Gly Ile Pro Leu Ile Lys Ala Asp Lys Val
 1               5                  10                  15

Gln Ala Gln Gly Trp Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Tyr Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110
```

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Trp Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Trp Tyr Tyr Gly Lys Gly Leu Ile Asn Val Glu Ala Ala
            260                 265                 270

Ala Gln

<210> SEQ ID NO 77
<211> LENGTH: 1146
<212> TYPE: DNA
<213> ORGANISM: Bacillus subtilis
<220> FEATURE:
<223> OTHER INFORMATION: 10073aprE gene

<400> SEQUENCE: 77

```
gtgagaagca aaaaattgtg atcagcttg  ttgtttgcgt taacgttaat ctttacgatg     60
gcgttcagca acatgtctgc gcaggctgcc ggaaaaagca gtacagaaaa gaaatacatt    120
gtcggattta acagacaat  gagtgccatg agttccgcca agaaaaagga tgttatttct    180
gaaaaaggcg gaaaggttca aaagcaattt aagtatgtta acgcggccgc agcaacattg    240
gatgaaaaag ctgtaaaaga attgaaaaaa gatccgagcg ttgcatatgt ggaagaagat    300
catattgcac atgaatatgc gcaatctgtt ccttatggca tttctcaaat taaagcgccg    360
gctcttcact ctcaaggcta cacaggctct aacgtaaaag tagctgttat cgacagcgga    420
attgactctt ctcatcctga cttaaacgtc agaggcggag caagcttcgt accttctgaa    480
acaaacccat accaggacgg cagttctcac ggtacgcatg tagccggtac gattgccgct    540
cttaataact caatcggtgt tctgggcgta gcgccaagcg catcattata tgcagtaaaa    600
gtgcttgatt caacaggaag cggccaatat agctggatta ttaacggcat tgaatgggcc    660
atttccaaca atatggatgt tattaacatg agccttggcg gaccttctgg ttctacagcg    720
ctgaaaacag tcgttgataa agccgttttcc agcggtatcg tcgttgctgc cgctgccgga    780
aacgaaggtt cgtccggaag ctcaagcaca gtcggctacc ctgcaaaata tccttctact    840
attgcggtag gtgcggtaaa cagcagcaac caaagagctt cattctcaag cgcaggttct    900
gagcttgatg tgatggctcc tggcgtatcc atccaaagca cacttcctgg aggcacttac    960
ggtgcttaca acggcacgtc catggcgact cctcacgttg ccggagcagc agcgctaatt   1020
ctttctaagc acccgacttg gacaaacgcg caagtccgtg atcgtttaga aagcactgca   1080
```
acatatcttg gaaactcttt ctactatgga aaagggttaa tcaacgtaca agcagctgca    1140
caataa    1146

<210> SEQ ID NO 78
<211> LENGTH: 275
<212> TYPE: PRT
<213> ORGANISM: Bacillus subtilis
<220> FEATURE:
<223> OTHER INFORMATION: 10073aprE gene

<400> SEQUENCE: 78

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Ser Gly Ser Thr Ala Leu Lys Thr Val Val Asp Lys Ala Val Ser
    130                 135                 140

Ser Gly Ile Val Val Ala Ala Ala Gly Asn Glu Gly Ser Ser Gly
145                 150                 155                 160

Ser Ser Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275

<210> SEQ ID NO 79
<211> LENGTH: 1146
<212> TYPE: DNA
<213> ORGANISM: Bacillus subtilis
<220> FEATURE:
<223> OTHER INFORMATION: 10076aprE-W7 gene

<400> SEQUENCE: 79
gtgagaagca aaaaattgtg gatcagcttg ttgtttgcgt taacgttaat ctttacgatg    60

-continued

```
gcgttcagca acatgtctgc gcaggctgcc ggaaaaagca gtacagaaaa gaaatacatt    120
gtcggattta aacagacaat gagtgccatg agttccgcca agaaaaagga tgttatttct    180
gaaaaaggcg gaaaggttca aaagcaattt aagtatgtta acgcggccgc agcaacattg    240
gatgaaaaag ctgtaaaaga attgaaaaaa gatccgagcg ttgcatatgt ggaagaagat    300
catattgcac atgaatatgc gcaatctgtt ccttatggca tttctcaaat taaagcgccg    360
gctcttcact ctcaaggcta cacaggctct aacgtaaaag tagctgttat cgacagcgga    420
attgactctt ctcatcctga cttaaacgtc agaggcggag caagctgggt accttctgaa    480
acaaacccat accaggacgg cagttctcac ggtacgcatg tagccggtac gattgccgct    540
cttaataact caatcggtgt tctgggcgta gcgccaagcg catcattata tgcagtaaaa    600
gtgcttgatt caacaggaag cggccaatat agctggatta ttaacggcat tgaatgggcc    660
atttccaaca atatggatgt tattaacatg agccttggcg gaccttctgg ttctacagcg    720
ctgaaaacag tcgttgataa agccgtttcc agcggtatcg tcgttgctgc cgctgccgga    780
aacgaaggtt cgtccggaag ctcaagcaca gtcggctacc ctgcaaaata tccttctact    840
attgcggtag gtgcggtaaa cagcagcaac caaagagctt catggtcaag cgcaggttct    900
gagcttgatg tgatggctcc tggcgtatcc atccaaagca cacttcctgg aggcacttac    960
ggtgcttaca acggcacgtc catggcgact cctcacgttg ccggagcagc agcgctaatt    1020
ctttctaagc acccgacttg gacaaacgcg caagtccgtg atcgtttaga aagcactgca    1080
acatatcttg gaaactcttt ctactatgga aagggttaa tcaacgtaca agcagctgca    1140
caataa                                                              1146
```

<210> SEQ ID NO 80
<211> LENGTH: 275
<212> TYPE: PRT
<213> ORGANISM: Bacillus subtilis
<220> FEATURE:
<223> OTHER INFORMATION: 10073aprE-W7

<400> SEQUENCE: 80

```
Ala Gln Ser Val Pro Tyr Gly Ile Ser Gln Ile Lys Ala Pro Ala Leu
1               5                   10                  15

His Ser Trp Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Trp Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Ser Gly Ser Thr Ala Leu Lys Thr Val Asp Lys Ala Val Ser
    130                 135                 140

Ser Gly Ile Val Val Ala Ala Ala Gly Asn Glu Gly Ser Ser Gly
145                 150                 155                 160
```

-continued

```
Ser Ser Ser Thr Val Gly Tyr Pro Ala Lys Tyr Pro Ser Thr Ile Ala
            165             170             175

Val Gly Ala Val Asn Ser Ser Asn Gln Arg Ala Ser Trp Ser Ser Ala
            180             185             190

Gly Ser Glu Leu Asp Val Met Ala Pro Gly Val Ser Ile Gln Ser Thr
        195             200             205

Leu Pro Gly Gly Thr Tyr Gly Ala Tyr Asn Gly Thr Ser Met Ala Thr
        210             215             220

Pro His Val Ala Gly Ala Ala Leu Ile Leu Ser Lys His Pro Thr
225             230             235             240

Trp Thr Asn Ala Gln Val Arg Asp Arg Leu Glu Ser Thr Ala Thr Tyr
            245             250             255

Leu Gly Asn Ser Trp Tyr Tyr Gly Lys Gly Leu Ile Asn Val Gln Ala
            260             265             270

Ala Ala Gln
        275
```